US011279974B2

(12) United States Patent
Lieberman-Aiden et al.

(10) Patent No.: US 11,279,974 B2
(45) Date of Patent: Mar. 22, 2022

(54) METHOD FOR IN SITU DETERMINATION OF NUCLEIC ACID PROXIMITY

(71) Applicants: THE BROAD INSTITUTE, INC., Cambridge, MA (US); BAYLOR COLLEGE OF MEDICINE, Houston, TX (US)

(72) Inventors: Erez Lieberman-Aiden, Houston, TX (US); Suhas Rao, Medfield, MA (US); Elena Stamenova, Reading, MA (US); Olga Dudchenko, Houston, TX (US); Eric Lander, Cambridge, MA (US)

(73) Assignees: THE BROAD INSTITUTE, INC., Cambridge, MA (US); BAYLOR COLLEGE OF MEDICINE, Houston, TX (US)

( * ) Notice: Subject to any disclaimer, the term of this patent is extended or adjusted under 35 U.S.C. 154(b) by 372 days.

(21) Appl. No.: 15/532,353

(22) PCT Filed: Dec. 1, 2015

(86) PCT No.: PCT/US2015/063272
§ 371 (c)(1),
(2) Date: Jun. 1, 2017

(87) PCT Pub. No.: WO2016/089920
PCT Pub. Date: Jun. 9, 2016

(65) Prior Publication Data
US 2017/0362649 A1 Dec. 21, 2017

Related U.S. Application Data

(60) Provisional application No. 62/085,851, filed on Dec. 1, 2014.

(51) Int. Cl.
*C12Q 1/68* (2018.01)
*C12Q 1/6869* (2018.01)
(Continued)

(52) U.S. Cl.
CPC ......... *C12Q 1/6869* (2013.01); *C12Q 1/6806* (2013.01); *C40B 30/04* (2013.01);
(Continued)

(58) Field of Classification Search
USPC ........... 435/6.1, 6.11, 91.1, 320.1, 459, 465; 436/94, 501; 536/23.1, 24.3
See application file for complete search history.

(56) References Cited

U.S. PATENT DOCUMENTS 3,817,837 A   6/1974   Rubenstein et al.
3,850,752 A   11/1974  Schuurs et al.
(Continued)

FOREIGN PATENT DOCUMENTS

CN   104059877 A   9/2014
EP   0 320 308 A2  6/1989
(Continued)

OTHER PUBLICATIONS

Rao et al., Cohesin Loss Eliminates All Loop Domains. Cell, 171,305-320, 2017.*
(Continued)

*Primary Examiner* — Frank W Lu
(74) *Attorney, Agent, or Firm* — F. Brent Nix, Esq.; Michael B. Scher, Esq.; Johnson, Marcou, Isaacs & Nix, LLC

(57) ABSTRACT

Disclosed is an in situ method for detecting spatial proximity relationships between nucleic acid sequences, such as DNA, in a cell. The method includes: providing a sample of one or more cells comprising nucleic acids; fragmenting the nucleic acids present in the cells that leaves 5' overhanging ends; filling in the overhanging ends with at least one labeled nucleotide; joining the filled in end of the fragmented nucleic acids that are in close physical proximity to create one or more end joined nucleic acid fragments having a (Continued)

junction; isolating the one or more end joined nucleic acid fragments using the labeled nucleotide; and determining the sequence at the junction of the one or more end joined nucleic acid fragments.

25 Claims, 9 Drawing Sheets

Specification includes a Sequence Listing.

(51) Int. Cl.
C12Q 1/6806 (2018.01)
C40B 30/04 (2006.01)
C40B 20/00 (2006.01)

(52) U.S. Cl.
CPC .. C12Q 2521/501 (2013.01); C12Q 2525/117 (2013.01); C12Q 2535/122 (2013.01); C12Q 2563/131 (2013.01); C40B 20/00 (2013.01)

(56) References Cited

U.S. PATENT DOCUMENTS

| | | | |
|---|---|---|---|
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,366,241 A | 12/1982 | Tom et al. | |
| 5,427,930 A | 6/1995 | Birkenmeyer et al. | |
| 5,744,311 A | 4/1998 | Fraiser et al. | |
| 5,866,366 A | 2/1999 | Kallender et al. | |
| 6,025,134 A | 2/2000 | Sooknanan | |
| 6,027,889 A | 2/2000 | Barany et al. | |
| 6,033,881 A | 3/2000 | Himmler et al. | |
| 6,849,400 B1* | 2/2005 | Harvey | C12Q 1/6809 435/6.14 |
| 2012/0295262 A1 | 11/2012 | Ronaghi et al. | |
| 2013/0079231 A1 | 3/2013 | Pushkarev et al. | |
| 2013/0096009 A1 | 4/2013 | Dekker et al. | |
| 2016/0168594 A1* | 6/2016 | Zhang | C12N 9/22 435/463 |

FOREIGN PATENT DOCUMENTS

| | | |
|---|---|---|
| WO | 90/01069 A1 | 2/1990 |
| WO | 0102553 A2 | 1/2001 |
| WO | 0183793 A2 | 11/2001 |
| WO | 2010/036323 A1 | 4/2010 |
| WO | 2010036323 A1 | 4/2010 |
| WO | 2012/005595 A2 | 1/2012 |
| WO | 2012005595 A2 | 1/2012 |
| WO | 2012/159025 A2 | 11/2012 |
| WO | 2012159025 A2 | 11/2012 |
| WO | 2014144491 A1 | 9/2014 |

OTHER PUBLICATIONS

"Cohesion" from Wikipedia, the free encyclopedia. Printed on May 24, 2019. Zhou et al., One-step generation of different immunodeficient mice with multiple gene modifications by CRISPR/Cas9 mediated genome. The international Journal of Biochemistry & Cell Biology, 46, 49-55, available online on Nov. 20, 2013.*
Mendenhall et al., Locus-specific editing of histone modifications at endogenous enhancers. Nature Biotechnology, 31, 1133-1136, published online on Sep. 8, 2013.*
Khrameeva et al., Spatial Proximity and Similarity of the Epigenetic State of Genome Domains. PLos One, 7, e33947, 2012.*
Meganuclease and Transcription activator-like effector nucleases from Wikipedia, the free encyclopedia. Printed on May 7, 2020.*
Carlson et al., Targeting DNA With Fingers and TALENs. Molecular Therapy-Nucleic Acids 1, e3, 2012. Bak et al., Gene Editing on Center Stage.Trends in Genetics, 34, 600-611, 2018.*
Splinter et al., CTCF mediates long-range chromatin looping and local histone modification in the β-globin locus.Genes & Development 20, 2349-2354, 2006.*
Gregor et al., De Novo Mutations in the Genome Organizer CTCF Cause Intellectual Disability.The American Journal of Human Genetics, 93, 124-131, Jul. 11, 2013.*
"CRISPR" and "CRISPR gene editing" from Wikipedia. Printed on May 21, 2021.*
Holwerda et al., CTCF: the protein, the binding partners, the binding sites and their chromatin loops. Philos Trans R Soc Lond B Biol Sci., 368(1620), 20120369, Jun. 19, 2013.*
International Preliminary Report on Patentability for PCT International Application No. PCT/US2015/063272, dated Jun. 15, 2017, 1-11.
"Supplemental European Search Report issued in EPO Application No. 15865948.2", dated Apr. 18, 2018, 1-12.
Sandhu, et al., "Chromatin Interaction Networks and Higher Order Architectures of Eukaryotic Genomes", Apr. 25, 2011, 1-4.
International Search Report and Written Opinion for PCT International Application No. PCT/US2015/063272, dated Mar. 31, 2016, 16.
Bassett, et al., "CRISPR/Cas9 and Genome Editing in *Drosophila*", Journal of Genetics and Genomics, Elsevier BV, No. vol. 41, No. 1, Dec. 18, 2013, pp. 7-19, XP028826531.
Celler, "Communication pursuant to Article 94(3) EPC, EP15865948. 2, dated Feb. 11, 2019", 10 pages.
Dolce, "Supplementary European Search Report for EP15865948. 2", dated Jun. 5, 2018, 12 pages.
Keung,, et al., "Using Targeted Chromatin Regulators to Engineer Combinatorial and Spatial Transcriptional Regulation", Cell, vol. 158, No. 1, Jul. 3, 2014 (Jul. 3, 2014), pp. 110-120, XP028862105.
Yaffe, et al., "Probabilistic Modeling of Hi-c Contact Maps Eliminates Systematic Biases to Characterize Global Chromosomal Architecture", Nature Genetics, vol. 43, No. 11, Oct. 16, 2011, 1059-1065.
Barski, et al., "High-resolution Profiling of Histone Methylations in The Human Genome", Cell, vol. 129, No. 4, May 18, 2007, 823-837.
Bickmore, "The Spatial Organization of the Human Genome", Annual Review of Genomics and Human Genetics, vol. 14, 2013, 67-84.
Chadwick, et al., "DXZ4 Chromatin Adopts an Opposing Conformation to that of the Surrounding Chromosome and Acquires a Novel Inactive X-Specific Role Involving CTCF and Antisense Transcripts", Genome Research, vol. 18, 2008, 1259-1269.
Cong, et al., "Multiplex Genome Engineering Using CRISPR/Cas Systems", Science, vol. 339, No. 6121, Feb. 15, 2013, 819-823.
Cournac, et al., "Normalization of a Chromosomal Contact Map", BMC Genomics, vol. 13, No. 436, 2012, 13 pages.
Cullen, et al., "Interaction Between Transcription Regulatory Regions of Prolactin Chromatin", Science, vol. 261, No. 5118, Jul. 9, 1993, 203-206.
Dekker, et al., "Capturing Chromosome Conformation", Science, vol. 295, No. 5558, Feb. 15, 2002, 1306-1311.
Dixon, et al., "Topological Domains in Mammalian Genomes Identified by Analysis of Chromatin Interactions", Nature, vol. 485, No. 7398, Apr. 11, 2012, 376-380.
Dostie, et al., "Chromosome Conformation Capture Carbon Copy (5C): A Massively Parallel Solution for Mapping Interactions Between Genomic Elements", Genome Research, vol. 16, No. 10, Oct. 2006, 1299-1309.
Gaszner, et al., "Insulators: Exploiting Transcriptional and Epigenetic Mechanisms", Nature Reviews Genetics, vol. 7, No. 9, Sep. 2006, 703-713.
Gerasimova, et al., "A Chromatin Insulator Determines the Nuclear Localization of DNA", Molecular Cell, vol. 6, No. 5, Nov. 2000, 1025-1035.
Hahn, et al., "Relationship between Gene Body DNA Methylation and Intragenic H3K9me3 and H3K36me3 Chromatin Marks", PLoS ONE, vol. 6, No. 4, e18844, Apr. 2011, 12 pages.

(56) References Cited

OTHER PUBLICATIONS

Horakova, et al., "The Macrosatellite DXZ4 Mediates CTCF-Dependent Long-Range Intrachromosomal Interactions on the Human Inactive X Chromosome", Human Molecular Genetics, vol. 21, No. 20, Oct. 15, 2012, 4367-4377.
Hsu, et al., "Development and Applications of CRISPR-Cas9 for Genome Engineering", Cell, vol. 157, No. 6, Jun. 5, 2014, 1262-1278.
Hu, et al., "HICNorm: Removing Biases in Hi-C Data via Poisson Regression", Bioinformatics, vol. 28, No. 23, Sep. 27, 2012, 3131-3133.
Imakaev, et al., "Iterative Correction of Hi-C Data Reveals Hallmarks of Chromosome Organization", Nature Methods, vol. 9, No. 10, Oct. 2012, 999-1003.
Kalhor, et al., "Genome Architectures Revealed by Tethered Chromosome Conformation Capture and Population-based Modeling", Nature Biotechnology, vol. 30, No. 1, Jan. 2012, 90-98.
Kim, et al., "Analysis of the Vertebrate Insulator Protein CTCF Binding Sites in the Human Genome", Cell, vol. 128, No. 6, Mar. 23, 2007, 1231-1245.
Lieberman-Aiden, et al., "Comprehensive Mapping of Long-Range Interactions Reveals Folding Principles of the Human Genome", Science, vol. 326, No. 5950, Oct. 9, 2009, 289-293.
McCord, et al., "Correlated Alterations in Genome Organization, Histone Methylation, and DNA—Lamin A/C Interactions in Hutchinson-Gilford Progeria Syndrome", Genome Research, vol. 23, No. 2, Feb. 2013, 260-269.
Nora, et al., "Spatial Partitioning of the Regulatory Landscape of the Xinactivation Center", Nature, vol. 485, No. 7398, Apr. 11, 2012, 381-385.
Platt, et al., "CRISPR-Cas9 Knockin Mice for Genome Editing and Cancer Modelling", Cell, vol. 159, No. 2, Oct. 9, 2014, 440-455.
Rao, et al., "A 3D Map of the Human Genome at Kilobase Resolution Reveals Principles of Chromatin Looping", Cell, vol. 159, No. 7, Dec. 18, 2014, 1665-1680.
Rickman, et al., "Oncogene-Mediated Alterations in Chromatin Conformation", Proceedings of the National Academy of Sciences, vol. 109, No. 23, Jun. 5, 2012, 9083-9088.
Schmidt, et al., "Waves of Retrotransposon Expansion Remodel Genome Organization and Ctcf Binding in Multiple Mammalian Lineages", Cell, vol. 148, No. (1-2), Jan. 20, 2012, 335-348.
Sexton, et al., "Three-dimensional Folding and Functional Organization Principles of the *Drosophila* Genome", Cell, vol. 148, No. 3, Feb. 3, 2012, 458-472.
Shalem, et al., "Genome-Scale CRISPR-Cas9 Knockout Screening in Human Cells", Science, vol. 343, No. 6166, Jan. 3, 2014, 84-87.
Tolhuis, et al., "Looping and Interaction Between Hypersensitive Sites in the Active β-Globin Locus", Molecular Cell, vol. 10, No. 6, Dec. 2002, 1453-1465.
"Extended European Search Report issued by the European Patent Office dated Oct. 27, 2020 for European Application No. 20170063.0."
Murrell, et al., "Interaction Between Differentially Methylated Regions Partitions the Imprinted Genes Igf2 and H19 Into Parent-specific Chromatin Loops", Nature Genetics, vol. 36, No. 8, Aug. 2004, 889-893.

\* cited by examiner

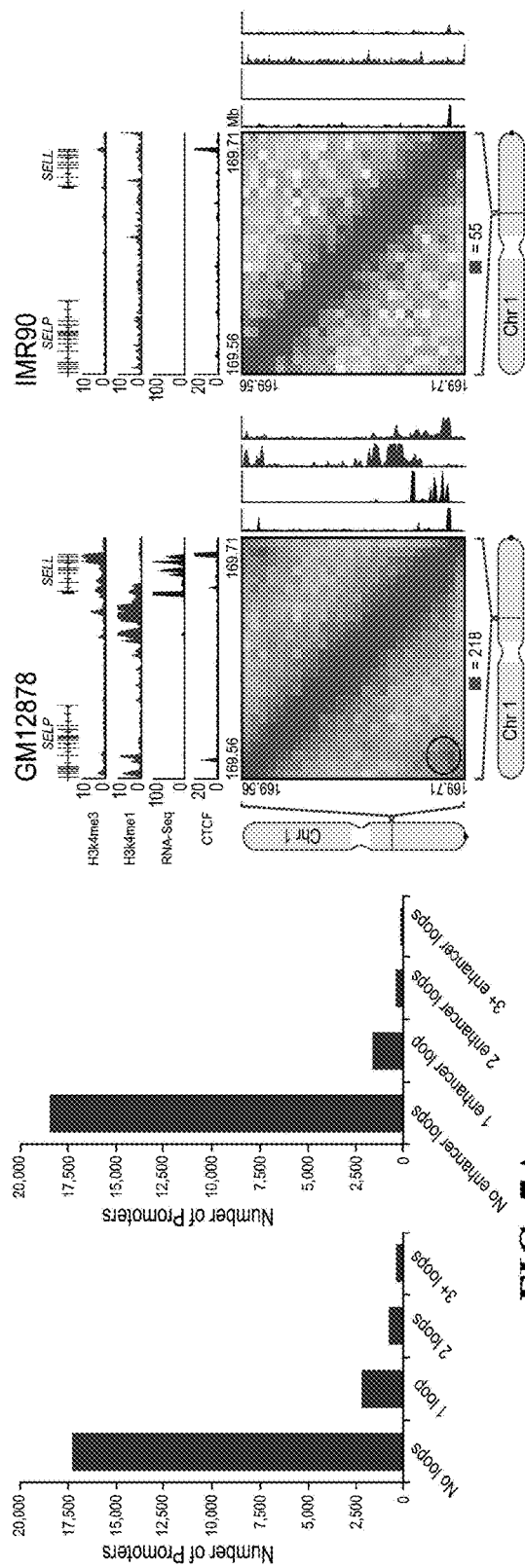
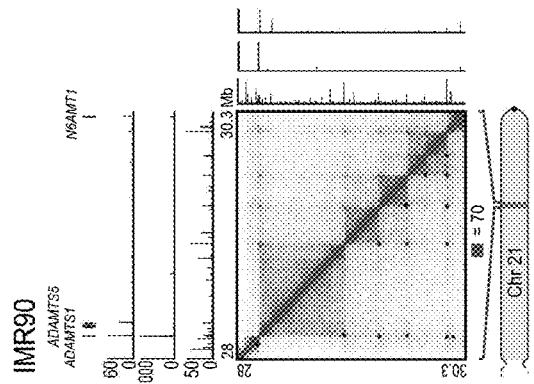
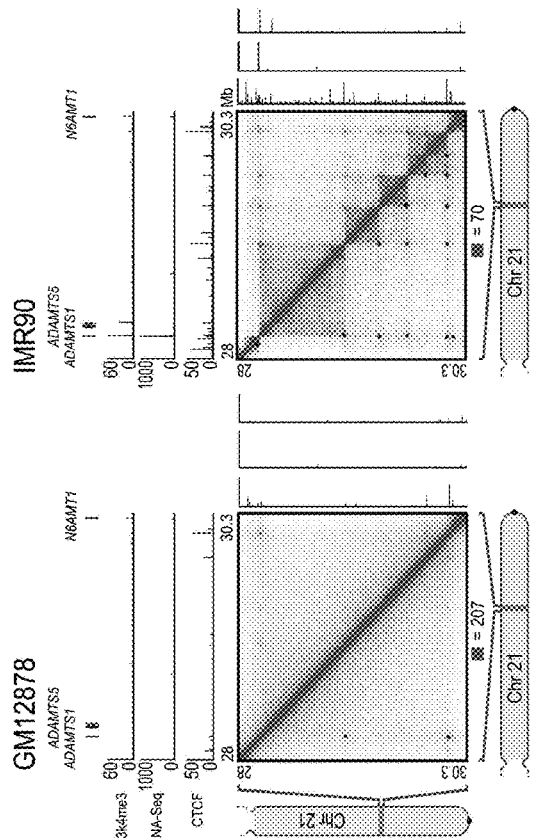
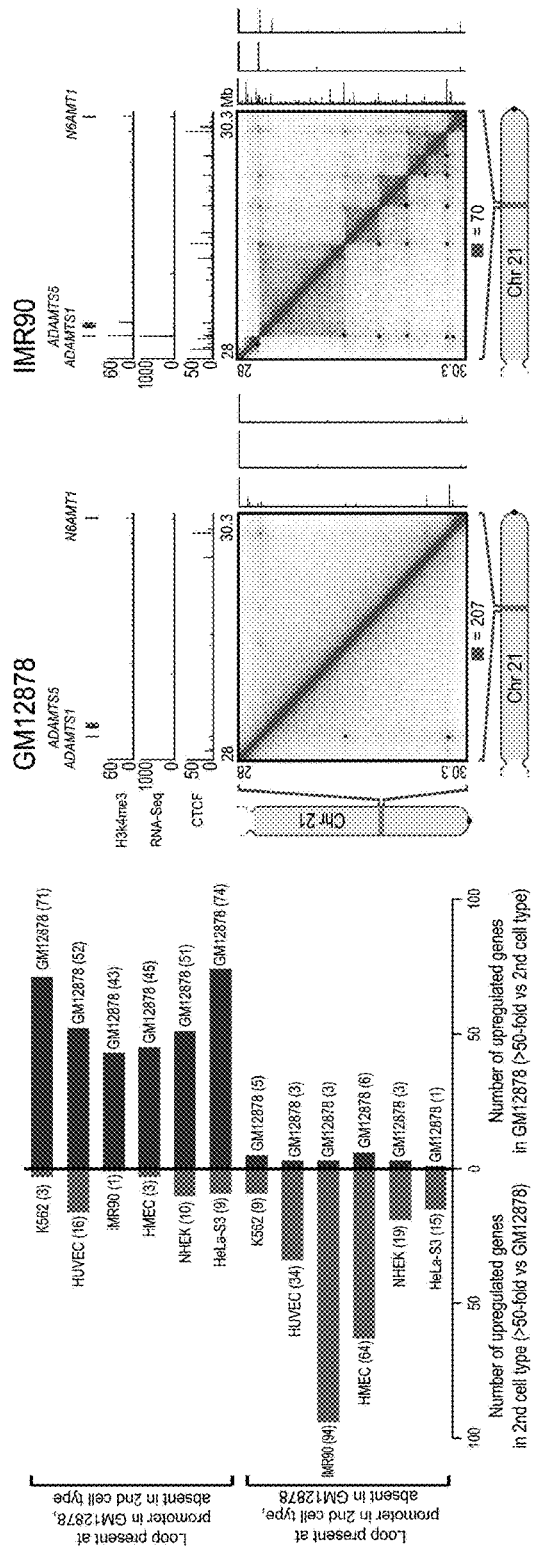
FIG. 7A
FIG. 7B
FIG. 7C
FIG. 7D

METHOD FOR IN SITU DETERMINATION OF NUCLEIC ACID PROXIMITY

This invention was made with government support under Grant Nos. OD008540, HG006193, and HG003067 awarded by the National Institutes of Health, and Grant No. PHY1427654 awarded by the National Science Foundation. The government has certain rights in the invention.

TECHNICAL FIELD

This disclosure concerns methods for identifying nucleic acids in close proximity within a cell or system.

BACKGROUND

It has been suggested that the three-dimensional structure of nucleic acids in a cell may be involved in complex biological regulation, for example compartmentalizing the nucleus and bringing widely separated functional elements into close spatial proximity. Understanding how nucleic acids interact, and perhaps more importantly how this interaction, or lack thereof, regulates cellular processes, presents a new frontier of exploration. For example, understanding chromosomal folding and the patterns therein can provide insight into the complex relationships between chromatin structure, gene activity, and the functional state of the cell. Adding ribonucleic acids (RNAs) into the mix adds a further level of complexity.

Typically, deoxyribonucleic acid (DNA) is viewed as a linear molecule, with little attention paid to the three-dimensional organization. However chromosomes are not rigid, and while the linear distance between two genomic loci indeed may be vast, when folded, the special distance may be small. For example, while regions of chromosomal DNA may be separated by many megabases, they can also can be immediately adjacent in 3-dimensional space. Much the same way a protein can fold to bring sequence elements together to form an active site, from the standpoint of gene regulation, long-range interactions between genomic loci may form active centers. For example, gene enhancers, silencers, and insulator elements might function across vast genomic distances.

The existence of long-range interactions complicates efforts to understand the pathways that regulate cellular processes, because the interacting regulatory elements could lie at a great genomic distance from a target gene, even on another chromosome. In the case of oncogenes and other disease-associated genes, identification of long-range genetic regulators would be of great use in identifying the genomic variants responsible for the disease state and the process by which the disease state is brought about.

SUMMARY OF THE DISCLOSURE

Disclosed is an in situ method for detecting spatial proximity relationships between nucleic acid sequences, such as DNA, in a cell or acellular system. The method includes: providing a sample comprising nucleic acids, such as a sample of one or more cells; fragmenting the nucleic acids present in the cells, wherein the fragmented nucleic acids are fragmented to create overhanging ends, such as by enzymatic digestion with a endonuclease that leaves overhanging or blunt ends; marking the ends with at least one labeled nucleotide, wherein the labeled nucleotide can be used to isolate the nucleic acids; joining, for example using a DNA ligase, the labeled end of the fragmented nucleic acids that are in close physical proximity to create one or more end joined nucleic acid fragments having a junction, wherein the site of the junction comprises one or more labeled nucleic acids; isolating the one or more end joined nucleic acid fragments using the labeled nucleotide; and determining the sequence at the junction of the one or more end joined nucleic acid fragments, thereby detecting spatial proximity relationships between nucleic acid sequences. In some embodiments, the nucleic acids and cellular components are not held in a fixed position relative to one another. In some embodiments, cells are embedded in agarose or other polymer. In some embodiments of the disclosed method, the nucleic acids present in the cell, or cells, are fixed in position relative to one another by crosslinking, for example by treatment of the cells with a chemical crosslinker, for example an aldehyde, such as formaldehyde. In some embodiments, the crosslinking is reversed after end joining, for example to free the end joined nucleic acids for subsequent analysis.

In some embodiments, of the disclosed method, the location of nucleic acid sequences both 5' and 3' of the junction of the one or more end joined nucleic acid fragments is identified relative to genome and/or chromosomal location. In some embodiments, the presence of a junction is correlated with a disease state and/or an environmental condition.

In some embodiments of the disclosed method, the labeled nucleotide present in the end joined nucleic acids is isolated with a specific binding agent that specifically binds to the label, thereby isolating the end joined nucleic acids. In some embodiments, the specific binding agent is attached to a solid surface.

In some embodiments, the nucleic acid fragments are end repaired, for example to facilitate attaching sequencing adapters to the ends of the end joined nucleic acid fragments. In some embodiments, sequencing adapters are attached to the ends of the end joined nucleic acid fragments, such as the ends that are not joined.

In embodiments of the disclosed methods, determining the junction of the one or more end joined nucleic acid fragments includes nucleic acid sequencing, that is sequencing the nucleotide bases 3' and 5' of the junction, for example so that the sequences 3' and 5' of the junction can be mapped to locations within the chromosomes. In some embodiments of the disclosed method, determining the sequence of the junction of the one or more end joined nucleic acid fragments includes using a probe, such as an RNA probe, a DNA probe, a locked nucleic acid (LNA) probe, a peptide nucleic acid (PNA) probe, or a hybrid RNA-DNA probe, that specifically hybridizes to the nucleic acid sequences both 5' and 3' of the junction of the one or more end joined nucleic acid fragments.

Also disclosed is a method for diagnosing a disease or condition, the method including: detecting, in a sample, at least one junction that is indicative of a disease or condition, wherein detection of the at least one junction that is indicative of a disease or condition diagnoses the disease or condition.

Further disclosed are isolated nucleic acid probes that specifically bind to a junction in an end joined nucleic acid fragment, wherein the probe specifically hybridizes to the end joined nucleic acid fragment both 5' and 3' of the site of the junction and spans the site of the junction or specifically binds a specific nucleic acid sequence within the end joined fragment, as well as kit and devices containing such probes.

BRIEF DESCRIPTION OF THE FIGURES

FIG. 7. Loops between promoters and enhancers are strongly associated with gene activation. (A) Histogram showing loop count at promoters (left); restricted to loops where the distal peak locus contains an enhancer (right). (B) Genes whose promoters participate in a loop in GM12878 but not in a second cell type are frequently upregulated in GM12878, and vice-versa. (C) Left: a loop in GM12878, with one anchor at the SELL promoter and the other at a distal enhancer. The gene is on. Right: The loop is absent in IMR90, where the gene is off. (D) Left: Two loops in GM12878 are anchored at the promoter of the inactive ADAMTS1 gene. Right: A series of loops and domains appear, along with evident transitive looping. ADAMTS1 is on.

Figure 1:
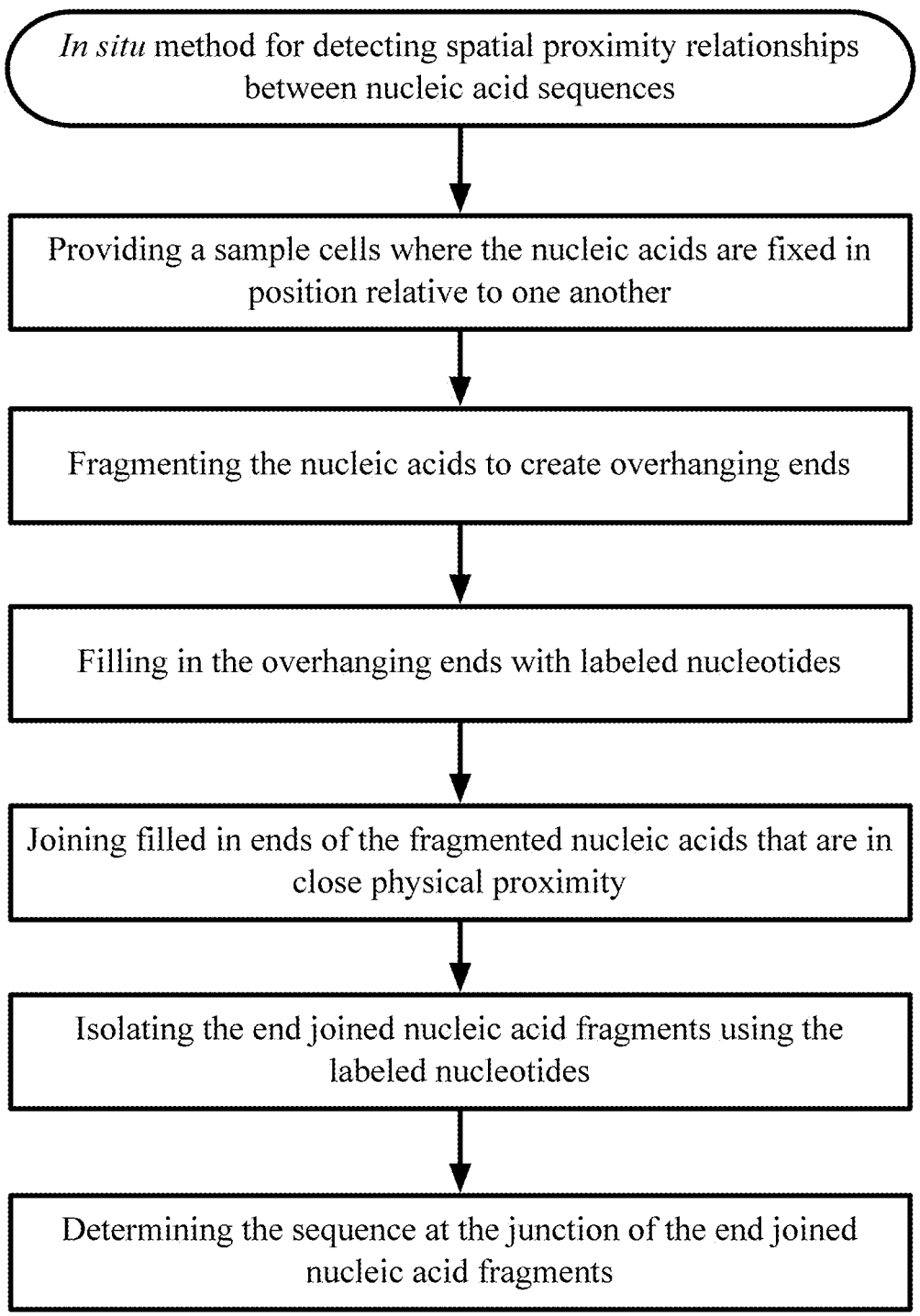
FIG. 1 is an exemplary flow diagram of exemplary methods disclosed herein. The flow diagram is for illustrative purposes only and it is envisioned that the method disclosed herein can have more or fewer steps than shown in the diagram.

(bottom right); it is absent from the maternal GM12878 map (middle left) and the map of the male HUVEC cell line (bottom left).

DETAILED DESCRIPTION OF SEVERAL EMBODIMENTS

I. Summary of Terms

Unless otherwise noted, technical terms are used according to conventional usage. Definitions of common terms in molecular biology may be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710).

The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

To facilitate review of the various embodiments of this disclosure, the following explanations of specific terms are provided:

Amplification: To increase the number of copies of a nucleic acid molecule, such as one or more end joined nucleic acid fragments that includes a junction, such as a ligation junction. The resulting amplification products are called "amplicons." Amplification of a nucleic acid molecule (such as a DNA or RNA molecule) refers to use of a technique that increases the number of copies of a nucleic acid molecule (including fragments).

An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR; reverse transcriptase PCR (RT-PCR); real-time PCR (rt PCR); real-time reverse transcriptase PCR (rt RT-PCR); nested PCR; strand displacement amplification (see U.S. Pat. No. 5,744,311); transcription-free isothermal amplification (see U.S. Pat. No. 6,033,881, repair chain reaction amplification (see WO 90/01069); ligase chain reaction amplification (see European patent publication EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134) amongst others.

Binding or stable binding (of an oligonucleotide): An oligonucleotide, such as a nucleic acid probe that specifically binds to a target junction in an end joined nucleic acid fragment, binds or stably binds to a target nucleic acid if a sufficient amount of the oligonucleotide forms base pairs or is hybridized to its target nucleic acid. For example depending in the hybridization conditions, there need not be complete matching between the probe and the nucleic acid target, for example there can be mismatch, or a nucleic acid bubble. Binding can be detected by either physical or functional properties.

Binding site: A region on a protein, DNA, or RNA to which other molecules stably bind. In one example, a binding site is the site on an end joined nucleic acid fragment.

Biotin-14-CTP: A biologically active analog of cytosine-5'-triphosphate that is readily incorporated into a nucleic acid by polymerase or a reverse transcriptase. In some examples, biotin-14-CTP is incorporated into a nucleic acid fragment that has a 3' overhang.

Capture moieties: Molecules or other substances that when attached to a nucleic acid molecule, such as an end joined nucleic acid, allow for the capture of the nucleic acid molecule through interactions of the capture moiety and something that the capture moiety binds to, such as a particular surface and/or molecule, such as a specific binding molecule that is capable of specifically binding to the capture moiety.

Complementary: A double-stranded DNA or RNA strand consists of two complementary strands of base pairs. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

Contacting: Placement in direct physical association, including both in solid or liquid form, for example contacting a sample with a crosslinking agent or a probe.

Control: A reference standard. A control can be a known value or range of values indicative of basal levels or amounts or present in a tissue or a cell or populations thereof. A control can also be a cellular or tissue control, for example a tissue from a non-diseased state and/or exposed to different environmental conditions. A difference between a test sample and a control can be an increase or conversely a decrease. The difference can be a qualitative difference or a quantitative difference, for example a statistically significant difference.

Covalently linked: Refers to a covalent linkage between atoms by the formation of a covalent bond characterized by the sharing of pairs of electrons between atoms. In one example, a covalent link is a bond between an oxygen and a phosphorous, such as phosphodiester bonds in the backbone of a nucleic acid strand. In another example, a covalent link is one between a nucleic acid protein, another protein and/or nucleic acid that has been crosslinked by chemical means. In another example, a covalent link is one between fragmented nucleic acids.

Crosslinking agent: A chemical agent or even light, which facilitates the attachment of one molecule to another molecule. Crosslinking agents can be protein-nucleic acid crosslinking agents, nucleic acid-nucleic acid crosslinking agents, and protein-protein crosslinking agents. Examples of such agents are known in the art. In some embodiments, a crosslinking agent is a reversible crosslinking agent. In some embodiments, a crosslinking agent is a non-reversible crosslinking agent.

Detect: To determine if an agent (such as a signal or particular nucleic acid or protein) is present or absent. In some examples, this can further include quantification in a sample, or a fraction of a sample, such as a particular cell or cells within a tissue.

Detectable label: A compound or composition that is conjugated directly or indirectly to another molecule to facilitate detection of that molecule. Specific, non-limiting examples of labels include fluorescent tags, enzymatic linkages, and radioactive isotopes and other physical tags, such as biotin. In some examples, a label is attached to a nucleic acid, such as an end-joined nucleic acid, to facilitate detection and/or isolation of the nucleic acid.

DNA sequencing: The process of determining the nucleotide order of a given DNA molecule. Generally, the sequencing can be performed using automated Sanger sequencing (AB13730x1 genome analyzer), pyrosequencing on a solid support (454 sequencing, Roche), sequencing-by-synthesis with reversible terminations (ILLUMINA® Genome Analyzer), sequencing-by-ligation (ABI SOLiD®) or sequencing-by-synthesis with virtual terminators (HELISCOPE®).

In some embodiments, DNA sequencing is performed using a chain termination method developed by Frederick Sanger, and thus termed "Sanger based sequencing" or "SBS." This technique uses sequence-specific termination of a DNA synthesis reaction using modified nucleotide substrates. Extension is initiated at a specific site on the template DNA by using a short oligonucleotide primer complementary to the template at that region. The oligonucleotide primer is extended using DNA polymerase in the presence of the four deoxynucleotide bases (DNA building blocks), along with a low concentration of a chain terminating nucleotide (most commonly a di-deoxynucleotide). Limited incorporation of the chain terminating nucleotide by the DNA polymerase results in a series of related DNA fragments that are terminated only at positions where that particular nucleotide is present. The fragments are then size-separated by electrophoresis a polyacrylamide gel, or in a narrow glass tube (capillary) filled with a viscous polymer. An alternative to using a labeled primer is to use labeled terminators instead; this method is commonly called "dye terminator sequencing."

"Pyrosequencing" is an array based method, which has been commercialized by 454 Life Sciences. In some embodiments of the array-based methods, single-stranded DNA is annealed to beads and amplified via EmPCR®. These DNA-bound beads are then placed into wells on a fiber-optic chip along with enzymes that produce light in the presence of ATP. When free nucleotides are washed over this chip, light is produced as the PCR amplification occurs and ATP is generated when nucleotides join with their complementary base pairs. Addition of one (or more) nucleotide(s) results in a reaction that generates a light signal that is recorded, such as by the charge coupled device (CCD) camera, within the instrument. The signal strength is proportional to the number of nucleotides, for example, homopolymer stretches, incorporated in a single nucleotide flow.

Fluorophore: A chemical compound, which when excited by exposure to a particular stimulus such as a defined wavelength of light, emits light (fluoresces), for example at a different wavelength (such as a longer wavelength of light).

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) eliminates the need for an external source of electromagnetic radiation, such as a laser.

Examples of particular fluorophores that can be used in the probes disclosed herein are provided in U.S. Pat. No. 5,866,336 issued to Nazarenko et al., such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-di sulfonic acid; 4,4'-diisothiocyanatostilbene-2,2'-disulfonic acid; 5-[dimethylamino] naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron™. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives; LightCycler Red 640; Cy5.5; and Cy56-carboxyfluorescein; 5-carboxyfluorescein (5-FAM); boron dipyrromethene difluoride (BODIPY); N,N,N',N'-tetramethyl-6-carboxyrhodamine (TAMRA); acridine, stilbene, -6-carboxy-fluorescein (HEX), TET (Tetramethyl fluorescein), 6-carboxy-X-rhodamine (ROX), Texas Red, 2',7'-dimethoxy-4',5'-dichloro-6-carboxyfluorescein (JOE), Cy3, Cy5, VIC® (Applied Biosystems), LC Red 640, LC Red 705, Yakima yellow amongst others.

High throughput technique: Through a combination of robotics, data processing and control software, liquid handling devices, and detectors, high throughput techniques allows the rapid screening of potential reagents, conditions, or targets in a short period of time, for example in less than 24, less than 12, less than 6 hours, or even less than 1 hour.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or it's analog) and the DNA, RNA, and or DNA-RNA hybrid target. The oligonucleotide or oligonucleotide analog need not be 100% complementary to its target sequence to be specifically hybridizable. An oligonucleotide or analog is specifically hybridizable when there is a sufficient degree of complementarity to avoid non-specific binding of the oligonucleotide or analog to non-target sequences under conditions where specific binding is desired. Such binding is referred to as specific hybridization.

Isolated: An "isolated" biological component (such as the end joined fragmented nucleic acids described herein) has been substantially separated or purified away from other biological components in the cell of the organism, in which the component naturally occurs, for example, extra-chromatin DNA and RNA, proteins and organelles. Nucleic acids and proteins that have been "isolated" include nucleic acids and proteins purified by standard purification methods, for example from a sample. The term also embraces nucleic acids and proteins prepared by recombinant expression in a host cell as well as chemically synthesized nucleic acids. It is understood that the term "isolated" does not imply that the biological component is free of trace contamination, and can include nucleic acid molecules that are at least 50% isolated, such as at least 75%, 80%, 90%, 95%, 98%, 99%, or even 100% isolated.

Junction: A site where two nucleic acid fragments or joined, for example using the methods described herein. A junction encodes information about the proximity of the nucleic acid fragments that participate in formation of the junction. For example, junction formation between to nucleic acid fragments indicates that these two nucleic acid sequences where in close proximity when the junction was formed, although they may not be in proximity in liner nucleic acid sequence space. Thus, a junction can define ling range interactions. In some embodiments, a junction is labeled, for example with a labeled nucleotide, for example to facilitate isolation of the nucleic acid molecule that includes the junction.

Nucleic acid (molecule or sequence): A deoxyribonucleotide or ribonucleotide polymer including without limitation, cDNA, mRNA, genomic DNA, and synthetic (such as chemically synthesized) DNA or RNA or hybrids thereof. The nucleic acid can be double-stranded (ds) or single-stranded (ss). Where single-stranded, the nucleic acid can be the sense strand or the antisense strand. Nucleic acids can include natural nucleotides (such as A, T/U, C, and G), and can also include analogs of natural nucleotides, such as labeled nucleotides. Some examples of nucleic acids include the probes disclosed herein.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U). Nucleotides include those nucleotides containing modified bases, modified sugar moieties, and modified phosphate backbones, for example as described in U.S. Pat. No. 5,866,336 to Nazarenko et al.

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methyl cytosine, N6-adenine, 7-methylguanine, 5-methylaminomethyluracil, methoxyarninomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, 2,6-diaminopurine and biotinylated analogs, amongst others.

Examples of modified sugar moieties which may be used to modify nucleotides at any position on its structure include, but are not limited to arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Primers: Short nucleic acid molecules, such as a DNA oligonucleotide, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule, wherein the sequence of the primer is specific for the target nucleic acid molecule, for example so that the primer will hybridize to the target nucleic acid molecule under very high stringency hybridization conditions.

The specificity of a primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 5, 10, 15, 20, 25, 30, 35, 40, 45, 50 or more consecutive nucleotides.

In particular examples, a primer is at least 15 nucleotides in length, such as at least 5 contiguous nucleotides complementary to a target nucleic acid molecule. Particular lengths of primers that can be used to practice the methods of the present disclosure include primers having at least 5, at least 10, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, or more contiguous nucleotides complementary to the target nucleic acid molecule to be amplified, such as a primer of 5-60 nucleotides, 15-50 nucleotides, 15-30 nucleotides or greater.

Primer pairs can be used for amplification of a nucleic acid sequence, for example, by PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction. PCR primer pairs can be derived from a known sequence, for example, by using computer programs intended for that purpose such as Primer (Version 0.5, © 1991, Whitehead Institute for Biomedical Research, Cambridge, Mass.).

Methods for preparing and using primers are described in, for example, Sambrook et al. (1989) *Molecular Cloning: A Laboratory Manual*, Cold Spring Harbor, N.Y.; Ausubel et al. (1987) *Current Protocols in Molecular Biology*, Greene Publ. Assoc. & Wiley-Intersciences.

Probe: A probe comprises an isolated nucleic acid capable of hybridizing to a target nucleic acid (such as end joined nucleic acid fragment). A detectable label or reporter molecule can be attached to a probe. Typical labels include radioactive isotopes, enzyme substrates, co-factors, ligands, chemiluminescent or fluorescent agents, haptens, and enzymes.

Methods for labeling and guidance in the choice of labels appropriate for various purposes are discussed, for example, in Sambrook et al., *Molecular Cloning: A Laboratory Manual*, Cold Spring Harbor Laboratory Press (1989) and Ausubel et al., *Current Protocols in Molecular Biology*, Greene Publishing Associates and Wiley-Intersciences (1987).

Probes are generally at least 5 nucleotides in length, such as at least 10, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, or more contiguous nucleotides complementary to the target nucleic acid molecule, such as 50-60 nucleotides, 20-50 nucleotides, 20-40 nucleotides, 20-30 nucleotides or greater.

Targeting probe: A probe that includes an isolated nucleic acid capable of hybridizing to a junction in a end joined nucleic acid fragment, wherein the probe specifically hybridizes to the end joined nucleic acid fragment both 5' and 3' of the site of the junction and spans the site of the junction.

Target junction: Any nucleic acid present or thought to be present in a sample that the information of a junction between an end joined nucleic acid fragment about which information would like to be obtained, such as its presence or absence.

Sample: A sample, such as a biological sample, that includes biological materials (such as nucleic acid and proteins, for example double-stranded nucleic acid binding proteins) obtained from an organism or a part thereof, such as a plant, animal, bacteria, and the like. In particular embodiments, the biological sample is obtained from an animal subject, such as a human subject. A biological sample is any solid or fluid sample obtained from, excreted by or secreted by any living organism, including without limitation, single celled organisms, such as bacteria, yeast, protozoans, and amebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease, such as a rheumatoid arthritis, osteoarthritis, gout or septic arthritis). A sample can also be a sample obtained from any organ or tissue (including a biopsy or autopsy specimen, such as a tumor biopsy) or can include a cell (whether a primary cell or cultured cell) or medium conditioned by any cell, tissue or organ.

Specific Binding Agent: An agent that binds substantially or preferentially only to a defined target such as a protein, enzyme, polysaccharide, oligonucleotide, DNA, RNA, recombinant vector or a small molecule. In an example, a "specific binding agent that specifically binds to the label" is capable of binding to a label that is covalently linked to a targeting probe.

A nucleic acid-specific binding agent binds substantially only to the defined nucleic acid, such as DNA, or to a specific region within the nucleic acid, for example a nucleic acid probe.

A protein-specific binding agent binds substantially only the defined protein, or to a specific region within the protein. For example, a "specific binding agent" includes antibodies and other agents that bind substantially to a specified polypeptide. Antibodies can be monoclonal or polyclonal antibodies that are specific for the polypeptide, as well as immunologically effective portions ("fragments") thereof. The determination that a particular agent binds substantially only to a specific polypeptide may readily be made by using or adapting routine procedures. One suitable in vitro assay makes use of the Western blotting procedure (described in many standard texts, including Harlow and Lane, *Using Antibodies: A Laboratory Manual*, CSHL, New York, 1999).

Test agent: Any agent that that is tested for its effects, for example its effects on a cell. In some embodiments, a test agent is a chemical compound, such as a chemotherapeutic agent, antibiotic, or even an agent with unknown biological properties.

Tissue: A plurality of functionally related cells. A tissue can be a suspension, a semi-solid, or solid. Tissue includes cells collected from a subject such as blood, cervix, uterus, lymph nodes breast, skin, and other organs.

Under conditions that permit binding: A phrase used to describe any environment that permits the desired activity, for example conditions under which two or more molecules, such as nucleic acid molecules and/or protein molecules, can bind.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999. In addition, the materials, methods, and examples are illustrative only and not intended to be limiting II. Description of Several Embodiments A. Introduction A major goal in modern biology is defining the interactions between different biological actors in vivo. Over the past few decades, major advances have been made in developing methods to identify the molecular interactions with any given protein. With nucleic acids and in particular genomic DNA it is difficult to determine the interactions in a cell in part because of enormity, at the sequence level, of genomic DNA in a cell. It is believed that genomic DNA adopts a fractal globule state in which the DNA organized in three dimensions such that functionally related genomic elements, for example enhancers and their target genes, are directly interacting or are located in very close spatial proximity. Such close physical proximity between such elements is further believed to play a role in genome biology both in normal development and homeostasis and in disease. During the cell cycle the particular proximity relationships change, further complicating the study of genome dynamics. Understanding, and perhaps controlling, these tertiary interactions at the nucleic acid level has enormous potential to further our understating of the complexities cellular dynamics and perhaps fostering the development of new classes of therapeutics. Thus, methods are needed to investigate these interactions. This disclosure meets those needs.

Genes are located at a particular position on a particular chromosome, but the elements that regulate their activity can lie far away. Understanding these distal regulatory sequences is essential to understanding how genes turn on and off in a healthy person, and how this process goes awry in disease. But finding distal regulatory sequences has been an open problem for over 30 years.

Using the three-dimensional genome sequencing approach disclosed herein, it is now possible to comprehensively identify all distal regulators of all genes in a sample population of cells. The information available, will make it possible to assess the impact of candidate drugs on specific cellular circuits, hastening the process of drug discovery and for biological research in general. The information available will also enable the mapping of genomic structural and sequence variations.

Disclosed herein is a method for detecting spatial proximity relationships between DNA in situ. By combining DNA-DNA proximity ligation with high throughput sequencing in order to measure how frequently positions in the human genome come into close physical proximity, the disclosed method can simultaneously map substantially all of the interactions of DNAs in a cell, including spatial arrangements of DNA. An flowchart depicting a non-limiting example of the methods disclosed is given in FIG. 1. Some of the advantages of the disclosed method are that is can be completed on a small sample of cells, without dilution of the sample. This lack of dilution yields many more contacts than previous methods used to define DNA/DNA interactions, such as chromosome Conformation Capture (3C) and Hi-C technology (see Dekker et al., Science 295:1306-1311 (2002) and Lieberman-Aiden et al., Science 326:289-93 (2009).

As demonstrated in Example 1 below, in situ determination of nucleic acid proximity as described results in surprising superior results over the Hi-C protocol. As shown in Example 1, the disclosed methods yield a result with greater complexity, which indicates more interactions that can be mapped and consequently more information. In addition, method disclosed herein provide more information on long distance intrachromosomal contacts. These contacts are the most informative ones, as they can pin down the long-range interactions in the cell.

Figure 2:
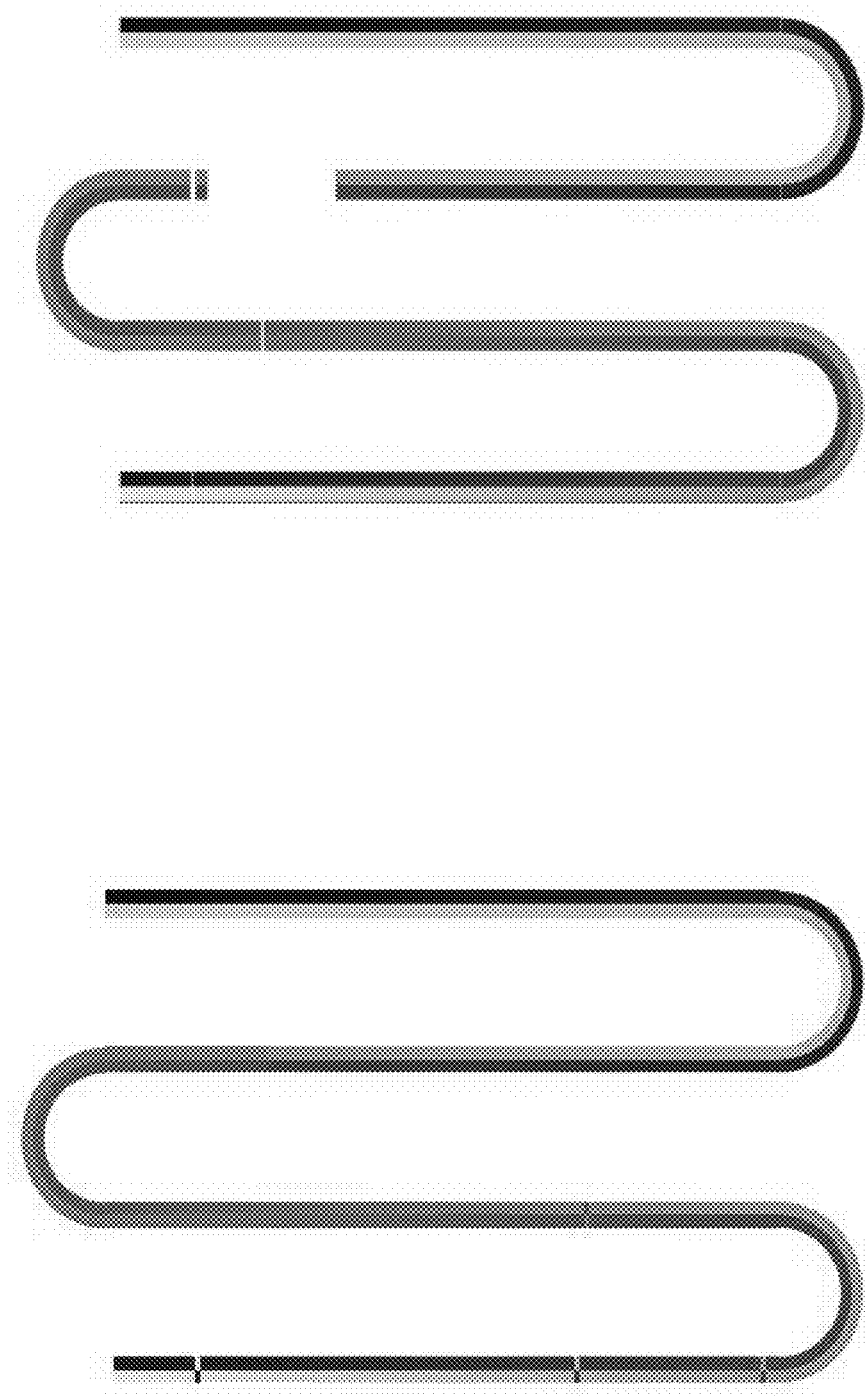
FIG. 2 is a schematic that demonstrates that the disclosed methods can be used to assemble genomes de novo.

One of the other major advances enabled by the methods disclosed herein, is de novo assembly genome. As shown in FIG. 2, the combination of the disclosed methods and high through put sequencing can be used to assemble genomes de novo. The image at top represents the correct assembly of human chromosome 20. At bottom is shown a de novo assembly of human chromosome 20 from 100 kb fragments, created using data generated with the methods disclosed herein. With the exception of a few small inversions, the assembly is perfect. The maps allow the creation of de novo genome assemblies without the use of mate pair reads.

B. In Situ Methods for Detecting Spatial Nucleic Acid Proximity

Disclosed herein are in situ methods for detecting spatial proximity relationships between nucleic acid sequences in a sample, such as DNA sequences, for example in a cell or multiple cells. The methods include providing a sample of one or more cells, nuclear extract, cellular milieu or system of nucleic acids of interest that include nucleic acids. In some embodiments, the spatial relationships in the cell is locked in, for example cross-linked or otherwise stabilized. For example, a sample of cells can be treated with a cross-linker to lock in the spatial information or relationship about the molecules in the cells, such as the DNA in the cell. The nucleic acids present are fragmented to yield nucleic acids with overhanging ends, such as a 5' overhanging end. The overhanging ends are then filled in, for example using a DNA polymerase, such as available from a commercial source. The filled in nucleic acid fragments are thus blunt ended at the end filled 5' end. The fragments are then end joined at the filled in end, for example, by ligation using a commercially available nucleic acid ligase, or otherwise attached to another fragment that is in close physical proximity. The ligation, or other attachment procedure, for example nick translation or strand displacement, creates one or more end joined nucleic acid fragments having a junction, for example a ligation junction, wherein the site of the junction, or at least within a few bases, includes one or more labeled nucleic acids, for example, one or more fragmented nucleic acids that have had their overhanging ends filled and joined together. While this step typically involves a ligase, it is contemplated that any means of joining the fragments can be used, for example any chemical or enzymatic means. Further, it is not necessary that the ends be joined in a typical 3'-5' ligation.

To identify the created ligation junction a labeled nucleotide is used. In one example embodiment, one or more labeled nucleotides are incorporated into the ligated junction. For example, the overhanging ends may be filled in using a DNA polymerase that incorporates one or more labeled nucleotides during the filling in step described above.

In some embodiments the nucleic acids are cross-linked, either directly, or indirectly, and the information about spatial relationships between the different DNA fragments in the cell, or cells, is maintained during this joining step, and substantially all of the end joined nucleic acid fragments formed at this step were in spatial proximity in the cell prior to the crosslinking step. Therefore, at this point the information about which sequences were in spatial proximity to other sequences in the cell is locked into the end joined fragments. It has been found however, that in some situations, it is not necessary to hold the nucleic acids in place using a chemical fixative or crosslinking agent. Thus in some embodiments, no crosslinking agent is used. In still other embodiments, the nucleic acids are held in position relative to each other by the application of non-crosslinking means, such as by using agar or other polymer to hold the nucleic acids in position.

The labeled nucleotide is present in the junction is used to isolate the one or more end joined nucleic acid fragments using the labeled nucleotide. The sequence is determined at the junction of the one or more end joined nucleic acid fragments, thereby detecting spatial proximity relationships between nucleic acid sequences in a cell. In some embodiments, such as for genome assembly, essentially all of the sequence of the end joined fragments is determined. In some embodiments, determining the sequence of the junction of the one or more end joined nucleic acid fragments includes nucleic acid sequencing. In some embodiments, determining the sequence of the junction of the one or more end joined nucleic acid fragments includes using a probe that specifically hybridizes to the nucleic acid sequences both 5' and 3' of the junction of the one or more end joined nucleic acid fragments, for example using an RNA probe, a DNA probe, a locked nucleic acid (LNA) probe, a peptide nucleic acid (PNA) probe, or a hybrid RNA-DNA probe. In exemplary embodiments of the disclosed method, the location is determined or identified for nucleic acid sequences both 5' and 3' of the ligation junction of the one or more end joined nucleic acid fragments relative to source genome and/or chromosome. In some embodiments, the junction identified is correlated with a disease state. In some embodiments, the junction identified is correlated with an environmental condition. In some embodiments, the sequenced end joined fragments are assembled to create an assembled genome or portion thereof, such as a chromosome or sub-fraction thereof. In some embodiments, information from one or more ligation junctions derived from a sample consisting of a mixture of cells from different organisms, such as mixture of microbes, is used to identify the organisms present in the sample and their relative proportions. In some example, the sample is derived from patient samples.

Typically, the end joined fragments are desired to be between about 100 and about 1000 bases in length, although longer and shorter fragments are contemplated. In some embodiments, the nucleic acid fragments are between about 100 and about 1000 bases in length, such as about 100, about 150, about 200, about 250, about 300, about 350, about 400, about 450, about 500, about 550, about 600, about 650, about 700, about 750, about 800, about 850, about 900, about 950 or about 1000 bases in length, for example form about 100 to about 1000, about 200 to about 800, about 500 to about 850, about 100 to about 500 and about 300 to about 775 base pairs in length and the like. In specific examples, end joined fragments are selected for sequence determination that are between about 300 and 500 base pairs in length.

In some embodiments, in order to create discrete portions of nucleic acid that can be joined together in subsequent steps of the methods, the nucleic acids present in the cells, such as cross-linked cells, are fragmented. The fragmentation can be done by a variety of methods, such as enzymatic and chemical cleavage. For example, DNA can be fragmented using an endonuclease that cuts a specific sequence of DNA and leaves behind a DNA fragment with a 5' overhang, thereby yielding fragmented DNA. In other examples an endonuclease can be selected that cuts the DNA at random spots and yields overhangs or blunt ends. In some embodiments, fragmenting the nucleic acid present in the one or more cells comprises enzymatic digestion with an endonuclease that leaves 5' overhanging ends. Enzymes that fragment, or cut, nucleic acids and yield an overhanging sequence are known in the art and can be obtained from such commercial sources as New England BioLabs® and Promega®. One of ordinary skill in the art can choose the restriction enzyme with out undue experimentation. One of ordinary skill in the art will appreciate that using different fragmentation techniques, such as different enzymes with different sequence requirements, will yield different fragmentation patterns and therefore different nucleic acid ends. The process of fragmenting the sample can yield ends that are capable of being joined.

In some embodiments, the end joined DNA that includes a labeled nucleotide is captured with a specific binding agent that specifically binds a capture moiety, such as biotin, on the labeled nucleotide. In some embodiments, the capture moiety is adsorbed or otherwise captured on a surface. In specific embodiments, the end target joined DNA is labeled with biotin, for instance by incorporation of biotin-14-CTP or other biotinylated nucleotide during the filling in of the 5' overhang, for example with a DNA polymerase, allowing capture by streptavidin. Other means for labeling, capturing, and detecting nucleic acid probes include: incorporation of aminoallyl-labeled nucleotides, incorporation of sulfhydryl-labeled nucleotides, incorporation of allyl- or azide-containing nucleotides, and many other methods described in Bioconjugate Techniques ($2^{nd}$ Ed), Greg T. Hermanson, Elsevier (2008), which is specifically incorporated herein by reference. In some embodiments the specific binding agent has been immobilized for example on a solid support, thereby isolating the target nucleic molecule of interest. By "solid support or carrier" is intended any support capable of binding a targeting nucleic acid. Well-known supports or carriers include glass, polystyrene, polypropylene, polyethylene, dextran, nylon, amylases, natural and modified celluloses, polyacrylamides, agarose, gabbros and magnetite. The nature of the carrier can be either soluble to some extent or insoluble for the purposes of the present disclosure. The support material may have virtually any possible structural configuration so long as the coupled molecule is capable of binding to targeting probe. Thus, the support configuration may be spherical, as in a bead, or cylindrical, as in the inside surface of a test tube, or the external surface of a rod. Alternatively, the surface may be flat such as a sheet or test strip. After capture, these end joined nucleic acid fragments are available for further analysis, for example to determine the sequences that contributed to the information encoded by the ligation junction, which can be used to determine which DNA sequences are close in spatial proximity in the cell, for example to map the three dimensional structure of DNA in a cell such as genomic and/or chromatin bound DNA. In some embodiments, the sequence is determined by PCR, hybridization of a probe and/or sequencing, for example by sequencing using high-throughput paired end sequencing. In some embodiments determining the sequence at the one or more junctions of the one or more end joined nucleic acid fragments comprises nucleic acid sequencing, such as short-read sequencing technologies or long-read sequencing technologies. In some embodiments, nucleic acid sequencing is used to determine two or more junctions within an end-joined concatemer simultaneously.

In some embodiments, determining the sequence of a junction includes using a probe that specifically binds to the junction at the site of the two joined nucleic acid fragments. In particular embodiments, the probe specifically hybridizes to the junction both 5' and 3' of the site of the join and spans the site of the join. A probe that specifically binds to the junction at the site of the join can be selected based on known interactions, for example in a diagnostic setting where the presence of a particular target junction, or set of target junctions, has been correlated with a particular disease or condition. It is further contemplated that once a target junction is known, a probe for that target junction can be synthesized.

In some embodiments, the end joined nucleic acids are selectively amplified. In some examples, to selectively amplify the end joined nucleic acids, a 3' DNA adaptor and a 5' RNA, or conversely a 5' DNA adaptor and a 3' RNA adaptor can be ligated to the ends of the molecules can be used to mark the end joined nucleic acids. Using primers specific for these adaptors only end joined nucleic acids will be amplified during an amplification procedure such as PCR. In some embodiments, the target end joined nucleic acid is amplified using primers that specifically hybridize to the adaptor nucleic acid sequences present at the 3' and 5' ends of the end joined nucleic acids. In some embodiments, the non-ligated ends of the nucleic acids are end repaired. In some embodiments attaching sequencing adapters to the ends of the end ligated nucleic acid fragments.

In some embodiments, the cells are lysed to release the cellular contents, for example after crosslinking. In some examples the nuclei are lysed as well, while in other examples, the nuclei are maintained intact, which can then be isolated and optionally lysed, for example using an reagent that selectively targets the nuclei or other separation technique known in the art. In some examples, the sample is a sample of permeablized nuclei, multiple nuclei, isolated nuclei, synchronized cells, (such at various points in the cell cycle, for example metaphase) or acellular. In some embodiments, the nucleic acids present in the sample are purified, for example using ethanol precipitation. In example embodiments of the disclosed method the cells and/or cell nuclei are not subjected to mechanical lysis. In some example embodiments, the sample is not subjected to RNA degradation. In specific embodiments, the sample is not contacted with an exonuclease to remove of biotin from un-ligated ends. In some embodiments, the sample is not subjected to phenol/chloroform extraction.

In some embodiments of the disclosed method the nucleic acids present in the cell or cells are fixed in position relative to each other by chemical crosslinking, for example by contacting the cells with one or more chemical cross linkers. This treatment locks in the spatial relationships between portions of nucleic acids in a cell. Any method of fixing the nucleic acids in their positions can be used. In some embodiments, the cells are fixed, for example with a fixative, such as an aldehyde, for example formaldehyde or gluteraldehyde. In some embodiments, a sample of one or more cells is cross-linked with a cross-linker to maintain the spatial relationships in the cell. For example, a sample of cells can be treated with a cross-linker to lock in the spatial information or relationship about the molecules in the cells, such as the DNA and RNA in the cell. In other embodiments, the relative positions of the nucleic acid can be maintained without using crosslinking agents. For example the nucleic acids can be stabilized using spermine and spermidine (see Cullen et al., Science 261, 203 (1993), which is specifically incorporated herein by reference in its entirety). Other methods of maintaining the positional relationships of nucleic acids are known in the art. In some embodiments, nuclei are stabilized by embedding in a polymer such as agarose. In some embodiments, the cross-linker is a reversible cross-linker. In some embodiments, the cross-linker is reversed, for example after the fragments are joined. In specific examples, the nucleic acids are released from the cross-linked three-dimensional matrix by treatment with an agent, such as a proteinase, that degrade the proteinaceous material form the sample, thereby releasing the end ligated nucleic acids for further analysis, such as determination of the nucleic acid sequence. In specific embodiments, the sample is contacted with a proteinase, such as Proteinase K.

In some embodiments of the disclosed methods, the cells are contacted with a crosslinking agent to provide the cross-linked cells. In some examples, the cells are contacted with a protein-nucleic acid crosslinking agent, a nucleic acid-nucleic acid crosslinking agent, a protein-protein crosslinking agent or any combination thereof. By this method, the nucleic acids present in the sample become resistant to special rearrangement and the spatial information about the relative locations of nucleic acids in the cell is maintained. In some examples, a cross-linker is a reversible-, such that the cross-linked molecules can be easily separated in subsequent steps of the method. In some examples, a cross-linker is a non-reversible cross-linker, such that the cross-linked molecules cannot be easily separated. In some examples, a cross-linker is light, such as UV light. In some examples, a cross linker is light activated. These cross-linkers include formaldehyde, disuccinimidyl glutarate, UV light, psoralens and their derivatives such as aminomethyltrioxsalen, glutaraldehyde, ethylene glycol bis[succinimidylsuccinate], bissulfosuccinimidyl suberate, 1-Ethyl-3-[3-dimethylaminopropyl]carbodiimide (EDC) bis[sulfosuccinimidyl] suberate ($BS^3$) and other compounds known to those skilled in the art, including those described in the *Thermo Scientific Pierce Crosslinking Technical Handbook*, Thermo Scientific (2009) as available on the world wide web at piercenet.com/files/1601673_Crosslink_HB_Intl.pdf.

The disclosed methods are also particularly suited to monitoring disease states, such as disease state in an organism, for example a plant or an animal subject, such as a mammalian subject, for example a human subject. Certain disease states may be caused and/or characterized by the differential formation of certain target joins. For example, certain interactions may occur in a diseased cell but not in a normal cell. In other examples, certain interactions may occur in a normal cell but not in diseased cell. Thus, using the disclosed methods a profile of the interaction between DNA sequences in vivo, can be correlated with a disease state. The target join profile correlated with a disease can be used as a "fingerprint" to identify and/or diagnose a disease in a cell, by virtue of having a similar "fingerprint." In addition, the profile can be used to monitor a disease state, for example to monitor the response to a therapy, disease progression and/or make treatment decisions for subjects.

The ability to obtain an interaction profile allows for the diagnosis of a disease state, for example by comparison of the profile present in a sample with the correlated with a specific disease state, wherein a similarity in profile indicates a particular disease state.

Accordingly, aspects of the disclosed methods relate to diagnosing a disease state based on target junction profile correlated with a disease state, for example cancer, or an infection, such as a viral or bacterial infection. It is understood that a diagnosis of a disease state could be made for any organism, including without limitation plants, and animals, such as humans.

Aspects of the present disclosure relate to the correlation of an environmental stress or state with an target junction profile, such as a sample of cells, for example a culture of cells, can be exposed to an environmental stress, such as but not limited to heat shock, osmolarity, hypoxia, cold, oxidative stress, radiation, starvation, a chemical (for example a therapeutic agent or potential therapeutic agent) and the like. After the stress is applied, a representative sample can be subjected to analysis, for example at various time points, and compared to a control, such as a sample from an organism or cell, for example a cell from an organism, or a standard value.

In some embodiments, the disclosed methods can be used to screen chemical libraries for agents that modulate DNA interaction profiles, for example that alter the interaction profile from an abnormal one, for example correlated to a disease state to one indicative of a disease free state. By exposing cells, or fractions thereof, tissues, or even whole animals, to different members of the chemical libraries, and performing the methods described herein, different members of a chemical library can be screened for their effect on interaction profiles simultaneously in a relatively short amount of time, for example using a high throughput method.

In some embodiments, the sequence information determined by the disclosed methods may be used to phase polymorphisms and/or assemble individual haplotypes, distinguish between heterozygous and homozygous structural variations, resolve genomic structural genomic variation, including copy number variations, estimate the 1D distance between two fragments of DNA from the same chromosome, assess syntenic relationships between two or more organisms at arbitrary resolution, and/or generate phylogenetic trees and/or ancestral genomes.

In some embodiments, screening of test agents involves testing a combinatorial library containing a large number of potential modulator compounds. A combinatorial chemical library may be a collection of diverse chemical compounds generated by either chemical synthesis or biological synthesis, by combining a number of chemical "building blocks" such as reagents. For example, a linear combinatorial chemical library, such as a polypeptide library, is formed by combining a set of chemical building blocks (amino acids) in every possible way for a given compound length (for example the number of amino acids in a polypeptide compound). Millions of chemical compounds can be synthesized through such combinatorial mixing of chemical building blocks.

Appropriate agents can be contained in libraries, for example, synthetic or natural compounds in a combinatorial library. Numerous libraries are commercially available or can be readily produced; means for random and directed synthesis of a wide variety of organic compounds and biomolecules, including expression of randomized oligonucleotides, such as antisense oligonucleotides and oligopeptides, also are known. Alternatively, libraries of natural compounds in the form of bacterial, fungal, plant and animal extracts are available or can be readily produced. Additionally, natural or synthetically produced libraries and compounds are readily modified through conventional chemical, physical and biochemical means, and may be used to produce combinatorial libraries. Such libraries are useful for the screening of a large number of different compounds.

The compounds identified using the methods disclosed herein can serve as conventional "lead compounds" or can themselves be used as potential or actual therapeutics. In some instances, pools of candidate agents can be identified and further screened to determine which individual or subpools of agents in the collective have a desired activity.

Appropriate samples for use in the methods disclosed herein include any conventional biological sample obtained from an organism or a part thereof, such as a plant, animal, and the like. In particular embodiments, the biological sample is obtained from an animal subject, such as a human subject. A biological sample is any solid or fluid sample obtained from, excreted by or secreted by any living organism, including without limitation, single celled organisms, such as yeast, protozoans, and amoebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease, such as a rheumatoid arthritis, osteoarthritis, gout or septic arthritis). A sample can also be a sample obtained from any organ or tissue (including a biopsy or autopsy specimen, such as a tumor biopsy) or can include a cell (whether a primary cell or cultured cell) or medium conditioned by any cell, tissue or organ. Exemplary samples include, without limitation, cells, cell lysates, blood smears, cyto-centrifuge preparations, cytology smears, bodily fluids (e.g., blood, plasma, serum, saliva, sputum, urine, bronchoalveolar lavage, semen, etc.), tissue biopsies (e.g., tumor biopsies), fine-needle aspirates, and/or tissue sections (e.g., cryostat tissue sections and/or paraffin-embedded tissue sections). In other examples, the sample includes circulating tumor cells (which can be identified by cell surface markers). In particular examples, samples are used directly (e.g., fresh or frozen), or can be manipulated prior to use, for example, by fixation (e.g., using formalin) and/or embedding in wax (such as formalin-fixed paraffin-embedded (FFPE) tissue samples). It will appreciated that any method of obtaining tissue from a subject can be utilized, and that the selection of the method used will depend upon various factors such as the type of tissue, age of the subject, or procedures available to the practitioner. Standard techniques for acquisition of such samples are available. See, for example Schluger et al., *J. Exp. Med.* 176:1327-33 (1992); Bigby et al., *Am. Rev. Respir. Dis.* 133:515-18 (1986); Kovacs et al., *NEJM* 318: 589-93 (1988); and Ognibene et al., *Am. Rev. Respir. Dis.* 129:929-32 (1984).

This disclosure also provides integrated systems for high-throughput testing, or automated testing. The systems typically include a robotic armature that transfers fluid from a source to a destination, a controller that controls the robotic armature, a detector, a data storage unit that records detection, and an assay component such as a microtiter dish comprising a well having a reaction mixture for example media.

In some embodiments of the disclosed methods, determining the identity of a nucleic acid, such as a target junction, includes detection by nucleic acid hybridization. Nucleic acid hybridization involves providing a probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, PNA:DNA, RNA:RNA, or RNA:DNA) will form even where the annealed sequences are not perfectly complementary. Thus, specificity of hybridization is reduced at lower stringency. Conversely, at higher stringency (e.g., higher temperature or lower salt) successful hybridization requires fewer mismatches. One of skill in the art will appreciate that hybridization conditions can be designed to provide different degrees of stringency.

In general, there is a tradeoff between hybridization specificity (stringency) and signal intensity. Thus, in one embodiment, the wash is performed at the highest stringency that produces consistent results and that provides a signal intensity greater than approximately 10% of the background intensity. Thus, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest. In some examples, RNA is detected using Northern blotting or in situ hybridization (Parker & Barnes, *Methods in Molecular Biology* 106:247-283, 1999); RNAse protection assays (Hod, *Biotechniques* 13:852-4, 1992); and PCR-based methods, such as reverse transcription polymerase chain reaction (RT-PCR) (Weis et al., *Trends in Genetics* 8:263-4, 1992).

In one embodiment, the hybridized nucleic acids are detected by detecting one or more labels attached to the sample nucleic acids. The labels can be incorporated by any of a number of methods. In one example, the label is simultaneously incorporated during the amplification step in the preparation of the sample nucleic acids. Thus, for example, polymerase chain reaction (PCR) with labeled primers or labeled nucleotides will provide a labeled amplification product. In one embodiment, transcription amplification, as described above, using a labeled nucleotide (such as fluorescein-labeled UTP and/or CTP) incorporates a label into the transcribed nucleic acids.

Detectable labels suitable for use include any composition detectable by spectroscopic, photochemical, biochemical, immunochemical, electrical, optical or chemical means. Useful labels include biotin for staining with labeled streptavidin conjugate, magnetic beads (for example DYNABEADS™), fluorescent dyes (for example, fluorescein, Texas red, rhodamine, green fluorescent protein, and the like), radiolabels (for example, $^3$H, $^{125}$I, $^{35}$S, $^{14}$C, or $^{32}$P), enzymes (for example, horseradish peroxidase, alkaline phosphatase and others commonly used in an ELISA), and colorimetric labels such as colloidal gold or colored glass or plastic (for example, polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are also well known. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The label may be added to the target (sample) nucleic acid(s) prior to, or after, the hybridization. So-called "direct labels" are detectable labels that are directly attached to or incorporated into the target (sample) nucleic acid prior to hybridization. In contrast, so-called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected (see *Laboratory Techniques in Biochemistry and Molecular Biology*, Vol. 24: *Hybridization With Nucleic Acid Probes*, P. Tijssen, ed. Elsevier, N.Y., 1993).

In some embodiments, the identity of a nucleic acid is determined by DNA or RNA sequencing. Generally, the sequencing can be performed using automated Sanger sequencing (AB13730x1 genome analyzer), pyrosequencing on a solid support (454 sequencing, Roche), sequencing-by-synthesis with reversible terminations (ILLUMINA® Genome Analyzer), sequencing-by-ligation (ABI SOLiD®) or sequencing-by-synthesis with virtual terminators (HELISCOPE®); Moleculo sequencing (see Voskoboynik et al. eLife 2013 2:e00569 and U.S. patent application Ser. No. 13/608,778, filed Sep. 10, 2012 and issued as U.S. Pat. No. 9,249,460); DNA nanoball sequencing; Single molecule real time (SMRT) sequencing; Nanopore DNA sequencing; Sequencing by hybridization; Sequencing with mass spectrometry; and Microfluidic Sanger sequencing. Examples of information that can be obtained from the disclosed methods and the analysis of the results thereof, include without limitation uni- or multiplex, 3 dimensional genome mapping, genome assembly, one dimensional genome mapping, the use of single nucleotide polymorphisms to phase genome maps, for example to determine the patterns of chromosome inactivation, such as for analysis of genomic imprinting, the use of specific junctions to determine karyotypes, including but not limited to chromosome number alterations (such as unisomies, uniparental disomies, and trisomies), translocations, inversions, duplications, deletions and other chromosomal rearrangements, the use of specific junctions correlated with disease to aid in diagnosis.

Furthermore, the methods disclosed herein can readily be combined with other techniques, such as hybrid capture after library generation (to target specific parts of the genome), chromatin immunoprecipitation after ligation (to examine the chromatin environment of regions associated with specific proteins), bisulfite treatment, (to probe the methylation state of DNA). For examples the information from one or more ligation junctions is used to infer and/or determine the three dimensional structure of the genome. In some embodiments, the information from one or more ligation junctions is used to simultaneously map protein-DNA interactions and DNA-DNA interactions or RNA-DNA interactions and DNA-DNA interactions. In some embodiments, the information from one or more ligation junctions is used to simultaneously map methylation and three-dimensional structure. In some embodiments, the information from more than one ligation junction is used to assemble whole genomes or parts of genomes. In some embodiments, the sample is treated to accentuate interactions between contiguous regions of the genome. In some embodiments, the cells in the sample are synchronized in metaphase.

In one example embodiment, hybrid capture after library generation comprises treating a library of end joined nucleic acid fragments generated using the methods described above with an agent that isolates end joined nucleic acid fragments comprising specific nucleic acid sequence (target sequence). In certain example embodiments, the specific nucleic acid sequence is at least 50, at least 60, at least 70, at least 80, at least 90, at least 100, at least 110, at least 120, at least 130, at least 140, at least 150, at least 160, at least 170, at least 180, at least 190, or at least 200 base pairs long. In certain example embodiments, the specific nucleic acid sequence is within at least 50, at least 60, at least 70, at least, 80, at least 90, or at least 100 base pairs, in either the 5' or 3' direction, of a restriction site. In certain example embodiments, the specific nucleic sequence comprises less than ten repetitive bases. In certain other example embodiments, the GC content of the specific nucleic acid sequence is between 25% and 80%, between 40% and 70%, or between 50% and 60%.

In certain example embodiments, the agent that isolates the end joined nucleic acid fragments comprising the specific nucleic acid sequence is a probe. The probe may be labeled. In certain example embodiments, the probe is radiolabeled, fluorescently-labeled, enzymatically-labeled, or chemically labeled. In certain other example embodiments, the probe may be labeled with a capture moiety, such as a biotin-label. Wherein, the probe is labeled with a capture moiety, the capture moiety may be used to isolate the end joined nucleic acid fragments using techniques such as those known in the art and described previously. The exact sequence of the isolated end-joined nucleic acid fragments may then be determined, for example, by sequencing as described previously.

Considering the wealth of information that can be gained using the methods described herein, with respect to genome architecture at the primary, secondary, tertiary and beyond (see Examples below), the methods disclosed herein can be used to apply genome engineering techniques for the treatment of disease as well as the study of biological questions. In some embodiments, the organizational structure of a genome is determined using the methods disclosed herein. For example the methods disclosed herein have been demonstrated (see Example 1) to generate very dense contact maps. In some examples sequences obtained using the methods disclosed herein are mapped to a genome of an organism, such as a animal, plant, fungi, or microorganism, for example a bacterial, yeast, virus and the like. In some examples, using single nucleotide polymorphisms (SNPs), diploid maps corresponding to each chromosomal homolog are constructed. These maps, as well as others that can be generated using the disclosed technology provide a picture, such as a three-dimensional picture, of genomic architecture with high resolution, such as a resolution of 1 kilobase or even lower, for example less then 500 bases.

As disclosed herein, the inventors have shown that a genome is partitioned into domains that are associated with particular patterns of histone marks that segregates into sub-compartments, distinguished by unique long-range contact patterns. Using the maps, the inventors have identified ~10,000 distinct loops across the genome and studied their properties, including their strong association with gene activation. Using the maps constructed with the methods described herein as a starting place, targeted alterations in genome structure can be made. Such genetic and epigenetic control of cells with genome engineering technologies enables a broad range of applications from basic biology to biotechnology and medicine. Manipulating transcriptional regulation or chromatin states at particular loci can reveal how genetic material is organized and utilized within a cell, illuminating relationships between the architecture of the genome and its functions. In addition, once the organization is determined, for example using the methods disclosed herein, manipulation of the genome can be used as a treatment for certain diseases as well as reconstruction of useful biological systems, for example for drug development processes and medical therapeutics. A series of programmable nuclease-based genome editing technologies have developed (see Hsu et al., Cell 157, Jun. 5, 2014 1262-1278 for review). Among these, the CRISPR/CAS9 system offers incredible promise (see e.g. Platt et al., Cell 159(2), 440-455 (2014); Shalem et al., Science 3 84-87 (2014); and Le Cong et al., Science 339, 819 (2013))

Disclosed herein are methods of altering or modulating the spatial proximity relationships between nucleic acids inside a cell. The methods include providing a sample of one or more cells comprising nucleic acids and providing one or more agents targeting one or more specific genomic regions of interest. The agents are introduced into the one or more cells in order to introduce or remove a sequence or nucleic acid/histone modification associated with a particular spatial proximity arrangement of nucleic acids. In some embodiments the genomic regions of interest are identified with the methods disclosed herein. In some embodiments, a particular sequence is deleted/inserted in order to abrogate/establish a chromatin loop. In some embodiments, the chromatin loop is altered in a tissue specific manner. In some embodiments, the chromatin loop is involved in the regulation of the expression of a gene. In some embodiments, the chromatin loop or specific genomic regions participating in the chromatin loop are indicative of a disease or condition. In some embodiments, a particular sequence is deleted/inserted in order to abrogate/establish a chromatin domain with elevated contacts between all pairs of loci within a contiguous interval. In some embodiments, the chromatin domain is altered in a tissue specific manner. In some embodiments, the chromatin domain is involved in the regulation of the expression of a gene. In some embodiments, the chromatin domain or specific genomic regions participating in the chromatin domain are indicative of a disease or condition. In some embodiments, an agent is introduced to alter the histone modifications at a specific genomic region. In some embodiments, specific histone modifications are introduced at genomic region to target the region to a nuclear compartment. In some embodiments, the agent introduced to target specific genomic regions is CRISPR/CAS9.

Also disclosed is a system wherein information from one or more ligation junctions is used to identify regions of the genome that control or modulate spatial proximity relationships between nucleic acids. In some embodiments, the genomic regions identified establish chromatin loops. In some embodiments, the genomic regions identified demarcate or establish contiguous intervals of chromatin that display elevated proximity between loci within the intervals.

Further disclosed is a system for visualizing, such as system comprising hardware and/or software, the information from one or more ligation junctions. In some examples, the information from one or more ligation junctions is represented in a matrix with entries indicating frequency of interaction. In some examples, a user can dynamically zoom in and out, viewing interactions between smaller or larger pieces of the genome. In some examples, interaction matrices and other 1-D data vectors can be viewed and compared simultaneously. In some examples, the annotations of features can be superimposed on interaction matrices. In some examples, multiple interaction matrices can be simultaneously viewer and compared.

C. Target Ligation Junctions and Probes

Also disclosed are nucleic acids made of two or more end joined nucleic acids, target junctions, produced using the disclosed methods and amplification products thereof, such as RNA, DNA or a combination thereof. An isolated target junction is an end joined nucleic acid, wherein the junction encodes the information about the proximity of the two nucleic acid sequences that make up the target junction in a cell, for example as formed by the methods disclosed herein. The presence of an isolated target junction can be correlated with a disease state or environmental condition. For example, certain disease states may be caused and/or characterized by the differential formation of certain target junctions. Similarly isolated target junction can be correlated to an environmental stress or state, such as but not limited to heat shock, osmolarity, hypoxia, cold, oxidative stress, radiation, starvation, a chemical (for example a therapeutic agent or potential therapeutic agent) and the like.

This disclosure also relates, to isolated nucleic acid probes that specifically bind to target junction, such as a target junction indicative of a disease state or environmental condition. To recognize a target join, a probe specifically hybridizes to the target junction both 5' and 3' of the site of the junction and spans the site of the target junction, or specifically hybridizes to specific target sequence with the end joined nucleic acid fragments. In some example embodiments, the specific target sequence is at least 50, at least 60, at least 70, at least 80, at least 90, at least 100, at least 110, at least 120, at least 130, at least 140, at least 150, at least 160, at least 170, at least 180, at least 190, or at least 200 base pairs long. In certain example embodiments, the specific nucleic acid sequence is within at least 50, at least 60, at least 70, at least, 80, at least 90, or at least 100 base pairs, in either the 5' or 3' direction, of a restriction site. In certain example embodiments, the specific nucleic sequence comprises less than ten repetitive bases. In certain other example embodiments, the GC content of the specific nucleic acid sequence is between 25% and 80%, between 40% and 70%, or between 50% and 60%.

In some embodiments, the probe is labeled, such as radiolabeled, fluorescently-labeled, biotin-labeled, enzymatically-labeled, or chemically-labeled. Non-limiting examples of the probe is an RNA probe, a DNA probe, a locked nucleic acid (LNA) probe, a peptide nucleic acid (PNA) probe, or a hybrid RNA-DNA probe. Also disclosed are sets of probes for binding to target ligation junction, as well as devices, such as nucleic acid arrays for detecting a target junction.

In embodiments, the total length of the probe, including end linked PCR or other tags, is between about 10 nucleotides and 200 nucleotides, although longer probes are contemplated. In some embodiments, the total length of the probe, including end linked PCR or other tags, is at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190 191, 192, 193, 194, 195, 196, 197, 198, 199 or 200.

In some embodiments the total length of the probe, including end linked PCR or other tags, is less then about 2000 nucleotides in length, such as less than about 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 500, 750, 1000, 1250, 1500, 1750, 2000 nucleotides in length or even greater. In some embodiments, the total length of the probe, including end linked PCR or other tags, is between about 30 nucleotides and about 250 nucleotides, for example about 90 to about 180, about 120 to about 200, about 150 to about 220 or about 120 to about 180 nucleotides in length. In some embodiments, a set of probes is used to target a specific target junction or a set of target junctions.

In some embodiments, the probe is detectably labeled, either with an isotopic or non-isotopic label, alternatively the target junction or amplification product thereof is labeled. Non-isotopic labels can, for instance, comprise a fluorescent or luminescent molecule, biotin, an enzyme or enzyme substrate or a chemical. Such labels are preferentially chosen such that the hybridization of the probe with target junction can be detected. In some examples, the probe is labeled with a fluorophore. Examples of suitable fluorophore labels are given above. In some examples, the fluorophore is a donor fluorophore. In other examples, the fluorophore is an accepter fluorophore, such as a fluorescence quencher. In some examples, the probe includes both a donor fluorophore and an accepter fluorophore. Appropriate donor/acceptor fluorophore pairs can be selected using routine methods. In one example, the donor emission wavelength is one that can significantly excite the acceptor, thereby generating a detectable emission from the acceptor.

An array containing a plurality of heterogeneous probes for the detection of target junctions are disclosed. Such arrays may be used to rapidly detect and/or identify the target junctions present in a sample, for example as part of a diagnosis. Arrays are arrangements of addressable locations on a substrate, with each address containing a nucleic acid, such as a probe. In some embodiments, each address corresponds to a single type or class of nucleic acid, such as a single probe, though a particular nucleic acid may be redundantly contained at multiple addresses. A "microarray" is a miniaturized array requiring microscopic examination for detection of hybridization. Larger "macroarrays" allow each address to be recognizable by the naked human eye and, in some embodiments, a hybridization signal is detectable without additional magnification. The addresses may be labeled, keyed to a separate guide, or otherwise identified by location.

Any sample potentially containing, or even suspected of containing, target joins may be used. A hybridization signal from an individual address on the array indicates that the probe hybridizes to a nucleotide within the sample. This system permits the simultaneous analysis of a sample by plural probes and yields information identifying the target junctions contained within the sample. In alternative embodiments, the array contains target junctions and the array is contacted with a sample containing a probe. In any such embodiment, either the probe or the target junction may be labeled to facilitate detection of hybridization.

Within an array, each arrayed nucleic acid is addressable, such that its location may be reliably and consistently determined within the at least the two dimensions of the array surface. Thus, ordered arrays allow assignment of the location of each nucleic acid at the time it is placed within the array. Usually, an array map or key is provided to correlate each address with the appropriate nucleic acid. Ordered arrays are often arranged in a symmetrical grid pattern, but nucleic acids could be arranged in other patterns (for example, in radially distributed lines, a "spokes and wheel" pattern, or ordered clusters). Addressable arrays can be computer readable; a computer can be programmed to correlate a particular address on the array with information about the sample at that position, such as hybridization or binding data, including signal intensity. In some exemplary computer readable formats, the individual samples or molecules in the array are arranged regularly (for example, in a Cartesian grid pattern), which can be correlated to address information by a computer.

An address within the array may be of any suitable shape and size. In some embodiments, the nucleic acids are suspended in a liquid medium and contained within square or rectangular wells on the array substrate. However, the nucleic acids may be contained in regions that are essentially triangular, oval, circular, or irregular. The overall shape of the array itself also may vary, though in some embodiments it is substantially flat and rectangular or square in shape.

Examples of substrates for the phage arrays disclosed herein include glass (e.g., functionalized glass), Si, Ge, GaAs, GaP, $SiO_2$, $SiN_4$, modified silicon nitrocellulose, polyvinylidene fluoride, polystyrene, polytetrafluoroethylene, polycarbonate, nylon, fiber, or combinations thereof. Array substrates can be stiff and relatively inflexible (for example glass or a supported membrane) or flexible (such as a polymer membrane). One commercially available product line suitable for probe arrays described herein is the Microlite line of MICROTITER® plates available from Dynex Technologies UK (Middlesex, United Kingdom), such as the Microlite 1+ 96-well plate, or the 384 Microlite+384-well plate.

Addresses on the array should be discrete, in that hybridization signals from individual addresses can be distinguished from signals of neighboring addresses, either by the naked eye (macroarrays) or by scanning or reading by a piece of equipment or with the assistance of a microscope (microarrays).

D. Kits

The nucleic acid probes, such as probes for specifically binding to a target junction, and other reagents disclosed herein for use in the disclosed methods can be supplied in the form of a kit. In such a kit, an appropriate amount of one or more of the nucleic acid probes is provided in one or more containers or held on a substrate. A nucleic acid probe may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, ampoules, or bottles. The kits can include either labeled or unlabeled nucleic acid probes for use in detection, of a target junction.

The amount of nucleic acid probe supplied in the kit can be any appropriate amount, and may depend on the target market to which the product is directed. A kit may contain more than one different probe, such as 2, 3, 4, 5, 6, 7, 8, 9, 10, 11, 12, 13, 14, 15, 20, 25, 50, 100, or more probes. The instructions may include directions for obtaining a sample, processing the sample, preparing the probes, and/or contacting each probe with an aliquot of the sample. In certain embodiments, the kit includes an apparatus for separating the different probes, such as individual containers (for example, microtubules) or an array substrate (such as, a 96-well or 384-well microtiter plate). In particular embodiments, the kit includes prepackaged probes, such as probes suspended in suitable medium in individual containers (for example, individually sealed EPPENDORF® tubes) or the wells of an array substrate (for example, a 96-well microtiter plate sealed with a protective plastic film). In some embodiments, kits also may include the reagents necessary to carry out methods disclosed herein. In other particular embodiments, the kit includes equipment, reagents, and instructions for the methods disclosed herein.

The following examples are provided to illustrate certain particular features and/or embodiments. These examples should not be construed to limit the invention to the particular features or embodiments described.

EXAMPLES

Example 1

The inventors used the disclosed methods, termed situ Hi-C (an improved method for probing the three-dimensional architecture of Genomes) to construct haploid and diploid maps of nine cell types. The densest, in human lymphoblastoid cells, contains 4.9 billion contacts, achieving 1-kilobase resolution. The inventors found that genomes are partitioned into local domains, which are associated with distinct patterns of histone marks and segregate into six sub-compartments. The inventors identified ~10,000 loops. These loops frequently link promoters and enhancers, correlate with gene activation, and show conservation across cell types and species. Loop anchors typically occur at domain boundaries and bind CTCF. CTCF sites at loop anchors occur predominantly (>90%) in a convergent orientation, with the asymmetric motifs 'facing' one another. The inactive Xchromosome splits into two massive domains and contains large loops anchored at CTCF-binding repeats.

The spatial organization of the human genome is known to play an important role in the transcriptional control of genes (Bickmore, Annual review of genomics and human genetics 14, 67-84, 2013; Cremer and Cremer, Nature Rev Genet 2, 292-301, 2001; Sexton et al., Nature structural & molecular biology 14, 1049-1055, 2007). Yet important questions remain, like how distal regulatory elements, such as enhancers, affect promoters and how insulators can abrogate these effects (Banerji et al., Cell 27, 299-308, 1981; Blackwood and Kadonaga, Science (New York, N.Y.) 281, 60-63, 1998; Gaszner and Felsenfeld, Nature Reviews: Genetics 7, 703-713, 2006). Both phenomena are thought to involve the formation of protein-mediated "loops" that bring pairs of genomic sites that lie far apart along the linear genome into proximity (Schleif, Annual review of biochemistry 61, 199-223, 1992).

Over the past quarter-century, various methods have emerged to assess the three-dimensional architecture of the nucleus in vivo (Gerasimova et al., Molecular cell 6, 1025-1035, 2000; Mukherjee et al., Cell 52, 375-383, 1988), including nuclear ligation assay and chromosome conformation capture (3C), which analyze contacts made by a single locus (Cullen et al., Science 261, 203-206, 1993; Dekker et al., Science 295, 1306-1311, 2002; Murrell et al., Nature genetics 36, 889-893, 2004; Tolhuis et al., Molecular cell 10, 1453-1465, 2002), extensions such as 5C for examining several loci simultaneously (Dostie et al., Genome research 16, 1299-1309, 2006), and methods such as CHIA-PET for examining all loci bound by a specific protein (Fullwood et al., Nature 462, 58-64, 2009). The inventors had previously developed Hi-C, which combines DNA-DNA proximity ligation with highthroughput sequencing to interrogate all pairs of loci across a genome (Lieberman-Aiden et al., Science 326, 289-293, 2009).

Disclosed herein is a new and unique method, dubbed in situ Hi-C, in which proximity ligation is performed in intact nuclei. The protocol facilitates generation of much denser Hi-C maps. The maps reported here comprise 5 terabases of sequence data recording over 15 billion contacts; they are larger, by an order of magnitude, than all published Hi-C datasets combined. Using single nucleotide polymorphisms (SNPs), we also construct diploid maps corresponding to each chromosomal homolog. The maps provide a picture of genomic architecture with resolution down to 1 kilobase. They show that the genome is partitioned into domains that are associated with particular patterns of histone marks and that segregate into six sub-compartments, distinguished by unique longrange contact patterns. Using the maps, the inventors have identified ~10,000 distinct loops across the genome and study their properties, including their strong association with gene activation. Strikingly, the vast majority of loop anchors bind CTCF. Moreover, the two CTCF motifs that occur at the anchors of a loop are found in a convergent orientation—that is, with the asymmetric CTCF motifs 'facing' one another—over 90% of the time. The diploid maps show that the inactive Xchromosome is partitioned into two massive domains, and contains large loops anchored at CTCF-binding repeats.

Results

In Situ Hi-C Methodology and Maps

Figure 3A:
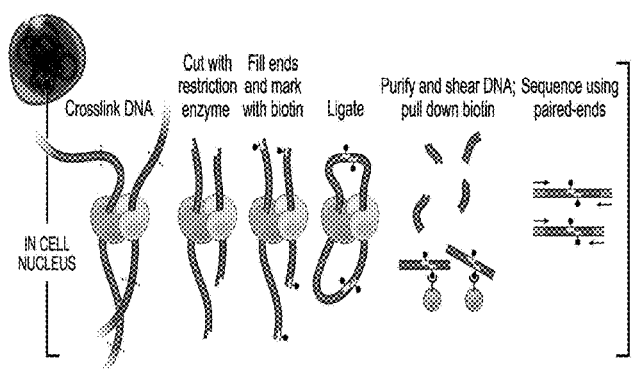
FIG. 3. In situ Hi-C was used to map over 15 billion chromatin contacts across nine cell types in human and mouse, achieving 1 kilobase resolution in human lymphoblastoid cells. (A) During in situ Hi-C, DNA-DNA proximity ligation is performed in intact nuclei. (B) Contact matrices from chromosome 14: the whole chromosome, at 500 Kb resolution (top); 86-96 Mb/50 Kb resolution (middle); 94-95 Mb/5 Kb resolution (bottom). Left: GM12878, primary experiment; Right: replicate. The 1D regions corresponding to a contact matrix are indicated in the diagrams above and at left. The intensity of each pixel represents the normalized number of contacts between a pair of loci. Maximum intensity is indicated in the lower left of each panel. (C) Is a comparison in situ HI-C++ generated map of chromosome 7 in GM12878 (last column) to earlier Hi-C maps: Lieberman-Aiden et al., Science 326, 289-293, 2009; Kalhor et al., Nature biotechnology 30, 90-98, 2012, and Jin et al., Nature. 503(7475), 290-4, 2013 (D) Mean contacts per pixel vs distance, at various resolutions, compared to published Hi-C experiments (dashed line=10).
Figure 3B:
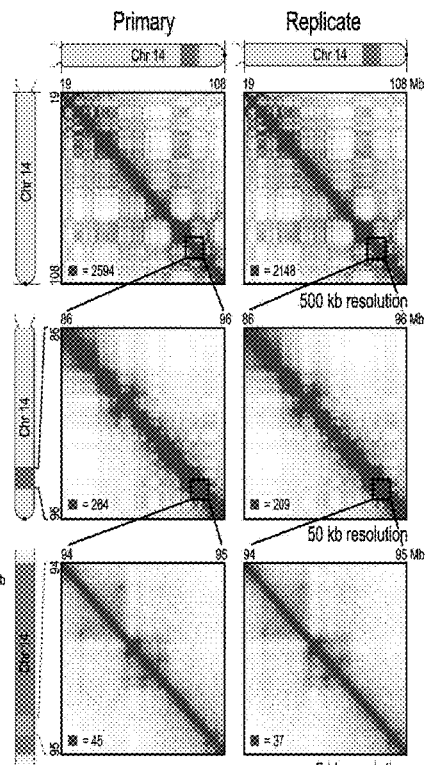

As implemented in this Example, the disclosed in situ Hi-C protocol involves cross-linking cells with formaldehyde; permeabilizing them with nuclei intact; digesting DNA with a suitable 4-cutter restriction enzyme (such as MboI); filling the 5'-overhangs while incorporating a biotinylated nucleotide; ligating the resulting blunt-end fragments; shearing the DNA; capturing the biotinylated ligation junctions with streptavidin beads; and analyzing the resulting fragments with paired-end sequencing (FIG. 3A).

The protocol has three major advantages over the original Hi-C protocol (here called dilution Hi-C). First, in situ ligation reduces the frequency of spurious contacts due to random ligation in dilute solution—as evidenced by a lower frequency of junctions between mitochondrial and nuclear DNA. Second, the protocol is much faster, requiring three days instead of seven. Third, it enables higher resolution and more efficient cutting of chromatinized DNA, for instance, through the use of a 4-cutter (MboI) rather than a 6-cutter (typically, HindIII).

A Hi-C map is a list of DNA-DNA contacts produced by a Hi-C experiment. By partitioning the linear genome into "loci" of fixed size (e.g., bins of 1 Mb or 1 Kb), the Hi-C map can be represented as a "contact matrix" M, where the entry $M_{i,j}$ is the number of contacts observed between locus $L_i$ and locus $L_j$. (A "contact" is a read pair that remains after we exclude reads that do not align uniquely to the genome, that correspond to unligated fragments, or that are duplicates.) The contact matrix can be visualized as a heatmap, whose entries are called "pixels". An "interval" refers to a (one-dimensional) set of consecutive loci; the contacts between two intervals thus form a "rectangle" or "square" in the contact matrix. "Matrix resolution" is defined as the locus size used to construct a particular contact matrix and "map resolution" as the smallest locus size such that 80% of loci have at least 1000 contacts. The map resolution describes the finest scale at which one can reliably discern local features in the data.

Contact Maps Spanning 9 Cell Lines Containing Over 15 Billion Contacts.

The inventors constructed in situ Hi-C maps of 9 cell lines in human and mouse. Whereas the original Hi-C experiments had a map resolution of 1 Mb, these maps have a resolution of 1 Kb or 5 Kb, demonstrating the surprising improvement. The largest map, in human GM12878 B-lymphoblastoid cells, aggregates the results of nine biological replicate experiments derived from independent cell cultures. It contains 4.9 billion pairwise contacts and has map resolution of 950 bp ("kilobase resolution"). This map was used to construct contact matrices with locus sizes ranging from 2.5 Mb to 1 Kb. The inventors also generated eight in situ Hi-C maps at 5 kb resolution, using cell lines representing all human germ layers (IMR90, HMEC, NHEK, K562, HUVEC, HeLa, and KBM7) as well as mouse Blymphoblasts (CH12-LX). Each of these maps contains between 395M and 1.1B contacts. To test reproducibility, a comparison was made of "primary" GM12878 map (2.6 billion contacts from a single culture) to a "replicate" map (2.3 billion contacts aggregated from experiments on eight other samples). The results were strongly correlated both visually and statistically (Pearson's R>0.998, 0.996, 0.96 and 0.85 at matrix resolutions of 500, 50, 5, and 1 Kb; P-values throughout are negligible unless stated) (FIG. 1B-D). Biological replicates were compared in IMR90, HMEC, K562, KBM7, and CH12-LX with similar results. To ensure that the results were comparable with those of previous Hi-C experiments, an original dilution Hi-C protocol was used to generate a map of GM12878 with 3.2 billion contacts; the in situ and dilution Hi-C showed high reproducibility (R>0.96, 0.90, 0.87 at 500, 50, 25 Kb). This procedure was repeated in IMR90, HMEC, NHEK, HUVEC, CH12-LX with similar results. The inventors also performed 112 supplementary Hi-C experiments using three different protocols (in situ Hi-C, dilution Hi-C, and Tethered Conformation Capture) while varying a wide array of conditions such as crosslinking time, restriction enzyme, ligation volume/time, and biotinylated nucleotide. The experiments demonstrated that the findings presented herein were robust to particular experimental conditions (see the sections on loop calling). In total, 201 independent Hi-C experiments were successfully performed. To identify fine-scale features in Hi-C maps, it is essential to account for non-uniformities in coverage due to the number of restriction sites at a locus or the accessibility of those sites to cutting (Cournac et al., BMC genomics 13, 436, 2012; Hu et al., Bioinformatics (Oxford, England) 28, 3131-3133, 2012; Imakaev et al., Nature methods 9, 999-1003, 2012; Lieberman-Aiden et al., Science 326, 289-293, 2009; Yaffe and Tanay, Nature genetics 43, 1059-1065, 2011). Either circumstance would increase the number of restriction fragments at the locus available for ligation, and thus the frequency of contacts involving the locus and any other locus. These non-uniformities were accounted for by normalizing each contact matrix using a matrix-balancing algorithm due to Knight and Ruiz (Knight and Ruiz, IMA Journal of Numerical Analysis, Published 26 Oct. 2012, Volume 33, Issue 3, July 2013, Pages 1029-1047). Three other published Hi-C bias-correction methods were also used (Cournac et al., BMC genomics 13, 436, 2012; Imakaev etal., Nature methods 9, 999-1003, 2012; Lieberman-Aiden et al., Science 326, 289-293, 2009); all produced similar results.

The Genome is Partitioned into Small Domains with Consistent Patterns of Chromatin.

It was next sought to use the vastly higher (200- to 1000-fold) map resolution of the present data to re-examine the three-dimensional partitioning of the genome. In earlier experiments at 1 Mb map resolution, large squares of enhanced contact frequency tiling the diagonal of the contact matrices were seen. These squares partitioned the genome into 5-20 Mb intervals, which we here call "megadomains." On opposite sides of a megadomain boundary, the contact frequency between pairs of loci drops sharply. Megadomains are very frequently preserved across cell types.

It was also found that individual 1 Mb loci could be assigned to one of two long-range contact patterns, which are termed herein Compartments A and B, with loci in the same compartment showing more frequent interaction. Megadomains—and the associated squares along the diagonal—arise when all of the 1 Mb loci in an interval exhibit the same genome-wide contact pattern (Kalhor et al., Nature biotechnology 30, 90-98, 2012; Lieberman-Aiden et al., Science 326, 289-293, 2009; Sexton et al., Cell 148, 458-472, 2012). Compartment A is highly enriched for open chromatin, and correlates strongly with DNaseI accessibility, active genes, and H3K36me3. Compartment B is enriched for closed chromatin.

Figure 4A:
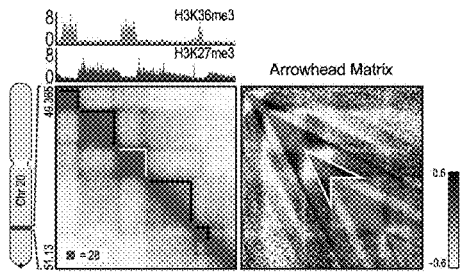
FIG. 4. The genome is partitioned into domains that segregate into nuclear subcompartments, corresponding to different patterns of histone modifications. (A) Thousands of domain are annotated (left, black highlight) using the arrowhead transformation (right), which converts domains into arrowhead-shaped motifs (example in yellow). (B) Pearson correlation matrices of the histone mark signal between pairs of loci inside, and within 100 Kb of, a domain. Left: H3K36me3; Right: H3K27me3. (C) Conserved domains on chromosome 3 in GM12878 (left) and IMR90 (right). In GM12878, the highlighted domain (gray) is enriched for H3K27me3 and depleted for H3K36me3. In IMR90, the situation is reversed. Marks at flanking domains are the same in both: the domain to the left is enriched for H3K36me3 and the domain to the right is enriched for H3K27me3. The flanking domains have long-range contact patterns which differ from one another and are preserved in both cell types. In IMR90, the central domain is marked by H3K36me3 and its long-range contact pattern matches the similarly-marked domain on the left. In GM12878, it is decorated with H3K27me3, and the long-range pattern switches, matching the similarly-marked domain to the right. Diagonal submatrices, 10 Kb resolution; long-range interaction matrices, 50 Kb resolution. (D) Each of the six long-range contact patterns we observe exhibits a distinct epigenetic profile. All epigenetic data is from ENCODE experiments in GM12878 except nuclear lamin (derived from skin fibroblast cells) and NAD (HeLa). See Table S8. Each subcompartment also has a visually distinctive contact pattern. (E) Each example shows part of the long-range contact patterns for several nearby genomic intervals lying in different compartments. (F) A large contiguous region on chromosome 19 contains intervals in subcompartments A1, B1, B2, and B4.
Figure 4B:
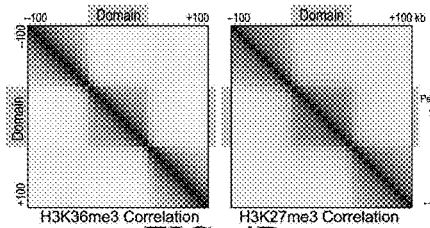
Figure 4C:
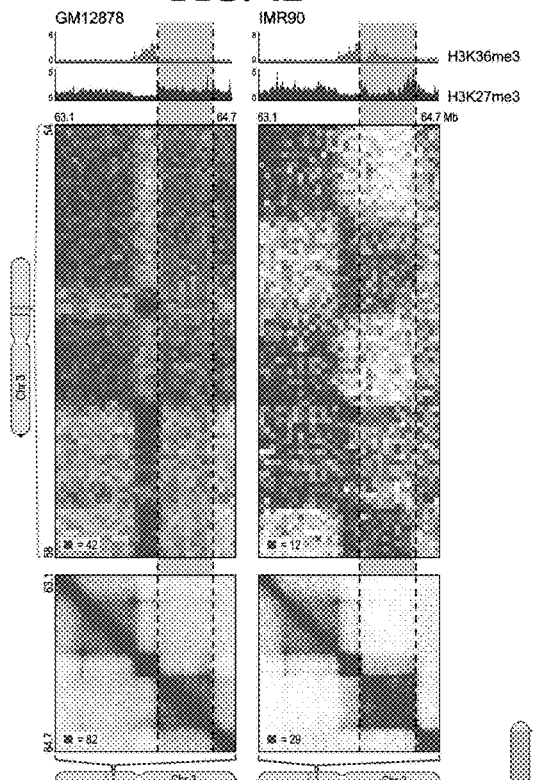
Figure 4D:
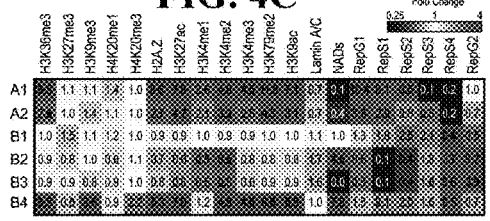
Figure 4E:
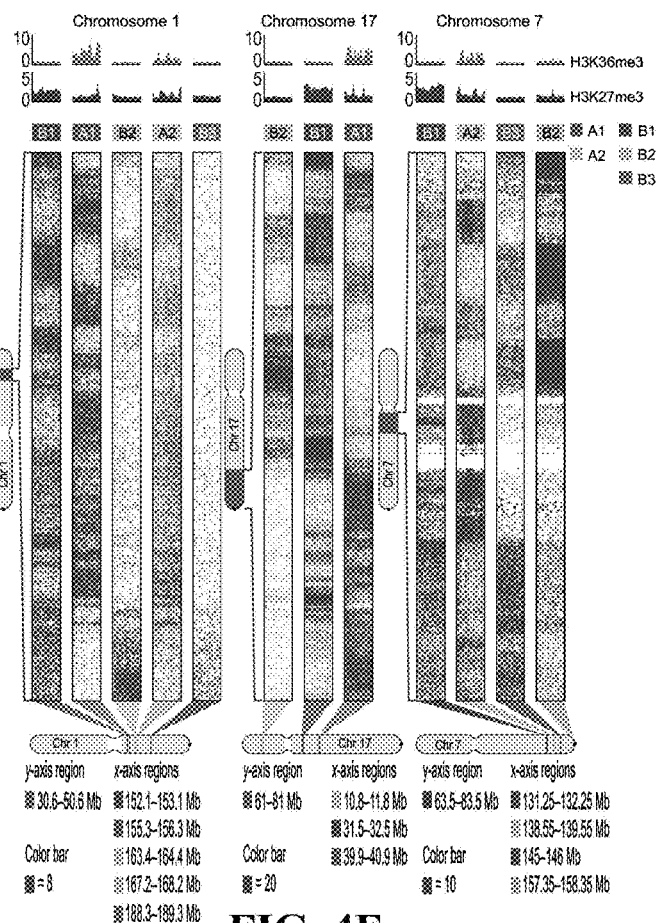
Figure 4F:
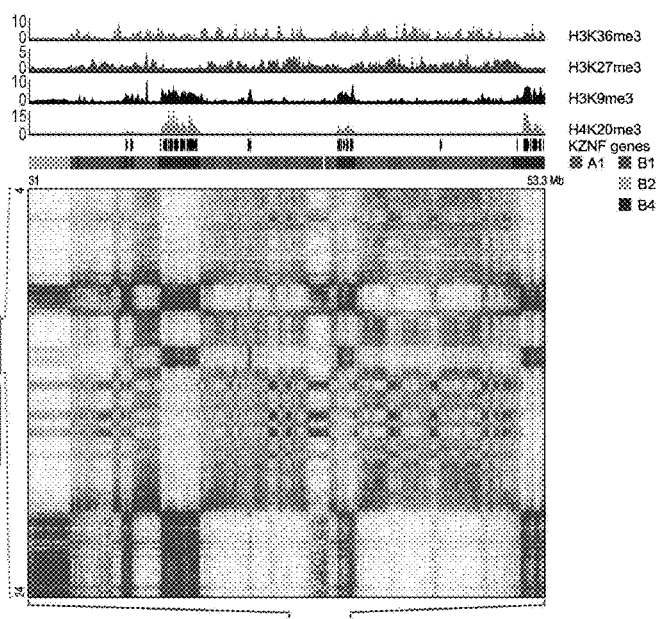

In the new, higher resolution maps presented herein, the inventors observed many small squares of enhanced contact frequency that tile the diagonal of each contact matrix (FIG. 4A). A dynamic programming algorithm was used to annotate these domains genome-wide. (Results using a previously published domain-calling algorithm (Dixon et al., Nature 485, 376-380, 2012) were similar.) The observed domains range in size from 40 Kb to 3 Mb (median size 185 Kb). As with megadomains, there is an abrupt drop in contact frequency (33%) for pairs of loci on opposite sides of the domain boundary. Domains are very frequently preserved across cell type. The presence of smaller domains in Hi-C maps is consistent with other recent reports (Dixon et al., Nature 485, 376-380, 2012; Nora et al., Nature 485, 381-385, 2012; Sexton et al., Cell 148, 458-472, 2012), although the domains observed here are considerably smaller, likely due to the much larger dataset. Changes in histone marks at a domain are associated with changes in long-range contact pattern Loci within a domain show strongly correlated chromatin states for eight different histone modifications (H3K36me3, H3K27me3, H3K4me1, H3K4me2, H3K4me3, H3K9me3, H3K79me2, and H4K20me1) based on data from the ENCODE project in GM12878 cells (Consortium, 2011 *PLoS biology vol.* 9,4: e1001046; Consortium et al., 2012 *ENCODE Project Consortium An integrated encyclopedia of DNA elements in the human genome. Nature.* 2012; 489: 57-74). By contrast, loci at comparable distance but residing in different domains showed much less correlation in chromatin state (FIG. 4B). Strikingly, changes in a domain's chromatin state are often accompanied by changes in the long-range contact pattern of domain loci (i.e., the pattern of contacts between loci in the domain and other loci genome-wide), indicating that changes in chromatin pattern are accompanied by shifts in a domain's nuclear neighborhood (FIG. 2C, S25).

There are at Least Six Nuclear Subcompartments with Distinct Patterns of Histone Modifications.

Next, it was sought to characterize the long-range contact patterns in the data. Loci were partitioned into categories based on long-range contact patterns alone, using four independent approaches: manual annotation, and three objective clustering algorithms (HMM, K-means, Hierarchical). All gave similar results. The biological meaning of these categories was then investigated.

When the data was analyzed at low matrix resolution (1 Mb), the earlier finding of two compartments (A and B) was reproduced. At high resolution (25 Kb), however, strong evidence was found for at least five "subcompartments" defined by their long-range interaction patterns, both within and between chromosomes. The median length of an interval lying completely within a subcompartment was 300 Kb. Although the five subcompartments are defined solely based on their Hi-C interaction patterns, they show distinctive properties with respect to both their genomic and epigenomic content. Two of the five interaction patterns are strongly correlated with loci in compartment A. The loci exhibiting these patterns were labeled as belonging to subcompartments A1 and A2. Both A1 and A2 are gene dense, have highly expressed genes, harbor activating chromatin marks such as H3K36me3, H3K79me2, H3K27ac and H3K4me1 and are depleted at the nuclear envelope and at nucleolus associated domains (NADs). (See FIG. 2D,E) A2 is more strongly associated with the presence of H3K9me3 than A1, and the genes residing in A2 tend to be longer (2.4-fold). The other three interaction patterns (labeled B1, B2, and B3) are strongly correlated with loci in compartment B, and show very different properties. Subcompartment B1 correlates positively with H3K27me3 and negatively with H3K36me3, suggestive of facultative heterochromatin (FIG. 2D,E). Subcompartment B2 includes 62% of pericentromeric heterochromatin (3.8-fold enrichment) and is enriched at the nuclear envelope (1.8-fold) and at NADs (4.6-fold). Subcompartment B3 tends to lack all of the above-noted marks, suggesting ordinary heterochromatin; it is enriched at the nuclear envelope (1.6-fold), but strongly depleted at NADs (76-fold). (See FIG. 2D, S28A.) Upon closer visual examination, we noticed the presence of a sixth pattern on chromosome 19 (FIG. 2F). The genome-wide clustering algorithm missed this pattern because it spans only 11 Mb, or 0.3% of the genome. When the algorithm was repeated on chromosome 19 alone, the additional pattern was detected. Because this sixth pattern correlates with the Compartment B pattern, it was labeled it B4. Subcompartment B4 comprises a handful of regions, each of which contain many KRAB-ZNF superfamily genes. (B4 contains 130 of the 278 KRAB-ZNF genes in the genome, a 65-fold enrichment). As noted in previous studies (Barski et al., Cell 129, 823-837, 2007; Hahn et al., PLoS One, 2011), these regions exhibit a distinctive chromatin pattern, with strong enrichment for both activating chromatin marks, such as H3K36me3, and heterochromatin-associated marks, such as H3K9me3 and H4K20 me3.

In principle, the fact that domains lying in the same subcompartment exhibit similar chromatin marks might reflect either that (i) spatial proximity enhances the spread of histone modifications, or (ii) similarity of histone modifications helps bring about spatial proximity.

Approximately 10,000 Peaks Mark the Position of Chromatin Loops

Figure 3C:
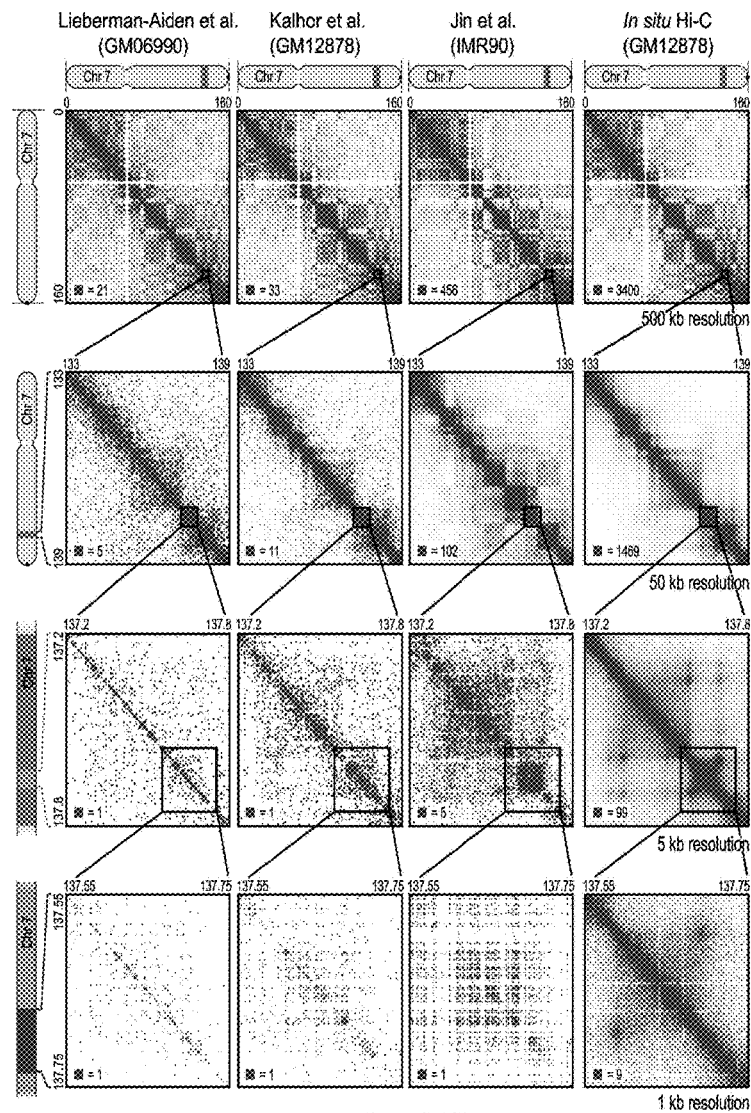
Figure 3D:
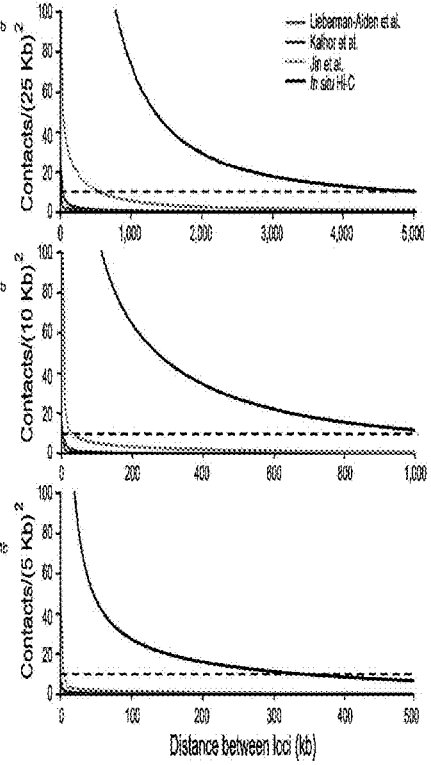
Figure 5A:
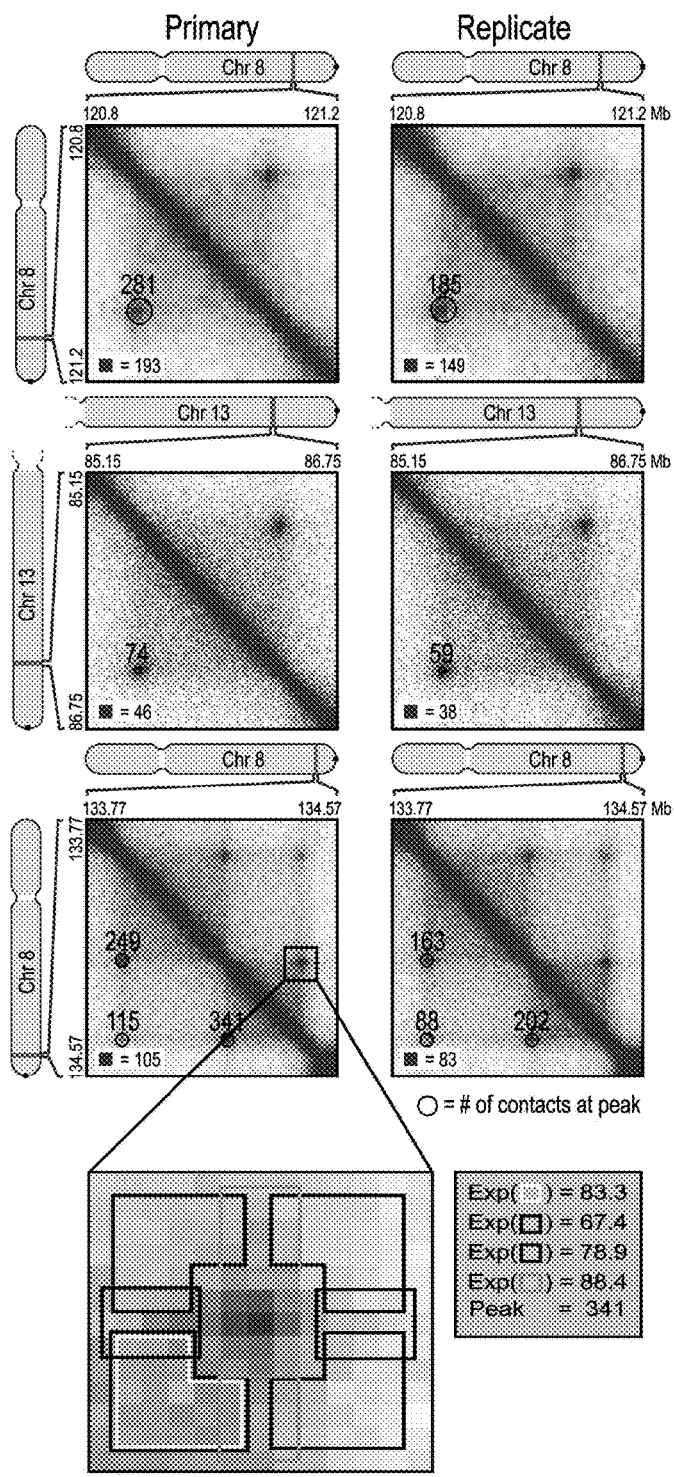
FIG. 5. The inventors identified thousands of chromatin loops genome-wide using a local background model. (A) The inventors identified peaks by detecting pixels that are enriched with respect to four local neighborhoods (blowout): horizontal (blue), vertical (green), lower-left (yellow), and donut (black). These "peak" pixels are marked with blue circles (radius=20 Kb) in the lower-left of each heatmap. The number of raw contacts at each peak is indicated. Left: primary GM12878 map; Right: replicate; annotations are completely independent. All contact matrices in these figures are 10 Kb resolution unless noted. (B) Overlap between replicates. (C) (Top) Location of 3D-FISH probes (Bottom) Example cell. (D) APA plot shows the aggregate signal from the 9948 GM12878 loops was made by summing submatrices surrounding each peak in a low-resolution GM12878Hi-C map due to Kalhor et al., Nature biotechnology 30, 90-98, 2012.
Figure 5B:
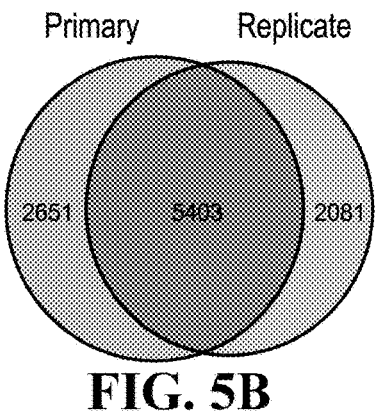
Figure 5C:
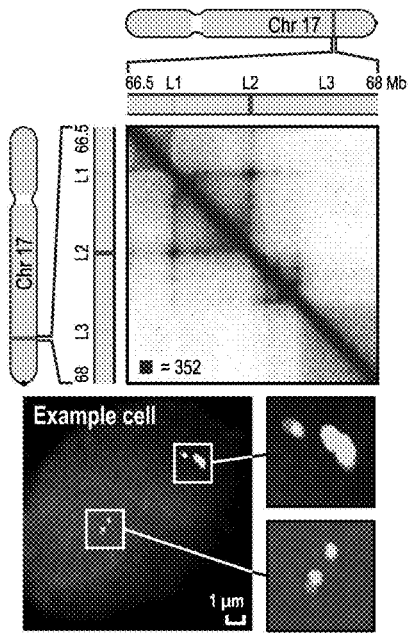
Figure 5D:
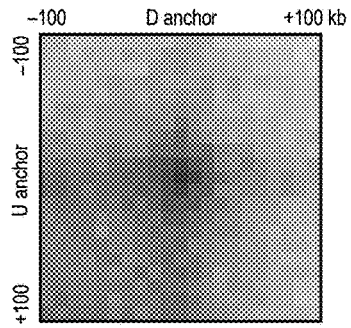

It was next sought to identify the positions of chromatin loops by using an algorithm to search for pairs of loci that show significantly closer proximity with one another than with the loci lying between them (FIG. 5A). Such pairs correspond to pixels with higher contact frequency than typical pixels in their neighborhood. These pixels are referred to as "peaks" in the Hi-C heatmap, and to the corresponding pair of loci as "peak loci". Peaks reflect the presence of chromatin loops, with the peak loci being the anchor points of the chromatin loop. (Because contact frequencies vary across the genome, peak pixels are defined relative to the local background. Of Note, some papers have sought to define peaks relative to the genome-wide average. This choice is problematic because, for example, many pixels within a domain may be reported as peaks despite showing no locally distinctive proximity.). The algorithm detected 9448 peaks in the in situ Hi-C map for GM12878 at 5 kb map resolution. These peaks are associated with a total of 12,903 distinct peak loci (some peak loci are associated with more than one peak). The vast majority of peaks (98%) reflected loops between loci that are less than 2 Mb apart. (Examining the primary and replicate maps separately, 8054 peaks were found in the former and 7484 peaks in the latter, with 5403 in both lists. The differences were almost always the result of conservative peak-calling criteria.) As an independent confirmation that peak loci have greater physical proximity than neighboring locus pairs, 3D-FISH (Beliveau et al., Proceedings of the National Academy of Sciences of the United States of America 109, 21301-21306, 2012) was performed on 4 loops. In each case, two peak loci, L1 and L2, were compared with a control locus, L3, that lies an equal distance away from L2 but on the opposite side (FIG. 3C). In all cases, the distance between L1 and L2 was consistently shorter than the distance between L2 and L3. It was also confirmed that the list of peaks was consistent with previously published Hi-C maps. Although earlier maps contained too few contacts to reliably call individual peaks, the inventors developed a method called Aggregate Peak Analysis (APA) that compares the aggregate enrichment of the peak set in these low-resolution maps to the enrichment seen when the peaks are translated in any direction. APA showed strong consistency between the loop calls and all six previously published Hi-C datasets for lymphoblastoid cell lines (Kalhor et al., Nature biotechnology 30, 90-98, 2012; Lieberman-Aiden et al., Science 326, 289-293, 2009; FIG. 3D). Finally, it was demonstrated that the list of peaks was robust to particular protocol conditions by performing APA analysis on a GM12878 dilution Hi-C map, and on the 112 supplemental Hi-C experiments exploring a wide range of protocol variants. Enrichment was seen in every single experiment.

Conservation of Peaks Among Human Cell Lines and Across Evolution

The inventors also identified peaks in the other six human cell lines (IMR90, HMEC, NHEK, K562, HUVEC, HeLa, and KBM7). Because these maps contain fewer contacts, sensitivity is reduced, and fewer peaks are observed (ranging from 2634 to 8040). Notably, APA analysis showed strong consistency between these peak calls and the dilution Hi-C maps reported here (in IMR90, HMEC, HUVEC, and NHEK), as well as with all previously published Hi-C maps in these cell types. Overall, it was found that peaks were strongly conserved across cell types (FIG. 6A): approximately half of the peaks found in any given cell type were also found in GM12878. We also compared peaks across species. In CH12-LX mouse B-lymphoblasts, we identified 2927 high-confidence domains and 3331 peaks. There was a strong correspondence between orthologous regions in GM12878 and CH12-LX. Overall, 50% of peaks and 45% of domains called in mouse were also called in humans, suggesting strong conservation of threedimensional genome structure across the mammals (FIG. 6B-E).

Loops Anchored at a Promoter are Associated with Enhancers and Increased Gene Activation Various lines of evidence indicate that many of the observed loops, defined by the peaks, are associated with gene regulation. First, the peaks frequently have a known promoter at one peak locus (as annotated by ENCODE's ChromHMM), and a known enhancer at the other (FIG. 7A). For instance, 2854 of the 9448 peaks in our GM12878 map bring together known promoters and known enhancers (30%, vs. 7% expected by chance). These peaks include well-studied promoter-enhancer loops, such as at MYC (chr8:128.35-128.75 Mb) and alpha-globin (chr16:0.15-0.22 Mb). Second, genes whose promoters are associated with a loop are much more highly expressed (6-fold). Third, the presence of cell type-specific peaks is associated with changes in gene expression.

Although peaks are strongly correlated across cell types, there were also many cases in which a peak was present in one cell type but not another. When we examined RNA-Seq data produced by ENCODE (ENCODE Consortium, 2011; ENCODE Consortium et al., 2012), it was found that the appearance of a loop in a cell type was frequently accompanied by the activation of a gene whose promoter overlapped one of the peak loci. For instance, 510 loops were observed in IMR90 that were clearly absent in GM12878. The corresponding peak loci overlapped the promoters of 94 genes that were markedly upregulated in IMR90 (>50-fold difference in RNA level), but of only 3 genes that were markedly upregulated in GM12878 (31-fold depletion). Conversely, 557 loops were found in GM12878 that were clearly absent in IMR90. The corresponding peak loci overlapped the promoters of 43 genes that were markedly upregulated in GM12878, but of only 1 gene that was markedly upregulated in IMR90: a 43-fold depletion. When GM12878 was compared to the five other human cell types for which ENCODE RNA-Seq data was available (all but KBM7), the results were very similar (FIG. 7B). One example of a cell-type specific loop is anchored at the promoter of the SELL gene, which encodes L-selectin, a lymphocyte-specific surface marker that is expressed in GM12878 but not IMR90 (FIG. 7C). Gene activation is occasionally accompanied by the emergence of a cell-type specific network of peaks. FIG. 7D illustrates the case of ADAMTS1, which encodes a protein involved in fibroblast migration. The gene is expressed in IMR90, where its promoter is involved in six loops. In GM12878, it is not expressed, and the promoter is involved in only two loops. Many of the IMR90 peak loci form transitive peaks with one another, suggesting that the ADAMTS1 promoter and the six distal sites may all be spatially co-located.

Peaks Frequently Demarcate the Boundaries of Domains

Figure 8A:
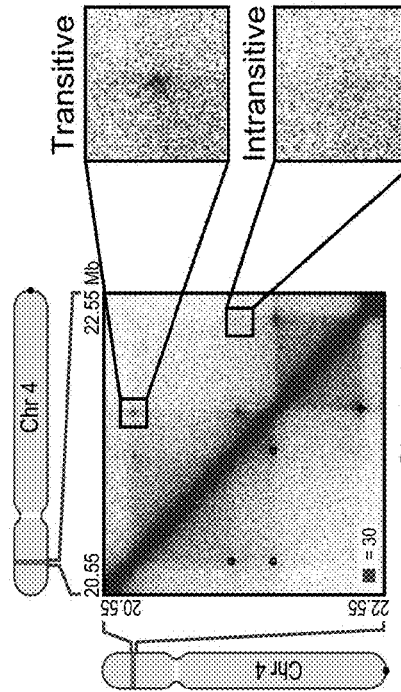
FIG. 8. Many loops demarcate domains; the vast majority of loops are anchored at a pair of convergent CTCF/RAD21/SMC3 binding sites. (A) Histograms of corner score for peak pixels vs. random pixels with an identical distance distribution. (B) Contact matrix for chr4:20.55 Mb-22.55 Mb in GM12878, showing examples of transitive and intransitive looping behavior. (C) % of peak loci bound vs. fold enrichment for 76 DNA-binding proteins. (D) The pairs of CTCF motifs that anchor a loop are nearly all found in the convergent orientation. (E) A peak on chromosome 1 and corresponding ChIP-Seq tracks. Both peak loci contain a single site bound by CTCF, RAD21, and SMC3. The CTCF motifs at the anchors exhibit a convergent orientation (Reverse motif consensus (SEQ ID No. 13), reverse sequence (SEQ ID No. 14), Forward motif consensus (SEQ ID No. 15), forward sequence (SEQ ID No. 16)).

A large fraction of peaks (38%) coincide with the corners of a domain—that is, the peak loci are located at domain boundaries (FIG. 8A). Conversely, a large fraction of domains (39%) had peaks in their corner. Moreover, the appearance of a loop is usually (in 65% of cases) associated with the appearance of a domain demarcated by the loop. Because this configuration is so common, we will use the term "loop domain" to refer to domains whose endpoints form a chromatin loop.

Figure 8B:
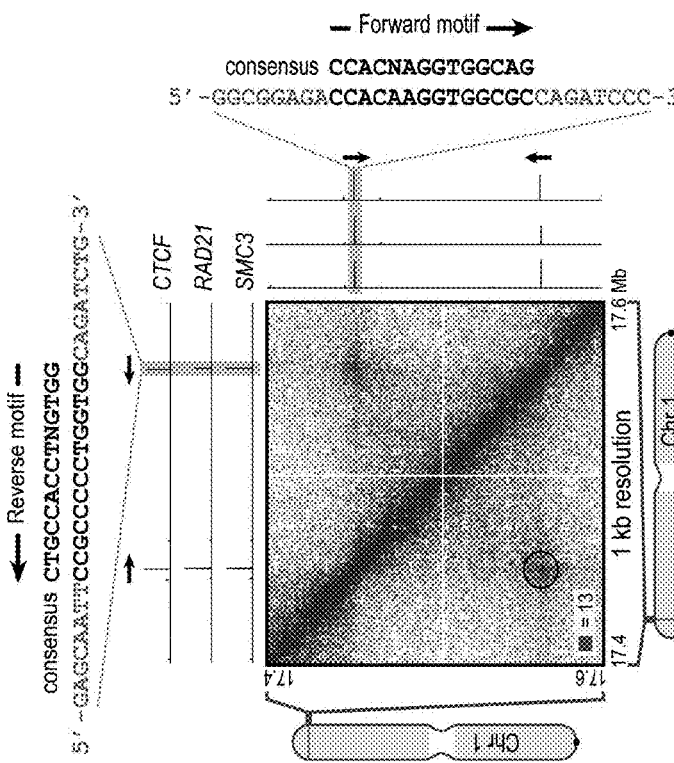

In some cases, adjacent loop domains (bounded by peak loci L1-L2 and L2-L3, respectively) exhibit transitivity—that is, L1 and L3 also correspond to a peak. In these situations, the three loci may simultaneously co-locate at a single spatial position. However, many peaks do not exhibit transitivity, suggesting that the loci may not co-locate simultaneously. FIG. 8B shows a region on chromosome 4 exhibiting both configurations. It was also found that overlapping loops are strongly disfavored: pairs of loops L1-L3 and L2-L4 (where L1, L2, L3 and L4 occur consecutively in the genome) are found far less often than expected under a random model.

Figure 6A:
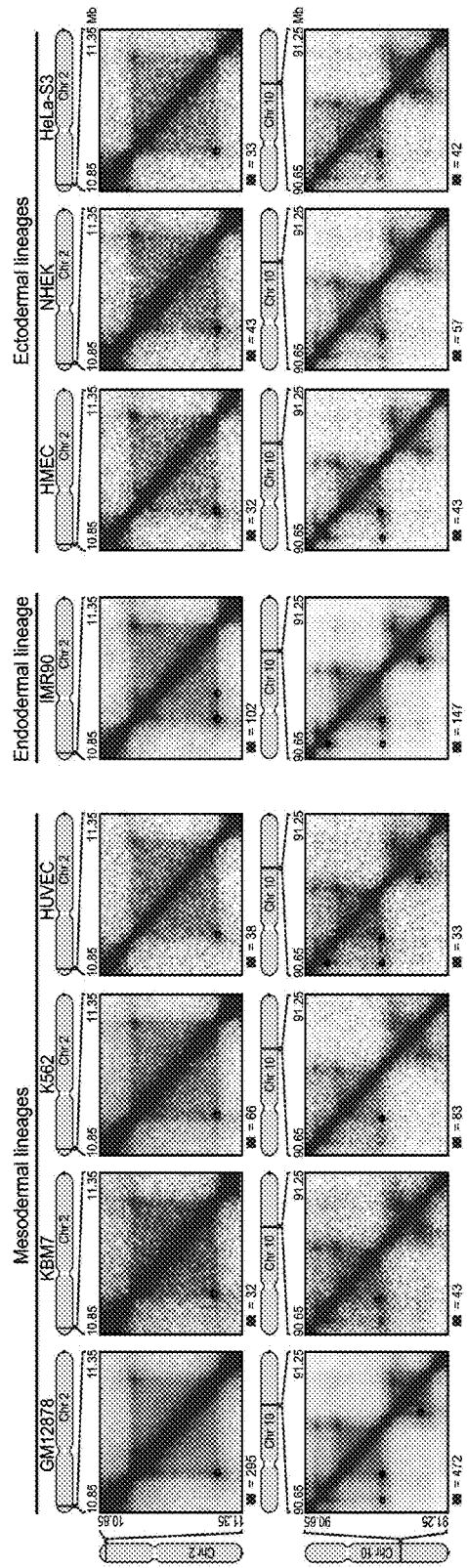
FIG. 6. Loops are often preserved across cell types and from human to mouse. (A) Examples of peak and domain preservation across cell types. Annotated peaks are circled in blue. All annotations are completely independent. (B) Of the 3331 loops we annotate in mouse CH12-LX, 1649 (50%) are orthologous to loops in human GM12878. (C-E) Conservation of threedimensional structure in synteny blocks.
Figure 6B:
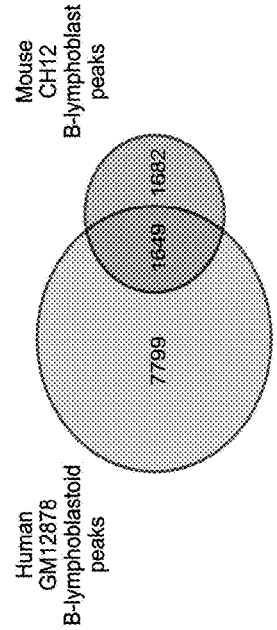
Figure 6C:
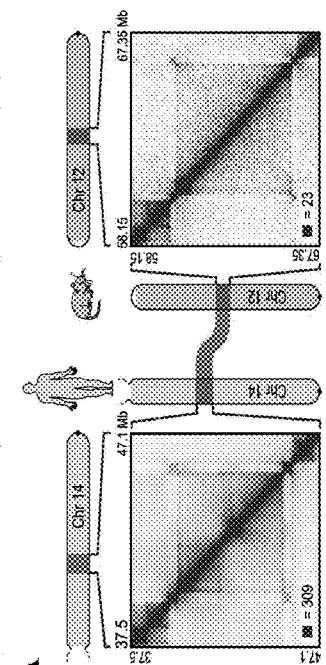
Figure 6D:
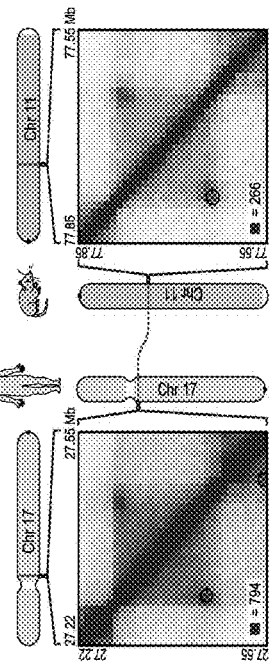
Figure 6E:
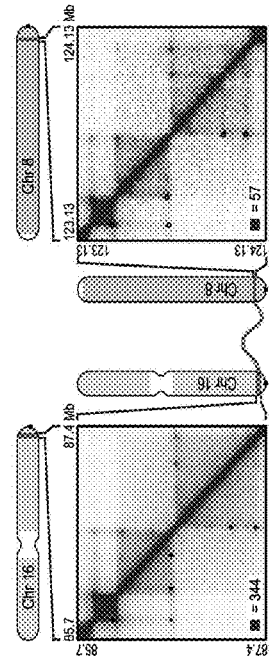
Figure 8C:
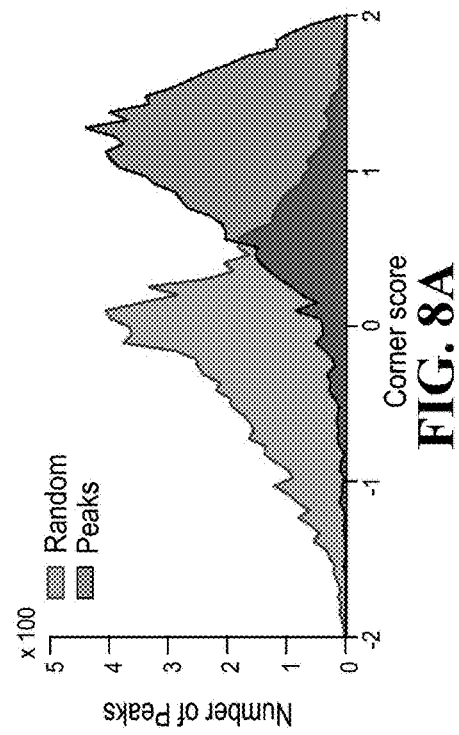
Figure 8E:
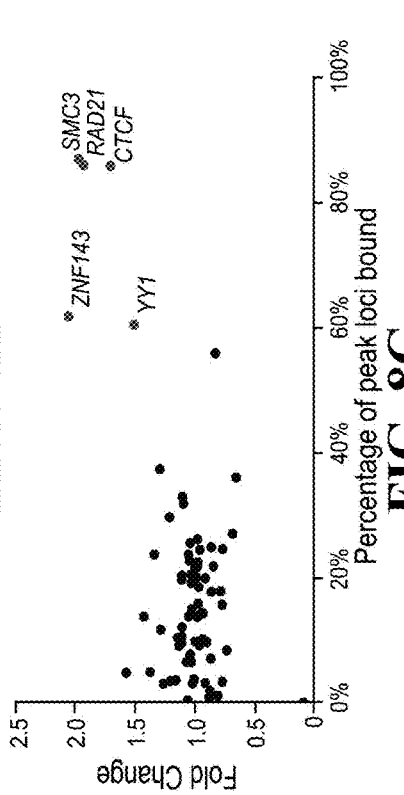
Figure 8D:
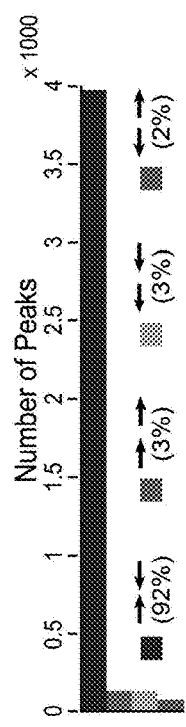

The Vast Majority of Peaks are Associated with Pairs of CTCF Motifs in a Convergent Orientation It was next asked whether peaks are associated with specific proteins. We therefore examined the results of 86 ChIP-Seq experiments performed by ENCODE in GM12878 (ENCODE Consortium, 2011; ENCODE Consortium et al., 2012). Strikingly, it was found that the vast majority of peak loci are bound by the insulator protein CTCF (86%) and the cohesin subunits RAD21 (86%) and SMC3 (87%) (FIG. 8C). Indeed, most peak loci contain a unique DNA site containing a CTCF binding motif, to which all three proteins (CTCF, SMC3, and RAD21) were bound (5-fold enrichment). We were thus able to associate most of the peak loci (6991 of 12,903) with a specific CTCF binding site "anchor". The consensus DNA sequence for CTCF binding sites is typically written as 5'-CCACNAGGTGGCAG-3'. Because the sequence is not palindromic, each CTCF site has an orientation; we designate the consensus motif above as the 'forward' orientation. Thus, a pair of CTCF sites on the same chromosome can have four possible orientations: (1) same direction on one strand; (2) same direction on the other strand; (3) convergent on opposite strands; and (4) divergent on opposite strands. If CTCF sites were randomly oriented, one would expect all 4 orientations to occur equally often. But when we examined the 4322 peaks in GM12878 where the two corresponding peak loci each contained a single CTCF binding motif, we found a stunning result: the vast majority (92%) of motif pairs are convergent (FIG. 6D,E). Overall, the presence, at pairs of peak loci, of bound CTCF sites in the convergent orientation was enriched 102-fold over random expectation. Notably, the convergent orientation was overwhelmingly more frequent than the divergent orientation, despite the fact that divergent motifs also lie on opposing strands: in GM12878, the counts were 3971-78 (51-fold enrichment of convergent vs. divergent); in IMR90, 1456-5 (291-fold); in HMEC, 968-11 (88-fold); in K562, 723 to 2 (362-fold); in HUVEC, 671-4 (168-fold); in HeLa, 301-3 (100-fold); in NHEK, 556-9 (62-fold); and in CH12, 625-8 (78-fold). This surprising pattern suggests that a pair of CTCF sites in the convergent orientation is required for the formation of a loop. The observation that looped CTCF sites occur in the convergent orientation also allows us to analyze peak loci containing multiple CTCF-bound motifs to predict which motif instance plays a role in a given loop. In this way, we can associate nearly two-thirds of peak loci (8175 of 12,903, or 63.4%) with a single CTCF binding site. The specific orientation of CTCF sites at observed peaks provides strong evidence that our peak calls are biologically correct. Because randomly chosen CTCF pairs would exhibit each of the four orientations with equal probability, the near-perfect association between our loop calls and the particular orientation could not occur by chance (p<10−1900). In addition, the presence of CTCF and RAD21 sites at many of our peaks provides an opportunity to compare our results to three recent CHIA-PET experiments reported by the ENCODE consortium (in GM12878 and K562) in which ligation junctions bound to CTCF (resp. RAD21) were isolated and analyzed. We found strong concordance with our results in all three cases.

Figure 9A:
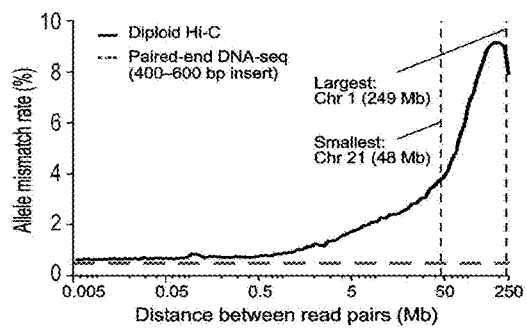
FIG. 9. Diploid Hi-C maps reveal superdomains and superloops anchored at CTCF-binding repeats on the inactive X chromosome. (A) The frequency of mismatch (maternal-paternal) in SNP allele assignment vs distance between two paired read alignments. Intrachromosomal read pairs are overwhelmingly intramolecular. (B) Preferential interactions between homologs. Left/top is maternal; right/bottom is paternal. The aberrant contact frequency between 6 p and 11 p (circle) reveals a translocation. (C) Top: In our unphased Hi-C map of GM12878, the inventors observed two loops joining both the promoter of the maternally-expressed H19 and the promoter of the paternally-expressed Igf2 to a distal locus, HIDAD. Using diploid Hi-C maps, the inventors phase these loops: the HIDAD-H19 loop is present only on the maternal homolog (left) and the HDAD-Igf2 loop is present only on the paternal homolog (right). (D) The inactive (paternal) copy of chromosome X (bottom) is partitioned into two massive "superdomains" not seen in the active (maternal) copy (top). DXZ4 lies at the boundary. (E) The "superloop" between FIRRE and DXZ4 is present in the GM12878 haploid map (top), in the paternal GM12878 map (middle right), and in the map of the female cell line IMR90
Figure 9B:
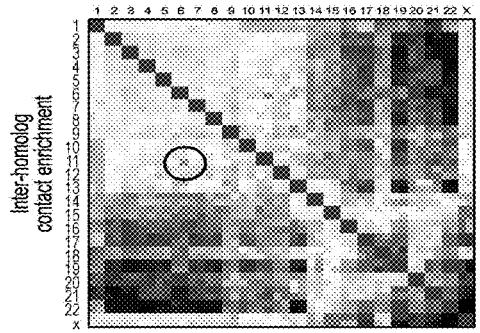
Figure 9D:
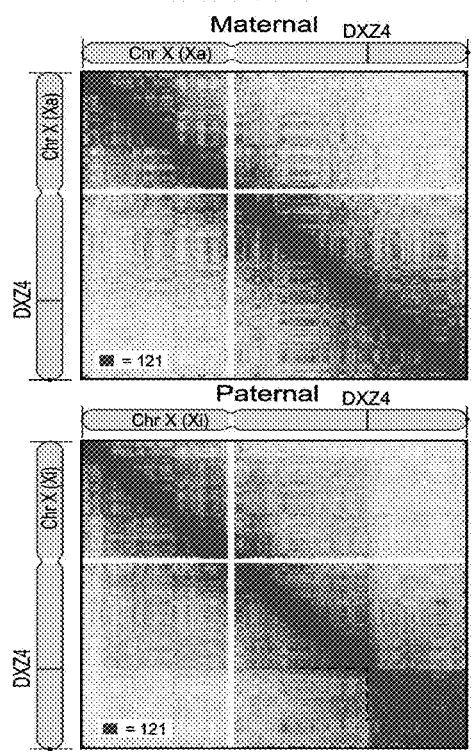
Figure 9C:
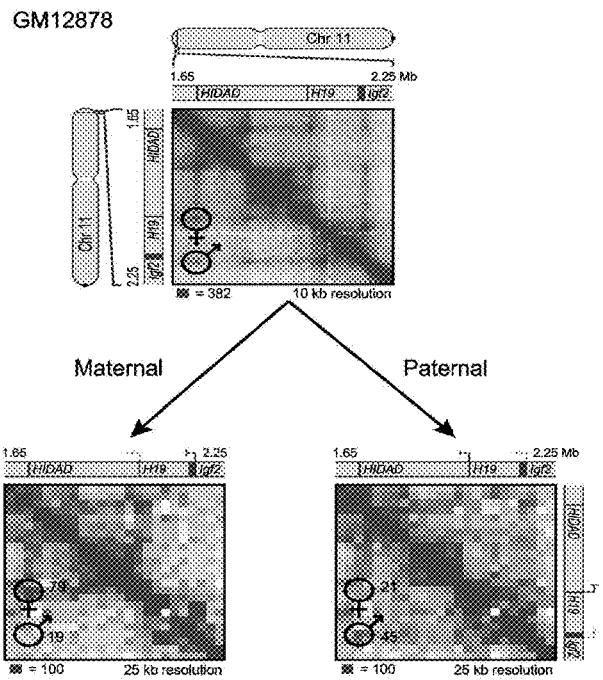
Figure 9E:
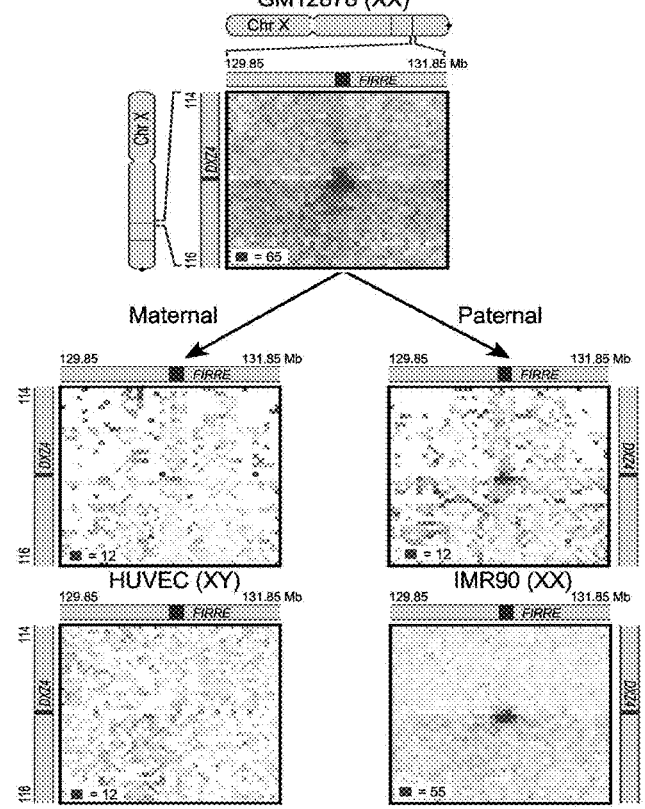

Diploid Hi-C Maps Reveals Homolog-Specific Features, Including Imprinting-Specific Loops and Massive Domains and Loops on the Inactive X-Chromosome Because many of our reads overlap SNPs, it is possible to assign contacts to specific chromosomal homologs. Using GM12878 SNP-phasing data (1000 Genomes Project Consortium et al., Nature 491, 7422, 2012, 56-65), we found that we could frequently assign reads to either the maternal or paternal homolog (FIG. 9A). Using these assignments, we constructed a "diploid" Hi-C map of GM12878 comprising both maternal (238M contacts) and paternal (240M) maps. We studied these maps for differences between homologous chromosomes in contact frequencies, domain structure, and loop structure. For autosomes, the maternal and paternal homologs exhibit very similar inter- and intrachromosomal contact profiles (Pearson's R>0.998, P value negligible). One interchromosomal difference was notable: an elevated contact frequency between the paternal homologs of chromosome 6 and 11 that is consistent with an unbalanced translocation fusing chr11q:73.5 Mb and all distal loci (a stretch of over 60 Mb) to the telomere of chromosome 6p (FIG. 7B, S39). The signal intensity suggests that the translocation is present in between 1.2% and 5.6% of our cells. We tested this prediction by karyotyping 100 GM12878 cells using Giemsa staining and found three abnormal chromosomes, each showing the predicted translocation, der(6)t(6,11)(pter;q) (Fig. S40-S41). Notably, the Hi-C data reveal that the translocation involves the paternal homologs, which cannot be determined with ordinary cytogenetic methods. We also observed differences in loop structure between homologous autosomes at some imprinted loci. For instance, the H19/Igf2 locus on chromosome 11 is a well-characterized case of genomic imprinting. In our unphased maps, we clearly see two loops from a single distal locus at 1.72 Mb (which binds CTCF in the forward orientation) to loci located near the promoters of both H19 and Igf2 (both of which bind CTCF in the reverse orientation, i.e., the above consensus motif lies on the opposite strand; see FIG. 7C). We refer to this distal locus as the H19/Igf2 Distal Anchor Domain (HIDAD). Our diploid maps reveal that the loop to the H19 region is present on the maternal chromosome (from which H19 is expressed), but the loop to the Igf2 region is absent or greatly attenuated. The opposite pattern is found on the paternal chromosome (from which Igf2 is expressed). Most strikingly, differences were seen on the diploid intrachromosomal maps of chromosome X. The paternal X chromosome, which is usually inactive in GM12878, is partitioned into two massive domains (0-115 Mb and 115-155.3 Mb). These "superdomains" are not seen in the active, maternal X (FIG. 7D). When we examined the unphased maps of chromosome X for the karyotypically normal female cell lines in our study (GM12878, IMR90, HMEC, NHEK), the superdomains on X were evident, although the signal was markedly attenuated by the superposition of signals from active and inactive X chromosomes. When we examined the male HUVEC cell line and the haploid KBM7 cell line, we saw no evidence of superdomains (Fig. S42). Interestingly, the boundary between the superdomains (ChrX: 115 Mb+/−500 Kb) lies near the macrosatellite repeat DXZ4 (ChrX: 114,867,433-114,919, 088) near the middle of Xq. DXZ4 is a CpG-rich tandem repeat that is conserved across primates and monkeys and encodes a long non-coding RNA. In males and on the active X, DXZ4 is heterochromatic, hyper-methylated and does not bind CTCF. On the inactive X, DXZ4 is euchromatic, hypo-methylated, and binds CTCF. DXZ4 has been hypothesized to play a role in reorganizing chromatin during X inactivation (Chadwick, *Genome Res.* 2008; 18: 1259-1269). There were also significant differences in loop structure between the chromosome X homologs. We observed 27 extremely large "superloops," each spanning between 7 and 74 Mb, present only on the inactive X chromosome in the diploid map (FIG. 7E). The superloops were also seen in all 4 unphased maps from karyotypically normal XX cells, but were absent in unphased maps from X0 and XY cells (Fig. S43). Two of the superloops (chrX:56.8 Mb-DXZ4 and DXZ4-130.9 Mb) have been reported previously, and their presence on the inactive X alone has been confirmed using multiple methods (Horakova et al., Human molecular genetics 21, 4367-4377, 2012). Like the peak loci of most other loops, nearly all the superloop anchors bind CTCF (25 of 26). The six anchor regions most frequently associated with superloops are very large (up to 200 kb). Four of these anchor regions contain whole lncRNA genes: loc550643; XIST; DXZ4; and FIRRE. Three (loc550643, and DXZ4, and FIRRE) contain CTCF-binding tandem repeats that only bind CTCF on the inactive homolog. DISCUSSION The in situ Hi-C protocol allowed us to probe genomic architecture with extremely high resolution; in the case of GM12878 lymphoblastoid cells, better than 1 kb. We observe the presence of domains that were too small to be seen in our original Hi-C maps, which had resolution of 1 Mb (Lieberman-Aiden et al., Science 326, 289-293, 2009). Loci within a domain interact frequently with one another, have similar patterns of chromatin modifications, and exhibit similar long-range contact patterns. Domains tend to be conserved across cell types and between human and mouse. Strikingly, when the pattern of chromatin modifications associated with a domain changes, the domain's long-range contact pattern also changes. The domains exhibit six distinct patterns of long-range contacts (subcompartments), which subdivide the two compartments that we had reported based on low resolution data. The subcompartments are each associated with distinct chromatin patterns. It is possible that the chromatin patterns play a role in bringing about the long-range contact patterns, or vice versa. High-resolution in situ Hi-C data makes it possible to create a genome-wide catalog of chromatin loops. We identified loops by looking for pairs of loci that have significantly more contacts with one another than they do with other nearby loci. In our densest map, GM12878 lymphoblastoid cells, we observe 9448 loops. We note that our annotation identifies fewer loops than were reported in several recent highthroughput studies. The key reason is that we call peaks only when a pair of loci shows elevated contact frequency relative to the local background—that is, when the peak pixel is enriched as compared to other pixels in its neighborhood. In contrast, several previous studies have defined peaks by comparing the contact frequency at a pixel to the genome-wide average. This latter definition is problematic because many pixels within a domain can be annotated as peaks despite showing no local increase in contact frequency. Previous papers using the latter definition imply the existence of more than 100,000 or even more than 1 million peaks (Extended Experimental Procedures). The loops we observe have many interesting properties. First, most loops are short (<2 Mb). Second, loops are strongly conserved across cell types and between human and mouse. Third, promoter-enhancer loops are common and are strongly associated with gene activation. Fourth, loops often demarcate domains, and may establish them. Fifth, loops tend not to overlap. Sixth, loops are closely associated with the presence of CTCF and the cohesin subunits RAD21 and SMC3; each of these proteins is found at over 86% of loop anchors. The most striking property of loops is that the pair of CTCF motifs present at the loop anchors occurs in a convergent orientation in >90% of cases (vs. 25% expected by chance). The importance of motif orientation between loci that are separated by, on average, 360 Kb is unexpected and must bear on the mechanism by which CTCF and cohesin form loops, which likely involves CTCF dimerization. Experiments in which the presence or orientation of CTCF sites is altered should shed light on this mechanism. Such experiments may also enable the engineering of loops, domains, and other chromatin structures.

We also created diploid Hi-C maps, by using polymorphisms to assign contacts to distinct chromosomal homologs. We find that the inactive X chromosome is partitioned into two large "superdomains" whose boundary lies near the locus of the lncRNA DXZ4 (Chadwick, *Genome Res.* 2008; 18: 1259-1269). We also detect a network of extremely long-range (7-74 Mb) "superloops", the strongest of which are anchored at locations containing lncRNA genes (loc550643, XIST, DXZ4, and FIRRE). With the exception of XIST, all of these lncRNAs contain CTCF-binding tandem repeats that bind CTCF only on the inactive X. We hypothesize that Xi-specific CTCF binding participates in the formation of these massive chromatin structures. Just as loops bring distant DNA loci into close spatial proximity, we find that they bring disparate aspects of DNA biology—domains, compartments, chromatin marks, and genetic regulation—into close conceptual proximity. As our understanding of the physical connections between DNA loci continues to improve, our understanding of the relationships between these broader phenomena will deepen.

Experimental Procedures

In Situ Hi-C Protocol

All cell lines used were cultured following the manufacturer's recommendations. Cells were crosslinked with 1% formaldehyde for 10 minutes at room temperature. In situ Hi-C was performed by permeabilizing 2-5M nuclei. DNA was digested with 100 units of MboI (or DpnII), the ends of restriction fragments were labeled using biotinylated nucleotides, and were then ligated in a small volume. After reversal of crosslinks, ligated DNA was purified and sheared to a length of roughly 400 basepairs, at which point ligation junctions were pulled down with streptavidin beads and prepped for high-throughput Illumina® sequencing. Dilution Hi-C was performed as in (Lieberman-Aiden et al Science 326, 289-293, 2009).

3D-FISH

FISH probes were designed using the OligoPaints database. DNA-FISH was performed as described in (Beliveau et al., Proceedings of the National Academy of Sciences of the United States of America 109, 21301-21306, 2012), with minor modifications.

Hi-C Data Pipeline

All sequence data was produced using Illumina® paired-end sequencing. Sequence data was processed using a custom pipeline that was optimized for parallel computation on a cluster. The pipeline uses BWA (Li and Durbin, Bioinformatics (Oxford, England) 26, 589-595, 2010) to map each read end separately to the b37 or mm9 reference genomes; removes duplicate and near-duplicate reads; removes reads that map to the same fragment; and filters the remaining reads based on mapping quality score. Contact matrices were generated at base-pair delimited resolutions of 2.5 Mb, 1 Mb, 500 Kb, 250 Kb, 100 Kb, 50 Kb, 25 Kb, 10 Kb, 5 Kb, as well as fragment-delimited resolutions of 500 f, 200 f, 100 f, 50 f, 20 f, 5 f, 2 f, and 1 f. For the largest data sets, the file also contains a 1 Kb contact matrix. Normalized contact matrices are produced at all resolutions using (Knight and Ruiz, IMA Journal of Numerical Analysis, 2012).

Annotation of Domains

To annotate domains, a novel "arrowhead" transformation was applied, defined as $A_{i,i+d}=(M^*_{i,i-d}-M^*_{i,i+d})/(M^*_{i,i-d}+M^*_{i,i+d})$. $M^*$ denotes the normalized contact matrix. This transformation can be thought of as equivalent to calculating a matrix equal to $-1*$(observed/expected$-1$), where the expected model controls for local background and distance from the diagonal in the simplest possible way: the "expected" value at $i,i+d$ is simply the mean observed value at $i,i-d$ and $i,i+d$. $A_{i,i+d}$ will be strongly positive if and only if locus $i-d$ is inside a domain and locus $i+d$ is not. If the reverse is true, $A_{i,i+d}$ will be strongly negative. If the loci are both inside or both outside a domain, $A_{i,i+d}$ will be close to zero. Consequently, if there is a domain at [a,b], we find that A takes on very negative values inside a triangle whose vertices lie at [a,a], [a,b], and [(a+b)/2,b], and very positive values inside a triangle whose vertices lie at [(a+b)/2,b], [b,b], and [b,2b−a]. The size and positioning of these triangles creates the arrowhead-shaped feature that replaces each domain in $M^*$. A "corner score" matrix, indicating each pixel's likelihood of lying at the corner of a domain, is efficiently calculated from the arrowhead matrix using dynamic programming.

Assigning Loci to Subcompartments

To cluster loci based on long-range contact patterns, we constructed a 100 Kb resolution contact matrix comprising a subset of the interchromosomal contact data. Loci on odd chromosomes appeared on the rows, and loci from the even chromosomes appeared on the columns. (Chromosome X was excluded.) This matrix was clustered using the Python package scikit. To generate annotation of subcompartment B4, the 100 kb interchromosomal matrix for chromosome 19 was constructed and clustered separately, using the same procedure.

Annotation of Peaks

The peak-calling algorithm examines each pixel in a Hi-C contact matrix and compares the number of contacts in the pixel to the number of contacts in a series of regions surrounding the pixel. The algorithm thus identifies pixels $M^*_{i,j}$ where the contact frequency is higher than expected, and where this enrichment is not the result of a larger structural feature. For instance, ruling out the possibility that the enrichment of pixel $M^*_{i,j}$ is the result of Li and Lj lying in the same domain by comparing the pixel's contact count to an expected model derived by examining the "lower-left" neighborhood. (The "lower-left" neighborhood samples pixels $M_{i',j'}$ where $i \leq i' \leq j' \leq j$; if a pixel is in a domain, these pixels will necessarily be in the same domain.) It is requires that the pixel being tested contain at least 50% more contacts than expected, and that this enrichment be statistically significant after correcting for multiple hypothesis testing (FDR <10%). The same criteria are applied to three other neighborhoods. To be labeled an "enriched pixel," a pixel must therefore be significantly enriched relative to four neighborhoods: (i) pixels to its lower-left; (ii) pixels to its left and right; (iii) pixels above and below; and (iv) a donut surrounding the pixel of interest (FIG. 6A). Using this approach, numerous enriched pixels were identified across the genome. The enriched pixels tend to form contiguous interaction regions comprising 5-20 pixels each. We define the "peak pixel" (or simply the "peak") to be the pixel in an interaction region with the largest number of contacts. Because over 10 billion (10 Kb)$^2$ pixels must be examined, this calculation requires weeks of CPU time to execute. To accelerate it, a highly parallelized implementation was created using general-purpose graphical processing units, resulting in a 200-fold speedup relative to initial, CPU-based approach.

Aggregate Peak Analysis

APA is performed on 10 Kb resolution contact matrices. To measure the aggregate enrichment of a set of putative peaks in a contact matrix, we plot the sum of a series of submatrices derived from that contact matrix. Each of these submatrices is a 210 Kb×210 Kb square centered at a single putative peak in the upper triangle of the contact matrix. The resulting APA plot displays the total number of contacts that lie within the entire putative peak set at the center of the matrix; the entry immediately to the right of center corresponds to the total number of contacts in the pixel set obtained by shifting the peak set 10 Kb to the right; the entry two positions above center corresponds to an upward shift of 20 Kb, and so on. Focal enrichment across the peak set in aggregate manifests as larger values at the center of the APA plot. APA analyses only include peaks whose loci are at least 300 Kb apart.

Example 2

Comparison of results obtained for In situ determination of nucleic acid proximity as described herein and a Hi-C protocol. As shown herein, the disclosed methods yield a result with greater complexity, which indicates more interactions that can be mapped and consequently more information. In other words, 'complexity' . . . this is the number of total contacts/datapoints produced by the experiment, thus the greater number of data points, the more information is extracted from each trial. In addition, method disclosed herein provide more the 'large' reads, which correspond to a long distance intrachromosomal contact. These contacts are the most informative ones, as they can pin down the long range interactions in the cell. The data presented herein demonstrate that the methods disclosed herein are superior than the previous Hi-C methods. The methods and protocols disclosed below are non-limiting examples of the methods disclosed herein and variation on the protocols in envisioned, such as the times, temperatures, and specific reagents used. Some steps maybe omitted and others added.

In Situ Hi-C Protocol Prepped for Illumina Sequencing

Crosslinking

1) Grow two to five million cells under recommended culture conditions to about 80% confluence. Pellet suspension cells or detached adherent cells by centrifugation at 300×G for 5 min.
2) Resuspend cells in fresh medium at concentration of $1 \times 10^6$ cells per 1 ml media. In a fume hood, add freshly made formaldehyde solution to a final concentration of 1%. Incubate at room temperature for 10 min with mixing. In some examples, no crosslinking is performed and the proximity relationships between nucleic acids are maintained via other means, for example by embedding nuclei in agarose.
3) Add 2.5M glycine solution to a final concentration of 0.2M to quench the reaction. Incubate at room temperature for 5 min on rocker.
4) Centrifuge for 5 min at 300×G at 4° C. Discard supernatant into an appropriate collection container.
5) Resuspend cells in 1 ml of cold 1×PBS and spin for 5 min at 300×G at 4° C. Discard supernatant and flash-freeze cell pellets in liquid nitrogen or dry ice/ethanol.
6) Either proceed to the rest of the protocol or store cell pellets at −80° C.

Lysis and Restriction Digest
  7) Combine 250 µl of ice-cold Hi-C lysis buffer (10 mM Tris-HCl pH8.0, 10 mM NaCl, 0.2% Igepal CA630) with 50 µl of protease inhibitors (Sigma, P8340). Add to one cross-linked pellet of cells.
  8) Incubate cell suspension on ice for >15 minutes. Centrifuge at 2500×G for 5 minutes. Discard the supernatant.
  9) Wash pelleted nuclei once with 500 µl of ice-cold Hi-C lysis buffer.
  10) Gently resuspend pellet in 50 µl of 0.5% sodium dodecyl sulfate (SDS) and incubate at 62° C. for 5-10 minutes.
  11) After heating is over, add 145 µl of water and 25 µl of 10% Triton® X-100 (Sigma, 93443) to quench SDS. Mix well, avoiding excessive foaming. Incubate at 37° C. for 15 minutes.
  12) Add 25 µl of 10×NEBuffer2 and 100 U of MboI restriction enzyme (New England Biolabs (NEB, R0147)) and digest chromatin for at least 2 h or overnight at 37° C. with rotation.
    In some examples, Hi-C can be performed with an additional centrifugation step added after restriction (step 12) and prior to fill-in.

Marking of DNA Ends, Proximity Ligation, and Crosslink Reversal
  13) Incubate at 62° C. for 20 minutes, then cool to room temperature.
  14) To fill in the restriction fragment overhangs and mark the DNA ends with biotin, add 50 µl of fill-in master mix:
    37.5 µl of 0.4 mM biotin-14-dATP (Life Technologies, 19524-016)
    1.5 µl of 10 mM dCTP
    1.5 µl of 10 mM dGTP
    1.5 µl of 10 mM dTTP
    8 µl of 5 U/µl DNA Polymerase I, Large (Klenow) Fragment (NEB, M0210)
  15) Mix by pipetting and incubate at 37° C. for 45 min-1.5 hours with rotation.
  16) Add 900 µl of ligation master mix:
    663 µl of water
    120 µl of 10×NEB T4 DNA ligase buffer (NEB, B0202)
    100 µl of 10% Triton X-100
    12 µl of 10 mg/ml Bovine Serum Albumin (100×BSA)
    5 µl of 400 U/µl T4 DNA Ligase (NEB, M0202)
  17) Mix by inverting and incubate at room temperature for 4 hours with slow rotation.
  18) Degrade protein by adding 50 µl of 20 mg/ml proteinase K (NEB, P8102) and 120 µl of 10% SDS and incubate at 55° C. for 30 minutes. (In some examples nuclei can be pelleted after ligation (step 17) and then resuspended, both to remove random ligations that may have occurred in solution and to reduce the overall volume for ease of handling.)
  19) Add 130 µl of 5M sodium chloride and incubate at 68° C. for at least 1.5 hours or overnight.

DNA Shearing and Size Selection
  20) Cool tubes at room temperature.
  21) Split into two 750 µl aliquots in 2 ml tubes and add 1.6× volumes of pure ethanol and 0.1× volumes of 3M sodium acetate, pH 5.2, to each tube. Mix by inverting and incubate at −80° C. for 15 minutes.
  22) Centrifuge at max speed, 2° C. for 15 minutes. Keeping tubes on ice after spinning, carefully remove the supernatant by pipetting.
  23) Resuspend, combining the two aliquots, in 800 µl of 70% ethanol. Centrifuge at max speed for 5 minutes.
  24) Remove all supernatant and wash the pellet once with 800 µl of 70% ethanol.
  25) Dissolve pellet in 130 µl of 1×Tris buffer (10 mM Tris-Cl, pH 8) and incubate at 37° C. for 15 minutes to fully dissolve DNA.
  26) To make the biotinylated DNA suitable for high-throughput sequencing using Illumina sequencers, shear to a size of 300-500 bp using the following parameters:
    Instrument: Covaris LE220 (Covaris, Woburn, Mass.)
    Volume of Library: 130 µl in a Covaris microTUBE
    Fill Level: 10
    Duty Cycle: 15
    PIP: 500
    Cycles/Burst: 200
    Time: 58 seconds
  27) Transfer sheared DNA to a fresh 1.5 ml tube. Wash the Covaris vial with 70 µl of water and add to the sample, bringing the total reaction volume to 200 µl Run a 1:5 dilution of DNA on a 2% agarose gel to verify successful shearing. For libraries containing fewer than $2 \times 10^6$ cells, the size selection using AMPure XP beads described in the next steps could be performed on final amplicons rather than before pull-down.
  28) Warm a bottle of AMPure XP beads (Beckman Coulter, A63881) to room temperature. To increase yield, AMPure XP beads can be concentrated by removing some of the clear solution before the beads are mixed for use in the next steps.
  29) Add exactly 110 µl (0.55× volumes) of beads to the reaction. Mix well by pipetting and incubate at room temperature for 5 minutes.
  30) Separate on a magnet. Transfer clear solution to a fresh tube, avoiding any beads. The supernatant will contain fragments shorter than 500 bp.
  31) Add exactly 30 µl of fresh AMPure XP beads to the solution. Mix by pipetting and incubate at room temperature for 5 minutes.
  32) Separate on a magnet and keep the beads. Fragments in the range of 300-500 bp will be retained on the beads.
  33) Keeping the beads on the magnet, wash twice with 700 µl of 70% ethanol without mixing.
  34) Leave the beads on the magnet for 5 minutes to allow remaining ethanol to evaporate.
  35) To elute DNA, add 300 µl of 1× Tris buffer, gently mix by pipetting, incubate at room temperature for 5 minutes, separate on a magnet, and transfer the solution to a fresh 1.5 ml tube.
  36) Quantify DNA by Qubit dsDNA High Sensitivity Assay (Life Technologies, Q32854) and run undiluted DNA on a 2% agarose gel to verify successful size selection.

Biotin Pull-Down and Preparation for Illumina Sequencing
  Perform all steps in low-bind tubes.
  37) Prepare for biotin pull-down by washing 150 µl of 10 mg/ml Dynabeads MyOne Streptavidin T1 beads (Life technologies, 65602) with 400 µl of 1× Tween Washing Buffer (1×TWB: 5 mM Tris-HCl (pH 7.5); 0.5 mM EDTA; 1M NaCl; 0.05% Tween 20). Separate on a magnet and discard the solution.
  38) Resuspend the beads in 300 µl of 2× Binding Buffer (2×BB: 10 mM Tris-HCl (pH 7.5); 1 mM EDTA; 2M NaCl) and add to the reaction. Incubate at room temperature for 15 minutes with rotation to bind biotinylated DNA to the streptavidin beads.
39) Separate on a magnet and discard the solution.
40) Wash the beads by adding 600 μl of 1×TWB and transferring the mixture to a new tube. Heat the tubes on Thermomixer at 55° C. for 2 min with mixing. Reclaim the beads using a magnet. Discard supernatant.
41) Repeat wash.
42) Resuspend beads in 100 μl 1×NEB T4 DNA ligase buffer (NEB, B0202) and transfer to a new tube. Reclaim beads and discard the buffer.
43) To repair ends of sheared DNA and remove biotin from unligated ends, resuspend in 100 μl of master mix:
   88 μl of 1×NEB T4 DNA ligase buffer with 10 mM ATP
   2 μl of 25 mM dNTP mix
   5 μl of 10 U/μl NEB T4 PNK (NEB, M0201)
   4 μl of 3 U/μl NEB T4 DNA polymerase I (NEB, M0203)
   1 μl of 5 U/μl NEB Klenow fragment of DNA polymerase I (NEB, M0210)
44) Incubate at room temperature for 30 minutes. Separate on a magnet and discard the solution.
45) Wash the beads by adding 600 μl of 1×TWB and transferring the mixture to a new tube. Heat the tubes on Thermomixer at 55° C. for 2 min with mixing. Reclaim the beads using a magnet. Discard supernatant.
46) Repeat wash.
47) Resuspend beads in 100 μl 1×NEBuffer 2 and transfer to a new tube. Reclaim beads and discard the buffer.
48) Resuspend in 100 μl of dATP attachment master mix:
   90 μl of 1×NEBuffer 2
   5 μl of 10 mM dATP
   5 μl of 5 U/μl NEB Klenow exo minus (NEB, M0212)
49) Incubate at 37° C. for 30 minutes. Separate on a magnet and discard the solution.
50) Wash the beads by adding 600 μl of 1×TWB and transferring the mixture to a new tube. Heat the tubes on Thermomixer at 55° C. for 2 min with mixing. Reclaim the beads using a magnet. Discard supernatant.
51) Repeat wash.
52) Resuspend beads in 100 μl Quick ligation reaction buffer (NEB, B6058) and transfer to a new tube. Reclaim beads and discard the buffer.
53) Resuspend in 50 μl of 1×NEB Quick ligation reaction buffer.
54) Add 2 μl of NEB DNA Quick ligase (NEB, M2200). Add 3 μl of an Illumina indexed adapter. Record the sample-index combination. Mix thoroughly.
55) Incubate at room temperature for 15 minutes. Separate on a magnet and discard the solution.
56) Wash the beads by adding 600 μl of 1×TWB and transferring the mixture to a new tube. Heat the tubes on Thermomixer at 55° C. for 2 min with mixing. Reclaim the beads using a magnet. Remove supernatant.
57) Repeat wash.
58) Resuspend beads in 100 μl 1× Tris buffer and transfer to a new tube. Reclaim beads and discard the buffer.
59) Resuspend in 50 μl of 1× Tris buffer.

Final Amplification and Purification
60) Amplify the Hi-C library directly off of the T1 beads with 4-12 cycles, using Illumina primers and protocol. In some examples to avoid PCR inhibition, one can detach DNA from the streptavidin beads by heating at 98 C for 10 minutes after step 59 and then removing the beads with a magnet.)
61) After amplification is complete, bring the total library volume to 250 μl.
62) Separate on a magnet. Transfer the solution to a fresh tube and discard the beads.
63) Warm a bottle of AMPure XP beads to room temperature. Gently shake to resuspend the magnetic beads. Add 175 μl of beads to the PCR reaction (0.7× volumes). Mix by pipetting and incubate at room temperature for 5 minutes.
64) Separate on a magnet and remove the clear solution.
65) Keeping the beads on the magnet, wash once with 700 μl of 70% ethanol without mixing.
66) Remove ethanol completely. To remove traces of short products, resuspend in 100 μl of 1× Tris buffer and add 70 μl more of AMPure XP beads. Mix by pipetting and incubate at room temperature for 5 minutes.
67) Separate on a magnet and remove the clear solution.
68) Keeping the beads on the magnet, wash twice with 700 μl of 70% ethanol without mixing.
69) Leave the beads on the magnet for 5 minutes to allow remaining ethanol to evaporate.
70) Add 25-50 μl of 1× Tris buffer to elute DNA. Mix by pipetting, incubate at room temperature for 5 minutes, separate on a magnet, and transfer the solution to a freshly labeled tube. The result is a final in situ Hi-C library ready to be quantified and sequenced using an Illumina sequencing platform.

In situ Hi-C can be performed on cells embedded in agar plugs as follows:

After lysis (above protocol, step 11), nuclei can be resuspended in 100 μl 2×NEBuffer2 and mixed with 100 μl molten 2% NuSieve agarose (Lonza, 5009) and allowed to solidify into an agarose plug. The nuclei embedded in agar are restricted overnight in 500 μl 1×NEBuffer2 with 100 U of MboI at 37° C.

After restriction, the buffer is discarded and the agar plug is washed twice with 1 ml of 1×NEB T4 DNA ligase buffer for 30 min at 37° C. The buffer is discarded and the agar plug is submerged in 0.5 ml fill-in reaction mix:
   398 μl of water
   50 μl of 10×NEB T4 DNA ligase buffer
   37.5 μl of 0.4 mM biotin-14-dATP
   1.5 μl of 10 mM dCTP
   1.5 μl of 10 mM dGTP
   1.5 μl of 10 mM dTTP
   10 μl of 5 U/μl DNA Polymerase I, Large (Klenow) Fragment The library is incubated for 1.5 hours at room temperature. After incubation, 2000 U of T4 DNA Ligase are added to the reaction and the library is ligated at room temperature for 4 hours.

After ligation, the buffer is discarded and the agar plug is washed twice with 1 ml of 1×NEB β-agarase I buffer (NEB, B0392) for 30 min at 37° C. The buffer is removed and the agarose is melted by incubation at 68° C. for 10 minutes. Liquid agarose is equilibrated at 42° C. for 15 minutes. The agarose was digested with 4 U of β-Agarase I (NEB, M0392) at 42° C. for 1 hour. Next, the crosslinks can be reversed and all subsequent steps are performed following the standard in situ Hi-C protocol beginning at step 18.

In Situ Determination of Nucleic Acid Proximity as Determined by the Inventors for Cell Line GM12878.
Library complexity: 5,013,218,921
Inter: 26,989,930 (21.29%)
Intra: 99,786,882 (78.71%)
Small: 28,929,777 (22.82%)

Large: 70,857,049 (55.89%)
In Situ Determination of Nucleic Acid Proximity as Determined by the Inventors for Cell Line IMR-90.
Library Complexity: 4,539,616,093
Inter: 23,982,997 (19.20%)
Intra: 100,952,857 (80.80%)
Small: 25,712,979 (20.58%)
Large: 75,237,444 (60.22%)
Hi-C Methodology as Described in McCord et al., Genome Res. Vol. 23 No. 2, pp 260-269, 2013, which is Specifically Incorporated Herein by Reference in its Entirety (See Example 3)
Library complexity: 601,980,531
Inter: 11,681,267 (22.38%)
Intra: 40,503,943 (77.62%)
Small: 34,209,456 (65.55%)
Large: 6,292,643 (12.06%)
Hi-C Methodology as Described in Rickman et al., PNAS, USA, Vol. 109 No. 23, pp 9083-9088, 2012, which is Specifically Incorporated Herein by Reference in its Entirety (See Example 4).
Library complexity: 107,614,087
Inter: 17,204,445 (36.84%)
Intra: 29,500,589 (63.16%)
Small: 17,708,289 (37.92%)
Large: 11,783,647 (25.23%)

Example 3

Analysis of Human Fibroblasts Using Hi-C

This example describes the analysis of human fibroblasts using the Hi-C methodology as described in McCord et al., Genome Res. Vol. 23 no. 2, pp 260-269, 2013.

Cell Lines

The three primary fibroblast cell lines used in the Hi-C experiments were HGADFN167 (HGPS), HGFDFN168 (Father, normal), and AG08470 (Age control, normal). Additional fibroblast lines were used in EZH2 RT-qPCR analysis, and these cell lines were HGADFN169 (HGPS), HGADFN164 (HGPS), HGADFN155 (HGPS), and HGFDFN090 (normal). AG08470 was obtained from Coriell, and the other cell lines were obtained from the Progeria Research Foundation. These primary human dermal fibroblasts were cultured in MEM (Invitrogen/GIBCO) supplemented with 15% fetal bovine serum (FBS) (Invitrogen) and 2 mM L-glutamine.

Hi-C Library Preparation 20 million cells from an HGPS cell line (HGADFN167) at two increasing passages (p17 and 19), as well as from two normal fibroblast cell lines at similar passages (HGFDFN168-p18 and AG08470-p20) were crosslinked in 1% formaldehyde. HGFDFN168-p18 is the father of the HGPS patient HGADFN167, and AG08470 is an age matched, unrelated child. Hi-C was performed essentially as described previously (Lieberman-Aiden et al. 2009). Cells were lysed, and chromatin was digested with HindIII. Digested ends were filled in with biotinylated dCTP and then ligated for 4 hours at 16 C. After reversing the formaldehyde crosslinks by incubation at 65 C with Proteinase K overnight and removing unligated biotinylated ends with T4 DNA polymerase, the DNA was fragmented by Covaris sonication to an average size of 200 bp and then the ideal size for Illumina sequencing (100-300 bp) was selected by Ampure fractionation. The DNA ends were repaired and 'A'-tailed and then biotinylated junctions were pulled down using MyOne streptavidin beads. Illumina paired end adapters were ligated onto the DNA ends and then the fragments were PCR amplified for the minimum number of cycles necessary to generate 10 nM final DNA concentration.

Hi-C Data Processing

Samples were sequenced on an Illumina GAII instrument using the Paired End 75 bp module. Sequencing reads from the Hi-C experiment were mapped to the hg18 genome using Bowtie2 using the "very-sensitive" settings in an iterative procedure as follows: first, the 5' 25 bp of each sequence was mapped, and then any reads that were unmapped or not mapped uniquely were extended to 30 bp, then 35 bp, etc. until the maximum length of the sequence was reached. This procedure aids in mapping sequences that read through a ligation junction near their 3' end and whose full length sequence would thus be unmappable. Aligned reads were assigned to restriction fragments and filtered to discard duplicate read pairs (PCR over-amplification products) and molecules for which both ends map to the same restriction fragment.

Restriction fragments shorter than 100 bp or longer than 100 kb as well as those with the top 0.5% of read counts were removed. After these filtering steps, 10-20 million valid interaction pairs were obtained for each sample. Reads were assigned to genomic bins of 200 kb, according to the center of their corresponding restriction fragment. The binned interaction maps were then corrected for systematic biases by equalizing the total coverage (1D sum across the matrix) of every bin in the genome using 50 iterations of a normalization procedure previously described (Imakaev et al. 2012 Nat Methods; 9(10):999-1003; Zhang et al. 2012 Cell; 148(5):908-921). The final data was then smoothed with a 1 Mb bin size and 200 kb step size.

Hi-C Data Analysis and Comparison to Other Datasets

Open and closed chromatin compartments were identified as previously described (Lieberman-Aiden et al. 2009 Science. 326: 289-293). Briefly, the expected number of Hi-C reads between bins separated by each genomic distance was calculated using a loess-smoothed average over the dataset. The log ratio of observed Hi-C reads to this expected value was then calculated. The Pearson correlation between the patterns of chromosomal interactions at each pair of bins was then calculated, and this correlation matrix was used to perform Principal Components Analysis. The eigenvector of the first principal component was then plotted as the compartment assignment, with positive values corresponding to regions of high gene density ("compartment A" or "open chromatin") and negative values corresponding to regions of low gene density ("compartment B" or "closed chromatin"). The gene density was determined by calculating the number of genes in each bin according to the UCSC Known Canonical table of human genes.

Example 4

Analysis of Human Fibroblasts Using Hi-C

This example describes the analysis of RWPE1-ERG and RWPE1-GFP cell lines.

Human Cell Lines.

RWPE1 and DU145 cells were obtained from ATCC and maintained according to the manufacturer's protocol using isogenic cell lines overexpress either truncated ERG (most commonly encoded isoform based on TMPRSS2-ERG fusion).

Hi-C Library Generation.

Fifty million RWPE1-ERG or RWPE1-GFP cells were fixed and processed to generate Hi-C libraries. Briefly, cells were cross-linked and the chromatin was digested with HindIII, ligated after fill-in with biotin-conjugated dCTP, and purified using streptavidivin-conjugated magnetic beads. The Hi-C libraries were then paired-end sequenced using an Illumina GAIIx platform, resulting in replicate-combined 158.5 million and 159.2 million paired-end DNA sequence reads from RWPE1-ERG and RWPE1-GFP, respectively.

Hi-C

Fifty million RWPE1-ERG or RWPE1-GFP cells were fixed and processed to generate Hi-C libraries as previously reported. Briefly, cells were cross-linked, and the chromatin was digested with HindIII, ligated after fill-in with biotin-conjugated dCTP, and purified using streptavidivin-conjugated magnetic beads.

SI Computational Analysis

Sequence Alignment and Extraction of Hi-C Interactions. We aligned the two ends of the 54-bp paired reads separately to the reference human genome hg18 (NCBI build 36), using the BWA aligner.

Reads mapped ambiguously to multiple locations on the genome were discarded. We further filtered out clonal reads caused by PCR artifacts on the basis of the 5' and 3' read positions, removed nonligated DNA fragments, and retained ones with consistent expected placement relative to HindIII enzyme digestion sites. In total, we obtained more than 32 million intra- and interchromosomal interactions in each cell line.

Example 5

Hybrid Capture Hi-C

As implemented in this Example, the disclosed example embodiment involves generating a probe set to detect target ligation junctions, the probes in the probe set comprising one or more labeled nucleotides. The probes in the probe set are designed to target sequences within a certain distance of known restriction sites in the genome to be analyzed. Ligation junctions are formed as described previously with the exception that labeled nucleotides do not have to be incorporated to fill in the overhanging fragmented ends. The generated probe set is allowed to hybridize to the formed ligation junctions and the one or more labeled nucleotides in the hybridized probed are then used to isolate the one or more end joined nucleic fragments (junctions). To determine the sequence of the target junction is then determined using nucleic acid sequencing.

i. Probe Design

To design probes targeting a particular region for HYbrid Capture Hi-C (Hi-C$^2$), all restriction sites within the target region were identified. Since Hi-C ligation junctions occur between restriction sites, bait probe sequences were designed to target sequences within a certain distance of the identified restriction sites present in the target region. In this particular embodiment MboI restrictions sites were used. Specifically, a first pass was performed scanning all 120 bp sequences with one end within 80 bp of a restriction site and selecting, for each restriction end (i.e. both upstream and downstream of the restriction site), the closest 120 bp sequence to the restriction site that had fewer than 10 repetitive bases (as determined by the repeat masked hg19 genome downloaded from UCSC) and had between 50% and 60% GC content. If there was no probe satisfying those criteria, the closest probe with between 40% and 70% GC content but satisfying all the other above criteria was retained. The GC content bounds were chosen based on the hybridization bias data known in the art.

After the first pass, one probe from any pair of probes that overlapped was removed. Gaps in the probe coverage were identified, for example intervals larger than 110 bp, and any restriction sites falling within those gaps identified. Additional 120 bp probes were then searched using the following relaxed set of criteria. For each restriction site within a gap, all 120 bp sequences with one end within 110 bp of a restriction site were scanned and the closest sequence to the restriction site that had fewer than 20 repetitive bases and had between 40 and 70% GC content was selected. After the second pass, gaps in the probe coverage of at least 110 bp were identified. For gaps that fell within 5 kb windows in the target region that were covered by fewer than 5 probes, a third probe design pass was performed. For each restriction site within these low coverage gaps, all 120 bp sequences with one end within 110 bp of a restriction site were scanned and the closest sequence to the restriction site that had fewer than 25 repetitive bases and had between 25% and 80% GC content was selected.

ii. Probe Construction

Custom synthesized pools of 150 bp (120 bp+15 bp primer sequence on either end) single stranded oligodeoxy-nucleotides were obtained from CustomArray, Inc. (Bothell, Wash.). The oligonucleotides were of the general form TCGCGCCCATAACTCN$_{120}$CTGAGGGTCCGCCTT (SEQ ID NO: 1) for Region 1, ATCGCACCAGCGTGTN$_{120}$CACTGCGGCTCCTCA (SEQ ID NO: 2) for Region 2, and CCTCGCCTATCCCATN$_{120}$CACTACCGGGGTCTG (SEQ ID NO: 3) for Region 3. Region-specific sub-pools were first amplified from the overall CustomArray oligo pool using the following mix and PCR profile:

| | |
|---|---|
| 2 ul | oligo pool (160 ng) |
| 6 ul | Primer 1 (10 uM) |
| 6 ul | Primer 2 (10 uM) |
| 36 ul | H2O |
| 50 ul | 2X Phusion master mix |
| 100 ul | TOTAL |

Amplify for 10-18 cycles using the following PCR profile:

| |
|---|
| 98 C. for 30 s |
| 98 C. for 10 s |
| 55 C. for 30 s |
| 72 C. for 30 s cycle 10-18 times |
| 72 for 7 min |
| hold at 4 C. | where Primer 1 was CTGGGATCGCGCCCATAACTC (SEQ ID NO: 4) for Region 1, CTGGGAATCGCACCAGCGTGT (SEQ ID NO: 5) for Region 2, CTGGGACCTCGCCTATCCCAT (SEQ ID NO: 6) for Region 3 and Primer 2 was CGTGGAAAGGCGGACCCTCAG (SEQ ID NO: 7) for Region 1, CGTGGATGAGGAGCCGCAGTG (SEQ ID NO: 8) for Region 2, CGTGGACAGACCCCGGTAGTG (SEQ ID NO: 9) for Region 3.

After the initial amplification of the region-specific sub-pool, a 1×SPRI clean up was performed on the 162 bp PCR product to remove primers and primer-dimers. We then performed a second PCR amplification to add a T7 promoter, using the following mix and PCR profile:

| | |
|---|---|
| 2 ul | first PCR product |
| 12 ul | Primer 1 - T7 (10 uM) |
| 12 ul | Primer 2 (10 uM) |
| 74 ul | H2O |
| 100 ul | 2X Phusion master mix |
| 200 ul | TOTAL |

Amplify for 12-18 cycles using the following PCR profile:

| |
|---|
| 98 C. for 30 s |
| 98 C. for 10 s |
| 55 C. for 30 s |
| 72 C. for 30 s cycle 12-18 times |
| 72 for 7 min |
| hold at 4 C. | where Primer 1-T7 was GGATTCTAATACGACTCACTATAGGGTCGCGCCCATAACTC (SEQ ID NO: 10) for Region 1, GGATTCTAATACGACTCACTATAGGGATCGCACCAGCGTGT (SEQ ID NO: 11) for Region 2, and GGATTCTAATACGACTCACTATAGGGCCTCGCCTATCCCA (SEQ ID NO: 12) for Region 3.

After the second PCR, once again, a 1×SPRI clean up to purify the 182 bp PCR product was performed. The purified second PCR product was then used as the template in a MAXIScript T7 transcription reaction (Ambion) as follows:

| | |
|---|---|
| X ul | purified DNA template (1 ug) |
| 10 ul | T7 enzyme mix |
| 10 ul | 10X transcription buffer |
| 5 ul | 10 mM ATP |
| 5 ul | 10 mM CTP |
| 5 ul | 10 mM GTP |
| 4 ul | 10 mM UTP |
| 1 ul | 10 mM Biotin-16-UTP |
| Y ul | H2O |
| 100 ul | TOTAL |

After incubating the reaction for at least 90 minutes at 37 C, 1 ul of TURBO DNase 1 was added and incubated at 37° C. for 15 minutes to remove template DNA. An aliquot of 1 ul of 0.5M EDTA was added to stop the reaction and unincorporated nucleotides were removed and the RNA desalted by purifying the RNA probes using a Zymo Oligo Clean and Concentrator column (following manufacturer's instructions). The RNA yield was typically 5-15 ug of RNA per reaction, so the concentration of the RNA prior to the column cleanup using a Qubit RNA assay was measured in order to determine whether to use one or two columns (the capacity of one of the Zymo columns is 10 ug). For long-term storage of the RNA probes, 1 U/ul of SUPERase-In RNase inhibitor (Ambion) was added and the probes were stored at −80 C.

iii. Hybrid Selection

Final in situ Hi-C libraries were assessed for quality using the metrics outlined in Rao et al. Cell. 2014 159(7):1665-80. High quality libraries of sufficient complexity were selected for hybrid capture. 500 ng of Hi-C library was used as the pond for the hybrid selection reaction; libraries were diluted to a concentration of 20 ng/ul (i.e. 25 ul of library was used). For a few libraries that were under 20 ng/ul in concentration, as low as 250 ng total was used (still in 25 ul).

For the hybridization reaction, 25 ul of pond was mixed with 2.5 ug (1 ul) of Cot-1 DNA (Invitrogen) and 10 ug (1 ul) of salmon sperm DNA (Stratagene). The DNA mixture was heated to 95 C for 5 minutes and then held at 65 C for at least 5 minutes. After at least 5 minutes at 65 C, 33 ul of prewarmed (65 C) hybridization buffer (10×SSPE, 10×Denhardt's buffer, 10 mM EDTA, and 0.2% SDS) and 6 ul of RNA probe mixture (500 ng of RNA probes, 20 U of SUPERase-In RNase inhibitor; prewarmed at 65 C for 2 minutes) were added to the DNA library for a total volume of ~66 ul. This mixture was incubated at 65 C in a thermocycler for 24 hours.

After 24 hours at 65 C, 50 ul of streptavidin beads (Dynabeads MyOne Streptavidin T1, Life Technologies) were washed three times in 200 ul of Bind-and-Wash buffer (1M NaCl, 10 mM Tris-HCl, pH 7.5, and 1 mM EDTA) and then resuspended in 134 ul of Bind-and-Wash buffer. The beads were added to the hybridization mixture and incubated for 30 minutes at room temperature (with occasional mixing to prevent the beads from settling). After 30 minutes, the beads were separated with a magnet and the supernatant discarded. The beads were then washed once with 200 ul low-stringency wash buffer (1×SSC, 0.1% SDS) and incubated for 15 minutes at room temperature. After 15 minutes, the beads were separated on a magnet and the supernatant discarded. The beads were then washed three times in high-stringency wash buffer (0.1×SSC, 0.1% SDS) at 65 C for 10 minutes, each time separating the beads with a magnet and discarding the supernatant.

After the last wash, the DNA was eluted off the beads by resuspending in 50 ul of 0.1M NaOH and incubating for 10 minutes at room temperature. After 10 minutes, the beads were separated on a magnet and the supernatant was transferred to a fresh tube with 50 ul of 1M Tris-HCl, pH 7.5 (to neutralize the NaOH).

To desalt the DNA, we performed a 1×SPRI cleanup using 3× concentrated SPRI beads (taking 3 volumes of SPRI bead/solution mix, separating on a magnet, discarding 2 volumes of SPRI solution and resuspending the beads in the remaining 1 volume). We eluted the DNA in 22.5 ul of 1× Tris buffer (10 mM Tris-HCl, pH 8.0).

In order to prep the Hi-$C^2$ library for sequencing, we added 25 ul of 2× Phusion and 2.5 ul of Illumina primers and amplified the library for 12-18 cycles. After PCR, we performed two 0.7×SPRI cleanups to remove primers, etc. and then quantified the libraries for sequencing.

iv. Hi-$C^2$ Data Processing

Hi-C2 libraries were sequenced to a depth of between ~600K-60M reads (on average, 7.8M reads). All data was initially processed using the pipeline published in Rao et al. (Cell vol. 159, 7 (2014): 1665-80). However, additional processing was needed to properly normalize the Hi-C2 data.

Normalization is an important problem to address in the analysis and interpretation of all proximity ligation experiments. It was previously shown that matrix balancing with the KR algorithm is an effective tool for properly normalizing Hi-C data (Rao and Huntley, et al. Cell vol. 159, 7 (2014): 1665-80). However, one requirement of the KR algorithm is the requirement of a square symmetric matrix. As hybrid selection strongly enriches for certain rows of the matrix corresponding to the target region, there are large regions of the overall matrix that are extremely sparse (entries corresponding to interactions between two non-target loci). As a result, performing KR matrix balancing on the overall matrix generated by a Hi-C2 experiment does not efficiently correct both first-order hybrid selection target-enrichment biases and second-order hybridization biases within the target region.

To deal with this, a previously generated high resolution genome-wide in situ Hi-C map of wild-type of Hap1 was used to normalize the data. Since all genome-editing perturbations were made within the region targeted using Hi-C$^2$, for every Hi-C$^2$ dataset, data from the genome-wide wild-type Hap1 map corresponding to regions of the chromosome-wide matrix where both loci fall outside of the target region were spiked in. Spiked data was added such that the average coverage of a locus in the overall chromosome-wide matrix was equal to the average coverage of loci within the target region. By spiking in data from the wild-type map where expectation is to see no change (since there were no perturbations), the first-order bias from hybrid-selection target enrichment could be removed, and KR matrix balancing used on the entire chromosome-wide matrix (which is no longer extremely sparse) to correct the second-order hybridization biases. Several different flavors of this normalization scheme may be implemented yielding extremely similar results; they are described below. The example methods described below may be used to normalize the data.

a. Raw gap-filling: For a given resolution, the average intrachromosomal coverage of the loci within the target region (defined as the entire interval tiled by probes not specifically the loci that were covered by a probe) was calculated from the raw uncorrected Hi-C$^2$ matrix. Similarly, the average intrachromosomal coverage of all loci was calculated from the raw uncorrected genome-wide Hap1 wild-type Hi-C map. A matrix consisting of all entries corresponding to two loci that were both outside the target region was constructed from the raw uncorrected genome-wide Hap1 Hi-C map. This matrix was multiplied by the ratio of the average coverage of loci within the target region in the Hi-C$^2$ data to the average coverage of all loci from the genome-wide Hap1 wild-type Hi-C data and then summed with the Hi-C$^2$ matrix (thereby filling in the extremely sparse areas of the Hi-C$^2$ matrix). This summed matrix was then corrected with the KR matrix balancing algorithm. The resulting normalization factors were used as correction factors for the Hi-C$^2$ data.

b. KR gap-filling: The KR gap-filling normalization was performed similarly to the method described above, but to avoid corrected Hi-C biases and Hi-C$^2$ biases together, the method above was performed on KR normalized data. Specifically, the KR correction factors derived from the genome-wide Hap1 wild-type Hi-C map were used to perform an initial correction of the Hi-C$^2$ data. After the initial correction, the average intrachromosomal coverage of the loci within the target region (defined as the entire interval tiled by probes not specifically the loci that were covered by a probe) was calculated from the Hi-C$^2$ matrix. Similarly, the average intrachromosomal coverage of all loci was calculated from the corrected genome-wide Hap1 wild-type Hi-C map. A matrix consisting of all entries corresponding to two loci that were both outside the target region was constructed from the raw uncorrected genome-wide Hap1 Hi-C map. This matrix was multiplied by the ratio of the average coverage of loci within the target region in the Hi-C$^2$ data to the average coverage of all loci from the genome-wide Hap1 wild-type Hi-C data and then summed with the Hi-C$^2$ matrix (thereby filling in the extremely sparse areas of the Hi-C$^2$ matrix). This summed matrix was then corrected with the KR matrix balancing algorithm. The resulting normalization factors may be used as correction factors for the Hi-C$^2$ data.

c. Raw gap-filling with rescaling: Filling in the sparse areas of the Hi-C$^2$ matrix corrects for first order target enrichment biases from hybrid capture to some extent, but does not account for the fact that differential enrichments may be present for entries of the matrix corresponding to one on-target loci and one off-target loci vs. entries corresponding to two on-target loci. To address this, the ratio of the number of contacts formed between the locus and off-target loci to the number of contacts formed between the locus and other on-target loci using the genome-wide Hap1 wild-type Hi-C data was first calculated before performing gap-filling as in the above methods. The same ratio was then calculated using the Hi-C$^2$ data. The ratio of these ratios provided a scaling factor for each on-target locus which was then used to scale all entries in the Hi-C$^2$ matrix corresponding to contacts between the on-target locus and off-target loci. After performing this correction, the method from above was followed, i.e. a matrix consisting of all entries corresponding to two loci that were both outside the target region was constructed from the raw uncorrected genome-wide Hap1 Hi-C map. This matrix was multiplied by the ratio of the average coverage of loci within the target region in the Hi-C$^2$ data (using the rescaled Hi-C$^2$ data) to the average coverage of all loci from the genome-wide Hap1 wild-type Hi-C data and then summed with the Hi-C$^2$ matrix (thereby filling in the extremely sparse areas of the Hi-C$^2$ matrix). This summed matrix was then corrected with the KR matrix balancing algorithm. The resulting normalization factors were used as correction factors for the Hi-C$^2$ data.

d. KR gap-filling with rescaling: This method is the same as method c, except that as in method b, the Hi-C$^2$ data was initially corrected with the KR factors derived from the Hap1 genome-wide wild-type Hi-C matrix and the KR corrected wild-type Hi-C data was used for gap-filling.

e. Raw gap-filling with rescaling and thresholding: It was noted that for a few very sparse (under-covered) rows in the Hi-C$^2$ data, the normalization methods would actually overcorrect, leading to highly-covered streak artifacts in the data. In order to remove these artifacts, a final filtering step was added where loci with a normalization factor (C) of less than 0.33 (where $M_{i,j}$ is divided by $C_i$ and $C_j$ to get the corrected entry $M^*_{i,j}$) were thresholded so that their normalization factors were raised to 0.33 (this was implemented after the KR matrix balancing was run, not as a constraint during the running of the algorithm). The threshold of 0.33 was chosen based on empirical observation of rows that led to streaky artifacts. This method is the same as method c except with the aforementioned thresholding.

f. KR gap-filling with rescaling and thresholding: This method is the same as method d except with the addition of the thresholding described in method e.

Example 6

Genome Engineering Workflow

As described in this example, the example method comprises (i) identifying chromatin loops (ii) identifying unique, correctly oriented CTCF motifs within loop anchors (iii) rationally designing a CRISPR guide RNA or multiple guide RNAs to cut within or around the CTCF motif while optimizing for cutting efficiency and minimizing off-target effects, (iv) optionally designing homology directed repair (HDR) templates to specifically invert or replace the CTCF motif, (v) transfecting cells with the Cas9 and the guide RNA(s) (and optionally the HDR template), (vi) sorting single transfected cells via fluorescence-activated cell sorting (FACS), (vii) growing up and genotyping clonal populations of cells, (viii) selecting clonal cell lines with mutations disrupting the CTCF motif (or in the case of HDR, the specific desired mutation), (ix) performing in situ Hi-C on the selected mutated cell lines, and (x) performing hybrid selection on the in situ Hi-C libraries for a region around the targeted CTCF motif to generate Hi-C$^2$ libraries that can easily and cheaply be sequenced to read off the effects of the mutations on genome folding.

While the CRISPR experiments where performed in the Hap1 cell line in order to read off the effects of the mutations without having to worry about allelic heterozygosity, this method is easily adaptable to other cell lines, as long as one has a reasonable means for identify chromatin loops. The steps in our workflow are described in detail below. Likewise this method may be adapted to modify regulatory elements other than CTCF motifs.

i. Experimental Design

Three regions containing triple-hubs (three loci A, B and C with all pair-wise loops present) were chosen for thorough dissection. The regions were chosen such that they showed extremely similar patterns of chromatin folding to GM12878 and IMR90, so that ChIP-Seq data from those cell lines could be used to identify precise motifs in loop anchors to target as well as to simulate folding in the regions.

The three hubs were chosen such that unique anchors (as defined in Rao and Huntley, et al. [Cell vol. 159, 7 (2014): 1665-80]) were present at least at the middle loop anchor and ideally at one of the upstream or downstream loop anchors as well. Motifs in loop anchors were identified using FIMO (Grant et al. Bioinformatics 2011; 27(7):1017-1018) using the CTCF motif position weight matrices (PWMs) from Kim, et al. (Cell 2007; 128(6):1231-1245) and Schmidt, et al. (Cell 2012; 148(1-2):335-348). The hubs were chosen such that all loops were clearly anchored by correctly oriented motifs. Motifs to target via CRISPR were only chosen if they were clearly unique among the correctly oriented motifs in a ChIP-Seq binding site (i.e. there was only one motif present or only one motif that was clearly the strongest match when compared against both PWMs and in the case of the middle loop anchor, the reverse CTCF motif corresponding to the A-B loop was upstream of the forward CTCF motif corresponding to the B-C loop).

ii. Guide RNA and HDR Template Design

Guide RNAs were designed using one of two strategies. Either a single guide RNA was designed to cut inside the target CTCF motif, or two guide RNAs were designed to cut both sides flanking the target CTCF motif.

Prospective guide RNAs were screened using the cutting efficiency scoring schemes known in the art. Wherever possible, guides with cutting efficiency scores of 0.4 or lower were avoided, and guide RNAs with scores of lower than 0.25 were discarded altogether. Wherever possible, guides ranked as high quality guides by the Hsu off target assessment algorithm were used. In a few cases, where no high quality guide was identified or when the cutting efficiency as ranked by the Doench, et al algorithm was extremely low, a mid-quality guide (with respect to off-targets) was used.

All the HDR templates used in this study were ssODNs (Ran et al., *Nature protocols vol.* 8, 11 (2013): 2281-2308), either 200 bp (IDT ultramers) or 100 bp (Invitrogen custom DNA oligonucleotides) in size. They were designed such that they contained the 20 bp CTCF motif inverted (or a new 20 bp CTCF motif), flanked by homology arms either 90 bp or 40 bp in size.

iii. Cell Culture and Transfection

Hap1 cells (Horizon Genomics) were cultured according to manufacturer's conditions. 24 hours before transfection, 0.9M Hap1 cells were plated in each well of a 6 well plate. After 24 hours, when the cells were roughly 60% confluent, the cells were transfected with the pSpCas9(BB)-2A-GFP (px458) plasmid. Guide RNAs were cloned into the plasmid using known protocols.

The Hap1 cells were transfected (in antibiotic free media) with 3 ug of DNA using Turbofectin according to manufacturer's instructions (a 3:1 ratio of Turbofectin to DNA was used; 9 ul of Turbofectin for 3 ug of DNA). For single guide RNAs, 3 ug of the Cas9-gRNA plasmid was used. For double guide RNA mediated deletions, 1.5 ug of each Cas9-gRNA plasmid was used. For HDR, either 1.5 ug of Cas9-gRNA plasmid and 3 ul 10 uM 200 bp ssODN or 1.875 ug Cas9-gRNA plasmid and 3.75 ul 10 uM 100 bp ssODN were used. For HDR experiments, the culture media was supplemented with 0.1 uM SCR7 (Chu et al., Nat Biotech 2015; 33(5):543-548, Maruyama et al., Nat Biotech 2015; 33(5):538-542) 12-24 hours after transfection.

24-48 hours after transfection, GFP$^+$ cells were sorted via FACS (PI was also added to filter for dead cells). Transfection efficiencies were usually between 5 and 10%. Populations of 500-10,000 cells were screened for gRNA cutting efficiency or for HDR efficiency to judge roughly how many clones would need to be screened. Single cells were sorted into individual wells of a 96-well plate and allowed to grow for 10-14 days. After that, roughly 32-96 clones were screened per transfection.

iv. Mutation Strategy

Deletions were obtained either via a single guide RNA-mediated cut within the CTCF motif or via two guide RNAs-mediated double strand breaks on either side of the CTCF motif. In the case of the single guide RNA mediated cuts, clones were screened for mutations that were as small as possible, but also highly likely to completely disrupt CTCF binding (as judged by the strength of the motif match before and after mutation). Mutations that were likely to completely abrogate CTCF binding were selected for expansion. Mutations generated via two double strand breaks were all generated by Horizon Genomics and clones containing the region between the two guide RNAs either cut out or inverted were selected for expansion. Clones targeted with HDR were screened for the 20 bp inversion or 20 bp replacement and successfully targeted clones were selected for expansion.

v. In Situ Hi-C on Mutated Cell Lines

Expanded mutant clones were crosslinked and subsequently in situ Hi-C was performed on the pellets as described herein. On average, 4.3 in situ Hi-C libraries were generated per mutated cell line for a total of 56 in situ Hi-C libraries.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of this disclosure and these claims.

We claim:

1. A method for altering one or more chromatin loops anchored on a loop anchor of one or more specific genomic regions of a chromosome in one or more cells of a cell type from a sample, wherein the sample is from an organ or a tissue or primary cells or cultured cells, said method comprising:

introducing one or more CRISPR/Cas systems into the one or more cells of the cell type from the sample, wherein the one or more CRISPR/Cas systems target a region within or around a pair of convergent CTCF motifs on one or more specific genomic regions of a chromosome in the one or more cells of the cell type, wherein the one or more specific genomic regions of the chromosome in the one or more cells of the cell type comprise one or more chromatin loops, wherein the one or more chromatin loops are identified using a chromosome conformation capture technology and are anchored on a loop anchor comprising the pair of convergent CTCF motifs on the one or more specific genomic regions of the chromosome in the one or more cells of the cell type, and wherein the one or more CRISPR/Cas systems are CRISPR/Cas RNA-guided DNA endonuclease systems, wherein said introducing one or more CRISPR/Cas systems into the one or more cells of the cell type introduces a CTCF motif into the loop anchor of the one or more specific genomic regions of the chromosome in the one or more cells of the cell type or wherein said introducing one or more CRISPR/Cas systems into the one or more cells of the cell type removes a CTCF motif from the pair of convergent CTCF motifs on the loop anchor of the one or more specific genomic regions of the chromosome in the one or more cells of the cell type, whereby the one or more chromatin loops anchored on the loop anchor of the one or more specific genomic regions of the chromosome in the one or more cells of the cell type are altered.

2. The method of claim 1, wherein the pair of convergent CTCF motifs comprises a consensus DNA sequence 5'-CCACNAGGTGGCAG-3'.

3. The method of claim 1, wherein at least one base in the pair of convergent CTCF motifs is mutated.

4. The method of claim 1, wherein the CTCF motif is introduced into the loop anchor of the one or more specific genomic regions of the chromosome in the one or more cells of the cell type in an inverted orientation.

5. The method of claim 4, wherein a new chromatin loop is generated from the CTCF motif in the inverted orientation on the loop anchor.

6. The method of claim 1, further comprising introducing two CTCF motifs in a convergent orientation into the loop anchor of the one or more specific genomic regions of the chromosome in the one or more cells of the cell type using one or more CRISPR/Cas systems targeting a region within or around the pair of convergent CTCF motifs on the one or more specific genomic regions of the chromosome in the one or more cells of the cell type such that a new chromatin loop is established.

7. The method of claim 1, wherein the chromosome conformation capture technology is a Hi-C technique and generates a Hi-C heatmap, and pairs of loci that show significantly closer proximity with one another than with the loci lying between the pairs of loci in the Hi-C heatmap are peak loci and represent loop anchors.

8. The method of claim 7, further comprising comparing the peak loci with gene expression data obtained from the one or more cells of the cell type, wherein the specific genomic regions are actively transcribed regions.

9. The method of claim 1, wherein the one or more chromatin loops are involved in the regulation of the expression of a gene.

10. The method of claim 9, wherein the one or more chromatin loops link a promoter and a regulatory element.

11. The method of claim 10, wherein the regulatory element is an enhancer.

12. The method of claim 1, wherein the one or more specific genomic regions is associated with a disease or condition.

13. The method of claim 12, wherein the one or more cells of the cell type are associated with the disease or condition.

14. The method of claim 12, wherein the one or more chromatin loops are associated with the regulation of a gene associated with the disease or condition.

15. The method of claim 1, wherein said introducing the one or more CRISPR/Cas systems into the one or more cells of the cell type comprises delivering one or more vectors encoding the one or more CRISPR/Cas systems into the one or more cells of the cell type.

16. The method of claim 15, wherein the vectors comprise a tissue-specific promoter.

17. The method of claim 1, wherein said introducing the one or more CRISPR/Cas systems into the one or more cells of the cell type comprises delivering a cell-permeable reagent, a pyrrole-imidazole polyamide, into the one or more cells of the cell type.

18. The method of claim 1, wherein the CRISPR/Cas systems comprise a nickase.

19. The method of claim 1, wherein the CRISPR/Cas systems comprise one or more homology directed repair (HDR) templates.

20. The method of claim 1, further comprising performing in situ Hi-C technique on said one or more cells of the cell type following said introducing the CRISPR/Cas systems into the one or more cells of the cell type such that an in situ Hi-C library is generated, optionally performing a HYbrid Capture technique after the in situ Hi-C library is generated.

21. The method of claim 20, further comprising generating cell clones by culturing the one or more cells of the cell type after said introducing the one or more CRISPR/Cas systems into the one or more cells of the cell type and selecting cell clones having the altered chromatin loops.

22. The method of claim 21, wherein the cell clones are screened for a specific phenotype.

23. The method of claim 1, further comprising generating cell clones by culturing the one or more cells of the cell type after said introducing the CRISPR/Cas systems into the one or more cells of the cell type and selecting cell clones having a desired expression of one or more genes.

24. The method of claim 1, wherein the one or more cells of the cell type are animal or plant cells.

25. The method of claim 1, wherein the one or more chromatin loops are less than 2 Mb.

* * * * *

UNITED STATES PATENT AND TRADEMARK OFFICE
CERTIFICATE OF CORRECTION

PATENT NO. : 11,279,974 B2
APPLICATION NO. : 15/532353
DATED : March 22, 2022
INVENTOR(S) : Erez Lieberman-Aiden et al.

It is certified that error appears in the above-identified patent and that said Letters Patent is hereby corrected as shown below:

In the Specification

In Column 4, Line 60, delete "HDAD-Igf2" and insert -- HIDAD-Igf2 --.

In Column 5, Line 13, delete "Bartlet," and insert -- Bartlett, --.

In Column 6, Line 1, delete "in" and insert -- on --.

In Column 8, Line 11, delete "2,2'disulfonic" and insert -- 2,2'-disulfonic --.

In Column 8, Line 15, delete "3,5 disulfonate" and insert -- 3,5-disulfonate --.

In Column 8, Lines 18-19, delete "7-amino-4-trifluoromethylcouluarin (Coumaran" and insert -- 7-amino-4-trifluoromethylcoumarin (Coumarin --.

In Column 8, Lines 19-20, delete "4',6-diaminidino-2-phenylindole" and insert -- 4',6-diamidino-2-phenylindole --.

In Column 8, Line 24, delete "di sulfonic" and insert -- disulfonic --.

In Column 8, Line 40, delete "(Cibacron™." and insert -- (Cibacron™ --.

In Column 8, Line 53, delete "-6-carboxy-fluorescein" and insert -- 6-carboxy-fluorescein --.

In Column 9, Line 16, delete "and or" and insert -- and/or --.

In Column 9, Line 45, delete "to" and insert -- two --.

In Column 9, Line 47, delete "where" and insert -- were --.

Signed and Sealed this
Eighth Day of August, 2023

Katherine Kelly Vidal
*Director of the United States Patent and Trademark Office*

CERTIFICATE OF CORRECTION (continued)
U.S. Pat. No. 11,279,974 B2

In Column 9, Line 48, delete "liner" and insert -- linear --.

In Column 10, Line 14, delete "5-(carboxyhydroxylmethyl)" and insert
-- 5-(carboxyhydroxymethyl) --.

In Column 10, Lines 16-17, delete "beta-D-galactosylqueosine," and insert
-- beta-D-galactosylqueuosine, --.

In Column 10, Line 17, delete "N~6-sopentenyladenine," and insert -- N-6-isopentenyladenine, --.

In Column 10, Lines 21-22, delete "methoxyarninomethyl-2-thiouracil, beta-D-mannosylqueosine,"
and insert -- methoxyaminomethyl-2-thiouracil, beta-D-mannosylqueuosine, --.

In Column 10, Line 24, delete "queosine," and insert -- queuosine, --.

In Column 10, Line 37, delete "phosphordiamidate," and insert -- phosphorodiamidate, --.

In Column 11, Line 20, delete "Wiley-Intersciences." and insert -- Wiley-Interscience. --.

In Column 11, Line 33, delete "Wiley-Intersciences" and insert -- Wiley-Interscience --.

In Column 11, Line 42, delete "50" and insert -- 50, --.

In Column 12, Line 43, delete "that that" and insert -- that --.

In Column 12, Line 51, delete "nodes" and insert -- nodes, --.

In Column 12, Line 65, delete "2d" and insert -- 2nd --.

In Column 12, Line 67, delete "3d" and insert -- 3rd --.

In Column 13, Line 11, delete "limiting" and insert -- limiting. --.

In Column 14, Line 1, delete "chromosome" and insert -- Chromosome --.

In Column 16, Line 17, delete "with out" and insert -- without --.

In Column 17, Line 41, delete "permeablized" and insert -- permeabilized --.

In Column 17, Lines 61-62, delete "gluteraldehyde." and insert -- glutaraldehyde. --.

In Column 18, Line 28, delete "reversible-, such" and insert -- reversible cross-linker, such --.

In Column 20, Line 48, after "will" insert -- be --.

In Column 21, Line 34, delete "RNAse" and insert -- RNase --.

CERTIFICATE OF CORRECTION (continued)
U.S. Pat. No. 11,279,974 B2

In Column 23, Line 57, delete "then" and insert -- than --.

In Column 24, Line 18, delete "(2013))" and insert -- (2013)). --.

In Column 26, Line 5, delete "190" and insert -- 190, --.

In Column 26, Line 8, delete "then" and insert -- than --.

In Column 26, Line 15, delete "190" and insert -- 190, --.

In Column 28, Line 46, delete "Xchromosome" and insert -- X-chromosome --.

In Column 29, Line 12, delete "highthroughput" and insert -- high-throughput --.

In Column 29, Line 28, delete "longrange" and insert -- long-range --.

In Column 29, Line 36, delete "Xchromosome" and insert -- X-chromosome --.

In Column 30, Lines 26-27, delete "Blymphoblasts" and insert -- B-lymphoblasts --.

In Column 30, Line 35, delete "(FIG." and insert -- (FIGS. --.

In Column 32, Line 27, delete "FIG." and insert -- FIGS. --.

In Column 32, Line 34, delete "(FIG." and insert -- (FIGS. --.

In Column 32, Line 57, delete "H4K20 me3." and insert -- H4K20me3. --.

In Column 33, Line 9, delete "Note," and insert -- note, --.

In Column 34, Line 2, delete "(FIG." and insert -- (FIGS. --.

In Column 34, Line 39, delete "75B)." and insert -- 7B). --.

In Column 35, Line 36, delete "(FIG." and insert -- (FIGS. --.

In Column 36, Line 27, delete "(Fig." and insert -- (Figs. --.

In Column 37, Line 46, delete "highthroughput" and insert -- high-throughput --.

In Column 38, Line 42, delete "basepairs," and insert -- base pairs, --.

In Column 38, Line 45, delete "al" and insert -- al., --.

In Column 38, Line 48, delete "OligoPaints" and insert -- Oligopaints --.

CERTIFICATE OF CORRECTION (continued)
U.S. Pat. No. 11,279,974 B2

In Column 40, Line 25, delete "In" and insert -- in --.

In Column 40, Line 31, delete "contacts/datapoints" and insert -- contacts/data points --.

In Column 42, Line 22, delete "μl" and insert -- μl. --.

In Column 43, Line 66, delete "98 C" and insert -- 98° C. --.

In Column 43, Line 67, delete "magnet.)" and insert -- magnet. --.

In Column 45, Line 12, delete "3)" and insert -- 3). --.

In Column 45, Line 49, delete "19)," and insert -- p19), --.

In Column 45, Line 58, delete "16" and insert -- 16° --.

In Column 45, Line 59, delete "65 C" and insert -- 65° C. --.

In Column 45, Line 63, delete "Ampure" and insert -- AMPure --.

In Column 46, Line 4, delete "GAII" and insert -- GAIIx --.

In Column 46, Line 7, delete "Bowtie2" and insert -- Bowtie 2 --.

In Column 47, Line 1, delete "streptavidivin-conjugated" and insert -- streptavidin-conjugated --.

In Column 47, Lines 12-13, delete "streptavidivin-conjugated" and insert
-- streptavidin-conjugated --.

In Column 47, Line 47, delete "HYbrid" and insert -- Hybrid --.

In Column 48, Line 46, delete "98" and insert -- 98° --.

In Column 48, Line 47, delete "98" and insert -- 98° --.

In Column 48, Line 48, delete "55" and insert -- 55° --.

In Column 48, Line 49, delete "72" and insert -- 72° --.

In Column 48, Line 50, delete "72" and insert -- 72° C. --.

In Column 48, Line 51, delete "4" and insert -- 4° --.

In Column 49, Line 13, delete "98" and insert -- 98° --.

In Column 49, Line 14, delete "98" and insert -- 98° --.

CERTIFICATE OF CORRECTION (continued)
U.S. Pat. No. 11,279,974 B2

In Column 49, Line 15, delete "55" and insert -- 55° --.

In Column 49, Line 16, delete "72" and insert -- 72° --.

In Column 49, Line 17, delete "72" and insert -- 72° C. --.

In Column 49, Line 18, delete "4" and insert -- 4° --.

In Column 49, Lines 42-43, delete "37 C," and insert -- 37° C., --.

In Column 49, Line 56, delete "-80 C." and insert -- - 80° C. --.

In Column 50, Line 2, delete "95 C" and insert -- 95° C. --.

In Column 50, Line 2, delete "65 C" and insert -- 65° C. --.

In Column 50, Line 3, delete "65 C," and insert -- 65° C., --.

In Column 50, Line 4, delete "(65 C)" and insert -- (65° C.) --.

In Column 50, Line 7, delete "65 C" and insert -- 65° C. --.

In Column 50, Line 9, delete "65 C" and insert -- 65° C. --.

In Column 50, Line 11, delete "65 C," and insert -- 65° C., --.

In Column 50, Line 25, delete "65 C" and insert -- 65° C. --.

SEQUENCE LISTING

<160> NUMBER OF SEQ ID NOS: 16

<210> SEQ ID NO 1
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: N_region
<222> LOCATION: (16)..(17)
<223> OTHER INFORMATION: "n" at position 16 represents any repeating or
      combination of nucleotides running for a length of 120 residues
<220> FEATURE:
<221> NAME/KEY: misc_feature
<222> LOCATION: (16)..(16)
<223> OTHER INFORMATION: n is a, c, g, or t

<400> SEQUENCE: 1
tcgcgcccat aactcnctga gggtccgcct t                                31

<210> SEQ ID NO 2
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: N_region
<222> LOCATION: (16)..(17)
<223> OTHER INFORMATION: "n" at position 16 represents any repeating or
      combination of nucleotides running for a length of 120 residues
<220> FEATURE:
<221> NAME/KEY: misc_feature
<222> LOCATION: (16)..(16)
<223> OTHER INFORMATION: n is a, c, g, or t

<400> SEQUENCE: 2
atcgcaccag cgtgtncact gcggctcctc a                                31

<210> SEQ ID NO 3
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: N_region
<222> LOCATION: (16)..(17)
<223> OTHER INFORMATION: "n" at position 16 represents any repeating or
      combination of nucleotides running for a length of 120 residues
<220> FEATURE:
<221> NAME/KEY: misc_feature
<222> LOCATION: (16)..(16)
<223> OTHER INFORMATION: n is a, c, g, or t

<400> SEQUENCE: 3
cctcgcctat cccatncact accggggtct g                                31

<210> SEQ ID NO 4
<211> LENGTH: 21
<212> TYPE: DNA
<213> ORGANISM: Artificial Sequence
<220> FEATURE:
<223> OTHER INFORMATION: Synthetic primer

<400> SEQUENCE: 4
ctgggatcgc gcccataact c                                           21

<210> SEQ ID NO 5

```
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
ctgggaatcg caccagcgtg t                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic Primer

<400> SEQUENCE: 6
ctgggacctc gcctatccca t                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic Primer

<400> SEQUENCE: 7
cgtggaaagg cggaccctca g                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
cgtggatgag gagccgcagt g                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
cgtggacaga ccccggtagt g                                              21

<210> SEQ ID NO 10
<211> LENGTH: 41
<212> TYPE: DNA
<213> ORGANISM: Artificial Sequence
<220> FEATURE:
<223> OTHER INFORMATION: Synthetic primer

<400> SEQUENCE: 10
ggattctaat acgactcact atagggtcgc gcccataact c                        41

<210> SEQ ID NO 11
<211> LENGTH: 41
<212> TYPE: DNA
<213> ORGANISM: Artificial Sequence
<220> FEATURE:
<223> OTHER INFORMATION: Synthetic primer

<400> SEQUENCE: 11
```

```
ggattctaat acgactcact atagggatcg caccagcgtg t                    41

<210> SEQ ID NO 12
<211> LENGTH: 40
<212> TYPE: DNA
<213> ORGANISM: Artificial Sequence
<220> FEATURE:
<223> OTHER INFORMATION: Synthetic primer

<400> SEQUENCE: 12
ggattctaat acgactcact atagggcctc gcctatccca                     40

<210> SEQ ID NO 13
<211> LENGTH: 14
<212> TYPE: DNA
<213> ORGANISM: Homo sapiens
<220> FEATURE:
<221> NAME/KEY: misc_feature
<222> LOCATION: (10)..(10)
<223> OTHER INFORMATION: N = A, G, C, or T/U

<400> SEQUENCE: 13
ctgccacctn gtgg                                                 14

<210> SEQ ID NO 14
<211> LENGTH: 30
<212> TYPE: DNA
<213> ORGANISM: Homo sapiens

<400> SEQUENCE: 14
gagcaattcc gccccctggt ggcagatctg                                30

<210> SEQ ID NO 15
<211> LENGTH: 14
<212> TYPE: DNA
<213> ORGANISM: Homo sapiens
<220> FEATURE:
<221> NAME/KEY: misc_feature
<222> LOCATION: (5)..(5)
<223> OTHER INFORMATION: N = A, G, C, or T/U

<400> SEQUENCE: 15
ccacnaggtg gcag                                                 14

<210> SEQ ID NO 16
<211> LENGTH: 30
<212> TYPE: DNA
<213> ORGANISM: Homo sapiens

<400> SEQUENCE: 16
ggcggagacc acaaggtggc gccagatccc                                30
```